US010266605B2

(12) United States Patent
Govindan et al.

(10) Patent No.: US 10,266,605 B2
(45) Date of Patent: Apr. 23, 2019

(54) EFFICACY OF ANTI-TROP-2-SN-38 ANTIBODY DRUG CONJUGATES FOR THERAPY OF TUMORS RELAPSED/REFRACTORY TO CHECKPOINT INHIBITORS

(71) Applicant: Immunomedics, Inc., Morris Plains, NJ (US)

(72) Inventors: Serengulam V. Govindan, Summit, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 140 days.

(21) Appl. No.: 15/490,535

(22) Filed: Apr. 18, 2017

(65) Prior Publication Data

US 2017/0313781 A1   Nov. 2, 2017

Related U.S. Application Data

(60) Provisional application No. 62/328,289, filed on Apr. 27, 2016.

(51) Int. Cl.
| | | |
|---|---|---|
| *A61K 39/395* | (2006.01) | |
| *C07K 16/30* | (2006.01) | |
| *A61K 45/06* | (2006.01) | |
| *A61K 47/68* | (2017.01) | |

(52) U.S. Cl.
CPC .............. *C07K 16/30* (2013.01); *A61K 45/06* (2013.01); *A61K 47/6801* (2017.08); *A61K 47/6851* (2017.08); *A61K 47/6855* (2017.08); *A61K 47/6857* (2017.08); *A61K 47/6859* (2017.08); *A61K 47/6863* (2017.08); *A61K 47/6865* (2017.08); *A61K 47/6867* (2017.08); *A61K 47/6869* (2017.08)

(58) Field of Classification Search
None
See application file for complete search history.

(56) References Cited

U.S. PATENT DOCUMENTS

| | | |
|---|---|---|
| 4,036,945 A | 7/1977 | Haber |
| 4,046,722 A | 9/1977 | Rowland |
| 4,200,690 A | 4/1980 | Root et al. |
| 4,331,647 A | 5/1982 | Goldenberg |
| 4,359,457 A | 11/1982 | Neville et al. |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Howthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,112,954 A | 5/1992 | Abrams et al. |
| 5,122,368 A | 6/1992 | Greenfield et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,679,640 A | 10/1997 | Gaeta et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,708,146 A | 1/1998 | Willner et al. |
| 5,716,595 A | 2/1998 | Goldenberg |
| 5,736,119 A | 4/1998 | Goldenberg et al. |
| 5,750,105 A | 5/1998 | Newman et al. |
| 5,776,456 A | 7/1998 | Anderson et al. |
| 5,789,554 A | 8/1998 | Leung et al. |

(Continued)

FOREIGN PATENT DOCUMENTS

| | | |
|---|---|---|
| CA | 2428885 | 5/2002 |
| CA | 2471717 | 7/2003 |

(Continued)

OTHER PUBLICATIONS

George et al. (Circulation. 1998; 97: 900-906), (Year: 1998).*
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Baines et al., "Purification of Immunoglobulin G (IgG)", Methods in Molecular Biology, vol. 10, pp. 79-104, Manson et al., (eds.), The Human Press (1992).

(Continued)

*Primary Examiner* — Sheela J. Huff
(74) *Attorney, Agent, or Firm* — Richard A. Nakashima

(57) ABSTRACT

The present invention relates to therapeutic ADCs comprising SN-38 attached to an anti-Trop-2 antibody or antigen-binding antibody fragment, more particularly sacituzumab govitecan. The ADC is administered to a subject with a Trop-2 positive cancer that is resistant to or relapsed from prior treatment with a checkpoint inhibitor. The therapy is effective to treat cancers that are resistant to checkpoint inhibitors.

25 Claims, 5 Drawing Sheets

Specification includes a Sequence Listing.

(56) References Cited

U.S. PATENT DOCUMENTS

| | | |
|---|---|---|
| 5,792,845 A | 8/1998 | O'Reilly et al. |
| 5,795,967 A | 8/1998 | Aggarwal et al. |
| 5,798,554 A | 8/1998 | Grimaldi et al. |
| 5,817,307 A | 10/1998 | Cummins |
| 5,824,701 A | 10/1998 | Greenwald et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,056,973 A | 5/2000 | Allen et al. |
| 6,077,499 A | 6/2000 | Griffiths et al. |
| 6,096,289 A | 8/2000 | Goldenberg |
| 6,156,754 A | 12/2000 | Lerchen et al. |
| 6,165,440 A | 12/2000 | Esenaliev |
| 6,183,744 B1 | 2/2001 | Goldenberg |
| 6,187,287 B1 | 2/2001 | Leung et al. |
| 6,201,104 B1 | 3/2001 | MacDonald et al. |
| 6,214,345 B1 | 4/2001 | Firestone et al. |
| 6,254,868 B1 | 7/2001 | Leung et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |
| 6,530,944 B2 | 3/2003 | West et al. |
| 6,562,318 B1 | 5/2003 | Filler |
| 6,653,104 B2 | 11/2003 | Goldenberg |
| 6,716,821 B2 | 4/2004 | Zhao et al. |
| 7,018,809 B1 | 5/2006 | Carter |
| 7,074,403 B1 | 7/2006 | Goldenberg et al. |
| 7,122,636 B1 | 10/2006 | Hsei et al. |
| 7,151,164 B2 | 12/2006 | Hansen et al. |
| 7,238,785 B2 | 7/2007 | Govindan et al. |
| 7,312,318 B2 | 12/2007 | Hansen et al. |
| 7,585,491 B2 | 9/2009 | Govindan et al. |
| 7,591,994 B2 | 9/2009 | Govindan et al. |
| 7,772,373 B2 | 8/2010 | Hansen et al. |
| 7,820,161 B1 | 10/2010 | Curd et al. |
| 7,910,103 B2 | 3/2011 | Goldenberg |
| 7,931,903 B2 | 4/2011 | Hansen et al. |
| 7,999,083 B2 | 8/2011 | Govindan et al. |
| 8,080,250 B1 | 12/2011 | Govindan et al. |
| 8,119,101 B2 | 2/2012 | Byrd et al. |
| 8,268,317 B2 | 9/2012 | Govindan et al. |
| 8,268,319 B2 | 9/2012 | Govindan et al. |
| 8,420,086 B2 | 4/2013 | Govindan et al. |
| 8,425,912 B2 | 4/2013 | Govindan et al. |
| 8,658,773 B2 | 2/2014 | Zeng et al. |
| 9,102,735 B2 | 8/2015 | Govindan et al. |
| 9,180,205 B2 | 11/2015 | Zeng et al. |
| 2001/0034363 A1 | 10/2001 | Li et al. |
| 2002/0018749 A1 | 2/2002 | Hudson et al. |
| 2003/0103979 A1 | 6/2003 | Leung et al. |
| 2003/0133972 A1 | 7/2003 | Danthi et al. |
| 2004/0001825 A1 | 1/2004 | Govindan et al. |
| 2004/0001838 A1 | 1/2004 | Zhao et al. |
| 2004/0076683 A1 | 4/2004 | Hoarau et al. |
| 2006/0122113 A1 | 6/2006 | Pinchasi et al. |
| 2006/0142506 A1 | 6/2006 | Breitenkamp et al. |
| 2006/0193865 A1 | 8/2006 | Govindan et al. |
| 2007/0212350 A1 | 9/2007 | Govindan et al. |
| 2008/0166363 A1 | 7/2008 | Govindan et al. |
| 2010/0104589 A1 | 4/2010 | Govindan et al. |
| 2010/0196266 A1 | 8/2010 | Goldenberg et al. |
| 2011/0160159 A1 | 6/2011 | Ryan |
| 2011/0256053 A1 | 10/2011 | Chang et al. |
| 2011/0274704 A1 | 11/2011 | Chang et al. |
| 2011/0305631 A1 | 12/2011 | Govindan et al. |
| 2012/0082617 A1 | 4/2012 | Govindan et al. |
| 2012/0328564 A1 | 12/2012 | Govindan et al. |
| 2013/0053334 A1 | 2/2013 | Manoharan et al. |
| 2013/0090458 A1 | 4/2013 | Govindan et al. |
| 2013/0156691 A1 | 6/2013 | Goldenberg et al. |
| 2013/0177526 A1 | 7/2013 | Govindan et al. |
| 2013/0216561 A1 | 8/2013 | Govindan et al. |
| 2014/0004078 A1 | 1/2014 | Govindan et al. |
| 2014/0058067 A1 | 2/2014 | Govindan et al. |
| 2014/0178294 A1 | 6/2014 | Zeng et al. |
| 2015/0306243 A1 | 10/2015 | Govindan et al. |
| 2015/0366988 A1 | 12/2015 | Goldenberg et al. |
| 2016/0009805 A1 | 1/2016 | Kowanetz et al. |
| 2016/0032008 A1 | 2/2016 | Zeng et al. |

FOREIGN PATENT DOCUMENTS

| | | |
|---|---|---|
| EP | 0253202 | 1/1988 |
| EP | 0306943 | 3/1989 |
| EP | 0332865 | 9/1989 |
| EP | 0510949 | 10/1992 |
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67796 | 11/2000 |
| WO | 0067795 | 11/2000 |
| WO | 0074718 | 12/2000 |
| WO | 0076551 | 12/2000 |
| WO | 0124763 | 4/2001 |
| WO | 2004054622 | 7/2004 |
| WO | 2007123995 | 11/2007 |
| WO | 2012/097081 | 7/2012 |
| WO | 2012151199 | 11/2012 |

OTHER PUBLICATIONS

Bambot et al., "Efficient total gene synthesis of 1.35-kb hybrid alpha-lytic protease gene using the polymerase chain reaction", PCR Methods Appl. Feb. 1993;2(3):266-71.

Baum et al., "Initial clinical results with technetium-99m-labeled LL2 monoclonal antibody fragment in the radioimmunodetection of B-cell lymphomas", Cancer Feb. 1, 1994;73(3 Suppl):896-9.

Beers et al., The Merck Manual of Diagnosis and Therapy, Ch. 180, p. 1474-1476; 17th Ed., Whitehouse Station, NJ, Merck Research Labs (1999).

Belisle et al., "Epitope specificity of the anti-B-cell lymphoma monoclonal antibody, LL2", Proc Am Assoc Cancer Res 1993; 34:481, Abstr #2873.

Bendig, M., "Humanization of Rodent Monoclonal Antibodies by CDR Grafting", Academic Press Inc., New York, NY, vol. 8, (1995), pp. 83-93.

Bhat et al., "Human antilipid A monoclonal antibodies bind to human B cells and the i antigen on cord red blood cells", J Immunol. Nov. 1, 1993;151(9):5011-21.

Carter et al., "Humanization of an anti-p185HER2 antibody for human cancer therapy", Proc. Natl. Acad. Sci. USA 89(10):4285-9 (1992).

Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.

Coloma et al., "Design and production of novel tetravalent bispecific antibodies", Nat. Biotechnol. 15(2):159-63 (1997).

Dillon et al., "Use of Polymerase Chain Reaction for the Rapid Construction of Synthetic Genes", Methods in Molecular Biology, vol. 15: PCR Protocols: Current Methods and Applications, White (Ed.), pp. 263-268, Humana Press, Inc. (1993).

Ellis et al., "Engineered anti-CD38 monoclonal antibodies for immunotherapy of multiple myeloma", J Immunol. Jul. 15, 1995;155(2):925-37.

Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).

(56) References Cited

OTHER PUBLICATIONS

Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.
French et al., "Response of B-cell lymphoma to a combination of bispecific antibodies and saporin", Leuk. Res. 20(7):607-17 (1996).
Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Goldenberg et al., "Targeting, dosimetry, and radioimmunotherapy of B-cell lymphomas with iodine-131-labeled LL2 monoclonal antibody", J Clin Oncol. Apr. 1991;9(4):548-64.
Goldenberg, D. M. "New Developments in Monoclonal Antibodies for Cancer Detection and Therapy", CA Cancer J. Clin. 44(1):43-64 (1994).
Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and in Combination with Veltuzumab, a Humanized Anti-CD20 MAb", Blood (ASH Annual Meeting Abstracts) 2010 116: Abstract 3941.
Gondo et al., "HLA class II antigen associated invariant chain gene expression in malignant lymphoma", Br. J. Haematol. 67(4):413-7 (1987).
Green et al., "Antigen-specific human monoclonal antibodies from mice engineered with human Ig heavy and light chain YACs", Nature Genetics 7:13-21 (1994).
Gussow et al., "Humanization of monoclonal antibodies", Methods Enzymol. 1991;203:99-121.
Hansen et al., "Internalization and catabolism of radiolabelled antibodies to the MHC class-II invariant chain by B-cell lymphomas", Biochem. J. 1996, 320:293-300.
Hashida et al., "More useful maleimide compounds for the conjugation of Fab' to horseradish peroxidase through thiol groups in the hinge", J Appl Biochem. Feb.-Apr. 1984;6(1-2):56-63.
Hekman et al., "Initial experience with treatment of human B cell lymphoma with anti-CD19 monoclonal antibody", Cancer Immunol. Immunother. 1991;32(6):364-72.
Hess et al., "Specificity of effector T lymphocytes in autologous graft-versus-host disease: role of the major histocompabbility complex class II invariant chain peptide", Blood 89(6):2203-9 (1997).
Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.
Imuran patient information leaflet, GlaxoSmithKline 7076598/5093, Oct. 2004.
Inaoki et al., "CD19-regulated signaling thresholds control peripheral tolerance and autoantibody production in B lymphocytes", J Exp Med. Dec. 1, 1997;186(11):1923-31.
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiener et al., "Stimulation of CD40 with purified soluble gp39 induces proinflammatory responses in human monocytes", J Immunol. Nov. 15, 1995;155(10):4917-25.
Kiesel et al., "Removal of cells from a malignant B-cell line from bone marrow with immunomagnetic beads and with complement and immunoglobulin switch variant mediated cytolysis", Leuk. Res. 11(12):1119-25 (1987).

Kohler et al., "Continuous cultures of fused cells secreting antibody of predefined specificity", Nature 256:495-7 (1975).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).
Leung et al., "Chimerization and humanization of a B-cell Lymphoma specific antibody, LL2", Proc Am Assoc Cancer Res 1993; 34:481, Abstr #2872.
Leung et al., "Chimerization of LL2, a Rapidly Internalizing Antibody Specific for B Cell Lymphoma", Hybridoma 13(6):469-476 (1994).
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52(8):1701-4 (1999).
Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L., "Immunotherapy for non-Hodgkin's lymphoma", Curr. Opin. Oncol. 8(5):353-9 (1996).
Losman et al., "Baboon anti-idiotype antibodies mimic a carcinoembryonic antigen epitope", Int J Cancer. Aug. 15, 1990;46(2):310-4.
Lundberg, B., "Preparation of drug-carrier emulsions stabilized with phosphatidylcholine-surfactant mixtures", J. Pharm. Sci. 83(1):72-5 (1994).
Lundberg et al., "Submicron lipid emulsions containing amphipathic polyethylene glycol for use as drug-carriers with prolonged circulation time", Int. J. Pharm. 134:119-127 (1996).
Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11(9):1936-47.
Bennouna et al., "Therapeutic strategies for colorectal cancer in Europe and the United States: focus on chemotherapy for advanced colorectal cancer" Int. J. Clin. Oncol. (2002) 7:236-244.
Burkard et al., "Validating cancer drug targets through chemical genetics", Biochim Biophys Acta. Dec. 2010;1806(2):251-7.
Burke et al., "Design, synthesis, and biological evaluation of antibody-drug conjugates comprised of potent camptothecin analogues", Bioconjug Chem. Jun. 2009;20(6):1242-50.
Burnham et al., "Invasion of HeLa cells by group B *Streptococcus* requires the phosphoinositide-3-kinase signalling pathway and modulates phosphorylation of host-cell Akt and glycogen synthase kinase-3", Microbiology. Dec. 2007;153(Pt 12):4240-52.
Cao et al., "Bispecific Antibodies as Novel Bioconjugates" Bioconj. Chem. Nov.-Dec. 1998;9(6):635-44.
Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.
Carter et al., Chemotherapy of Cancer; 2nd Edition; John Wiley & Sons, New York, 1981; Appendix C.
Chari et al., "Immunoconjugates Containing Novel Maytansinoids: Promising Anticancer Drugs" Cancer Res. Jan. 1, 1992;52(1):127-31.
Feldmann et al., "Design of effective immunotherapy for human autoimmunity", Nature. Jun. 2, 2005;435(7042):612-9.
Fukuda et al., "Evaluation of novel platinum complexes, inhibitors of topoisomerase I and II in non-small cell lung cancer (NSCLC) sublines resistant to cisplatin", Anticancer Res. Mar.-Apr. 1995;15(2):393-8.

(56) References Cited

OTHER PUBLICATIONS

Garcia-Giron et al., "Phase II trial of fortnightly irinotecan (CPT-11) in the treatment of colorectal cancer patients resistant to previous fluoropyrimidine-based chemotherapy", Clin Transl Oncol. Jul. 2005;7(6):244-9.
Gomez-Manzano et al., "Delta-24 increases the expression and activity of topoisomerase I and enhances the antiglioma effect of irinotecan", Clin Cancer Res. Jan. 15, 2006;12(2):556-62.
Govindan et al., "Milatuzumab-SN-38 conjugates for the treatment of CD74+ cancers", Mol Cancer Ther. Jun. 2013;12(6):968-78.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Gura, T., "Systems for identifying new drugs are often faulty", Science. Nov. 7, 1997;278(5340):1041-2.
Hatzakis et al., "Synthesis and single enzyme activity of a clicked lipase-BSA hetero-dimer" Chem. Commun., 2006, 2012-2014.
He et al., "Synthesis and biological evaluation of bis and monocarbonate prodrugs of 10-hydroxycamptothecins", Bioorg Med Chem. Aug 1, 2004;12(15):4003-8.
Heindel et al., "A Novel Heterobifunctional Linker for Formyl to Thiol Coupling" Bioconjugate Chem. 1991, 2, 427-430.
Horwitz et al., "Antiviral action of camptothecin", Antimicrob Agents Chemother. Nov. 1972;2(5):395-401.
Huang et al., "The Rana catesbeiana rcr Gene Encoding a Cytotoxic Ribonuclease" J. Biol. Chem. 273 (11):6395-6401 (1998).
Kaiser, J., "Cancer. First pass at cancer genome reveals complex landscape", Science. Sep. 8, 2006;313(5792):1370.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Krontiris and Capizzi, Internal Medicine, Chapters 71-72, pp. 699-729; 4th Edition, Jay Stein (Ed.), Elsevier Science, 1994.
Kufe et al., Non-Intercalating Topoisomerase-Targeting Drugs, Holland-Frei Cancer Medicine, Hamilton (ON), BC Decker (2003).
Kufe et al., Topoisomerase Biology, 6th Ed., Holland-Frei Cancer Medicine, Hamilton (ON), BC Decker (2003).
Mahato et al., "Prodrugs for improving tumor targetability and efficiency", Adv Drug Deliv Rev. Jul 18, 2011;63(8):659-70.
Matsumura, Y., "Preclinical and clinical studies of NK012, an SN-38-incorporating polymeric micelles, which is designed based on EPR effect", Adv Drug Deliv Rev. Mar. 18, 2011;63(3):184-92.
Miller et al., "Development of Taxoids with Enhanced Toxicity and Solubility" Poster Presentation, 224th ACS Nat. Meeting, Aug. 18-22, 2002, Boston, MA.
Mine Safety and Health Administration (Special Hazards of Acetylene, Sep. 16, 2011).
Moon et al., "Antibody Conjugates of 7-Ethyl-10-hydroxycamptothecin (SN-38) for Targeted Cancer Chemotherapy" J. Med. Chem. 2008, 51, 6916-6926.
Newton et al., "Potent and specific antitumor effects of an anti-CD22-targeted cytotoxic ribonuclease: potential for the treatment of non-Hodgkin lymphoma" Blood, 97(2):528-35 (2001).
Paul, W., ed., Fundamental Immunology, 3rd Ed., Raven Press, New York, 1993, p. 292-295.
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Reddy et al., "Elimination of Fc Receptor-Dependent Effector Functions of a Modified IgG4 Monoclonal Antibody to Human CD4", J. Immunol. 164:1925-1933 (2000).
Rowlinson-Busza et al., "Targeted delivery of biologic and other antineoplastic agents" Curr. Opin. Oncol. Dec. 1992;4(6):1142-1148.
Sharkey et al., "Epratuzumab-SN-38: a new antibody-drug conjugate for the therapy of hematologic malignancies", Mol Cancer Ther. Jan. 2012;11(1):224-34.
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Shih et al., "The Processing and Fate of Antibodies and Their Radiolabels Bound to the Surface of Tumor Cells In Vitro: A Comparison of Nine Radiolabels" J. Nucl. Med. 1994; 35:899-908.
Shih et al., "In vitro and in vivo reactivity of an internalizing antibody, RS7, with human breast cancer", Cancer Res. Dec. 1, 1995;55(23 Suppl):5857s-5863s.
Stanford University Environmental Health and Safety (Information on Azide Compounds, Dec. 2, 2008).
Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).
Suzawa et al., "Enhanced tumor cell selectivity of adriamycin-monoclonal antibody conjugate via a poly(ethylene glycol)-based cleavable linker" J. Control. Release 79:229-242 (2002).
Talmadge et al., "Murine models to evaluate novel and conventional therapeutic strategies for cancer", Am J Pathol. Mar. 2007;170(3):793-804.
Thurber et al., "Antibody tumor penetration: transport opposed by systemic and antigen-mediated clearance", Adv Drug Deliv Rev. Sep. 2008;60(12):1421-34.
Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.
Van Noort and Amor, "Cell Biology of Autoimmune Disease", vol. 178, pp. 127-206; International Rev. of Cytology, 1998.
Walker et al., "Synthesis of an Immunoconjugate of Camptothecin" Bioorg. Med. Chem. Lett. 12(2):217-219 (2002).
Bardia et al., "Safety and efficacy of anti-Trop-2 antibody drug conjugate, sacituzumab govitecan (IMMU-132), in heavily pre-treated patients with TNBC", Poster presented at San Antonio Breast Cancer Symposium, Dec. 10, 2015, San Antonio, TX.
Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.
Basu et al., "The epithelial/carcinoma antigen EGP-1, recognized by monoclonal antibody RS7-3G11, is phosphorylated on serine 303", Int J Cancer. Aug. 9, 1995;62(4):472-9.
Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.
Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference on Lung Cancer (WCLC), Sep. 7, 2015, Denver, CO.
Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.
Cardillo et al., "Combining an anti-Trop-2 antibody-SN-38 conjugate (sacituzumab govitecan) with microtubule inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.
Cardillo et al., "Synthetic lethality in TNBC mediated by an anti-Trop-2 antibody-drug conjugate, sacituzumab govitecan (IMMU-

(56) References Cited

OTHER PUBLICATIONS

132), when combined with paclitaxel or the PARP inhibitor, olaparib", Poster presented at San Antonio Breast Cancer Symposium, Dec. 10, 2015, San Antonio, TX.

Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31, Epub May 8, 2015.

Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.

Goldenberg et al., Tolerability in mice, monkeys, and rabbits of new antibody (MAb)-drug (SN-38) immunoconjugates. Proc. Amer. Assoc. Cancer Res. 102nd Annual Meeting, 52: 865 (Abstr. #3619), 2011.

Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.

Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.

Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.

Goldenberg et al., "Trop-2 is a novel target for solid cancer therapy with sacituzumab govitecan (IMMU-132), an antibody-drug conjugate (ADC)", Oncotarget Jun. 18, 2015. [Epub ahead of print].

Govindan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.

Govindan et al., "Preclinical therapy of breast cancer with a radioiodinated humanized anti-EGP-1 monoclonal antibody: advantage of a residualizing iodine radiolabel", Breast Cancer Res Treat Mar. 2004;84(2):173-82.

Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.

Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.

Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.

Guarino et al., "Therapy of advanced metastatic lung cancer with an anti-Trop-2-SN-38 antibody-drug conjugate (ADC), sacituzumab govitecan (IMMU-132): Phase I/II clinical experience", J Clin Oncol 33, 2015 (suppl; abstr 2504), Retrieved from http://meetinglibrary.asco.org/content/148373-156.

Liu et al., "Novel immunoRNases comprising multiple copies of ranpimase display potent cytotoxicity in human breast cancer cell lines expressing Trop-2", Proc. Amer. Assoc. Cancer Res. 103rd Annual Meeting, 53: 1124 (Abstr. #4636), 2012.

NCT01270698 (Jan. 3, 2011, pp. 1-4).

NCT01605318 (May 22, 2012, pp. 1-4).

Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.

Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR) Special Conference on Pancreatic Cancer:Innovations in Research and Treatment, Abstr. #B99, May 18-21, 2014.

Sharkey et al., "Enhanced Delivery of SN-38 to Human Tumor Xenografts with an Anti-Trop-2-SN-38 Antibody Conjugate (Sacituzumab Govitecan)", Clin Cancer Res. Jun. 23, 2015. pii: clincanres.0670.2015. [Epub ahead of print].

Shih et al., "Radioimmunodetection and radioimmunotherapy of xenografted human breast cancer with monoclonal antibody RS7", J. Immunother. 16: 169 (Abstr. #85), 1994.

Starodub et al., "Advanced solid cancer therapy with a novel antibody-drug conjugate (ADC), sacituzumab govitecan (IMMU-132): key preclinical and clinical results", Abstract CT236. Presented at American Association for Cancer Research (AACR) 2015 Annual Meeting, Philadelphia, PA, Apr. 20, 2015.

Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.

Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.

Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.

Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].

Starodub et al., "Phase I/II trial of IMMU-132 (isactuzumab govitecan), an anti-Trop-2-SN-38 antibody drug aonjugate (ADC): Results in patients with metastatic gastrointestinal (GI) cancers", J Clin Oncol 33, 2015 (suppl 3; abstr 703), Retrieved from http://meetinglibrary.asco.org/content/140198-158.

Stein et al., "Therapy of a breast cancer xenograft using humanized RS7 labeled with residualizing iodine", Proc. Amer. Assoc. Cancer Res. 43: 88 (Abstr. #413), 2002.

Stein et al., "Radioimmunotherapy of lung cancer with MAb RS7-3G11", Proc. Amer. Assoc. Cancer Res. 33: 318 (Abstr. #1897), 1992.

Stein et al., "Radioimmunotherapy with MAb RS7-3G11 in an animal model", Antib. Immunoconj. Radiopharm. 5: 358 (Abstr. #100), 1992.

Stein et al., "Specificity and properties of MAb RS7-3G11 and the antigen defined by this pancarcinoma monoclonal antibody", Int J Cancer. Dec. 2, 1993;55(6):938-46.

Stein et al., "Comparative biodistribution and radioimmunotherapy of monoclonal antibody RS7 and its F(ab')2 in nude mice bearing human tumor xenografts", Cancer. Feb. 1, 1994;73(3 Suppl):816-23.

Stein et al., "Murine monoclonal antibodies raised against human non-small cell carcinoma of the lung: specificity and tumor targeting", Cancer Res. Feb. 15, 1990;50(4):1330-6.

Stein et al., "Effects of radiolabeling monoclonal antibodies with a residualizing iodine radiolabel on the accretion of radioisotope in tumors", Cancer Res. Jul. 15, 1995;55(14):3132-9.

Stein et al., "Successful therapy of a human lung cancer xenograft using MAb RS7 labeled with residualizing radioiodine", Rev Oncol Hematol. Jul.-Aug. 2001;39(1-2):173-80.

Stein et al., "Assessment of combined radioimmunotherapy and chemotherapy for treatment of medullary thyroid cancer", Clin Cancer Res. 5(10 Suppl):3199s-206s, 1999.

(56) References Cited

OTHER PUBLICATIONS

Stein et al., Characterization of the epithelial/carcinoma antigen recognized by MAb RS7. Prov Amer. Assoc. Cancer Res. 35: 501 (Abstr. #2986), 1994.

Stein et al., A novel tumor-associated antigen defined by MAb RS7-3G11: Characterization and internalization properties. Proc. Amer. Assoc. Cancer Res. 33: 341, 1992.

Stein et al., "Characterization of cluster 13: the epithelial/carcinoma antigen recognized by MAb RS7", Int J Cancer Suppl. 1994;8:98-102.

Stein et al., "Targeting and therapy of human non small cell carcinoma of the lung xenografts using 131 I labeled monoclonal antibody RS7 3G11", Proc. Amer. Assoc. Cancer Res. 32: 260, 1991.

Van Rij et al., "Imaging of prostate cancer with immuno-PET and immuno-SPECT using a radiolabeled anti-EGP-1 monoclonal antibody", J Nucl Med. 52(10):1601-7, 2011.

Van Rij et al., "Pretargeting of prostate cancer with an internalizing anti-EGP-1 x anti-HSG bispecific antibody", Annual Congress of the European Association of Nuclear Medicine, Birmingham, UK, Eur J Nucl Med Mol Imaging 38 (Suppl 2):S212 (Abstr. #OP582), 2011.

Vanama et al., Construction, characterization, and mammalian expression of an immunotoxin consisting of ranpirnase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.

Bardia et al., "Efficacy and Safety of Anti-Trop-2 Antibody Drug Conjugate Sacituzumab Govitecan (IMMU-132) in Heavily Pretreated Patients With Metastatic Triple-Negative Breast Cancer", J Clin Oncol. Jul. 1, 2017;35(19):2141-2148.

Bardia et al., "Therapy of refractory/relapsed metastatic triple-negative breast cancer (TNBC) with an anti-Trop-2-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.

Berger et al., "Phase I safety and pharmacokinetic study of CT-011, a humanized antibody interacting with PD-1, in patients with advanced hematologic malignancies", Clin Cancer Res. May 15, 2008;14(10):3044-51.

Brahmer et al., "Safety and activity of anti-PD-L1 antibody in patients with advanced cancer", N Engl J Med. Jun. 28, 2012;366(26):2455-65

Cotarca et al., Phosphogenations, a Handbook. Wiley-VCH Verlag GmbH abd Co. KGaA, Weinheim,Germany, 2003, p. 3; p. 404.

Dang et al., "Hypoxia-inducible factor-1 target genes as indicators of tumor vessel response to vascular endothelial growth factor inhibition", Cancer Res. Mar. 15, 2008;68(6):1872-80.

Declaration under 37 C.F.R. 1.132 by David M. Goldenberg, filed in U.S. Appl. No. 13/948,732, filed Jun. 20, 2014.

Declaration under 37 C.F.R. 1.132 by David M. Goldenberg, filed in U.S. Appl. No. 14/204,698, filed Jan. 7, 2015.

Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.

Faltas et al., "Sacituzumab Govitecan, a Novel Antibody-Drug Conjugate, in Patients With Metastatic Platinum-Resistant Urothelial Carcinoma", Clin Genitourin Cancer. Feb. 2016;14(1):e75-9.

Gildener-Leapman et al., "Promising systemic immunotherapies in head and neck squamous cell carcinoma", Oral Oncol. Dec. 2013;49(12):1089-96.

Govindan et al., "CEACAM5-targeted therapy of human colonic and pancreatic cancer xenografts with potent labetuzumab-SN-38 immunoconjugates", Clin Cancer Res. Oct. 1, 2009;15(19):6052-61.

Govindan et al., "Improving the Therapeutic Index in Cancer Therapy by Using Antibody-Drug Conjugates Designed with a Moderately Cytotoxic Drug", Mol Pharm. Nov. 25, 2014. [Epub ahead of print].

Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.

Grothey et al., "Survival of patients with advanced colorectal cancer improves with the availability of fluorouracil-leucovorin, irinotecan, and oxaliplatin in the course of treatment", J Clin Oncol. Apr. 1, 2004;22(7):1209-14.

Harmsen et al., "Properties, production, and applications of camelid single-domain antibody fragments", Appl Microbiol Biotechnol. Nov. 2007;77(1):13-22.

Heist et al., "Therapy of Advanced Non-Small-Cell Lung Cancer With an SN-38-Anti-Trop-2 Drug Conjugate, Sacituzumab Govitecan", J Clin Oncol. May 26, 2017:JCO2016721894, [Epub ahead of print].

Jefferis et al., "Human immunoglobulin allotypes: possible implications for immunogenicity", MAbs. Jul.-Aug. 2009;1(4):332-8.

Koyama et al., "Adaptive resistance to therapeutic PD-1 blockade is associated with upregulation of alternative immune checkpoints", Nat Commun. Feb. 17, 2016;7:10501.

Lebreton et al., "Application of high-performance tangential flow filtration (HPTFF) to the purification of a human pharmaceutical antibody fragment expressed in *Escherichia coli*", Biotechnol Bioeng. Aug. 1, 2008;100(5):964-74.

Lipson et al., "Durable cancer regression off-treatment and effective reinduction therapy with an anti-PD-1 antibody", Clin Cancer Res. Jan. 15, 2013;19(2):462-8.

Menzies et al., "New combinations and immunotherapies for melanoma: latest evidence and clinical utility", Ther Adv Med Oncol. Sep. 2013;5(5):278-85.

Ott et al., "Impact of MAPK Pathway Activation in BRAF(V600) Melanoma on T Cell and Dendritic Cell Function", Front Immunol. Oct. 28, 2013;4:346.

Ott et al., "CTLA-4 and PD-1/PD-L1 blockade: new immunotherapeutic modalities with durable clinical benefit in melanoma patients", Clin Cancer Res. Oct. 1, 2013;19(19):5300-9.

Pardoll, DM., "The blockade of immune checkpoints in cancer immunotherapy", Nat Rev Cancer. Mar. 22, 2012;12(4):252-64.

Radvanyi et al., "Antagonist antibodies to PD-1 and B7-I-11 (PD-L1) in the treatment of advanced human cancer letter", Clin Cancer Res. Oct. 1, 2013;19(19):5541.

Reagan-Shaw et al., "Dose translation from animal to human studies revisited", FASEB J. Mar. 2008;22(3):659-61.

Robert et al., "What is the role of cytotoxic T lymphocyte-associated antigen 4 blockade in patients with metastatic melanoma?", Oncologist Aug. 2009;14(8):848-61.

Segal et al., "IMMU-130, an SN-38 antibody-drug conjugate (ADC) targeting CEACAM5, is therapeutically active in metastatic colorectal cancer (mCRC): Initial clinical results of two Phase I studies", 2014 AACR Meeting Apr. 5-9, 2-14, San Diego, CA (Abstract No. CT211).

Seruga et al., "Failures in Phase III: Causes and Consequences", Clin Cancer Res. Oct. 15, 2015;21(20):4552-60.

Topalian et al., "Safety, activity, and immune correlates of anti-PD-1 antibody in cancer", N Engl J Med. Jun. 28, 2012;366(26):2443-54.

Wada et al., "Sequencing CTLA-4 blockade with cell-based immunotherapy for prostate cancer", J Transl Med. Apr. 4, 2013;11:89.

Weber, J., "Review: anti-CTLA-4 antibody ipilimumab: case studies of clinical response and immune-related adverse events", Oncologist. Jul. 2007;12(7):864-72.

Beckman et al., "Antibody constructs in cancer therapy: protein engineering strategies to improve exposure in solid tumors", Cancer. Jan. 15, 2007;109(2):170-9.

Berenbaum, MC., "Synergy, additivism and antagonism in immunosuppression. A critical review", Clin Exp Immunol. Apr. 1977;28(1):1-18.

Berenbaum, MC., "What is synergy?", Pharmacol Rev. Jun. 1989;41(2):93-141.

(56) References Cited

OTHER PUBLICATIONS

Cespedes et al., "Mouse models in oncogenesis and cancer therapy", Clin Transl Oncol. May 2006;8(5):318-29.
Dennis, C., "Cancer: off by a whisker", Nature. Aug. 17, 2006;442(7104):739-41.
Foran, JM., "Antibody-based therapy of non-Hodgkin's lymphoma", Best Pract Res Clin Haematol. Sep. 2002;15(3):449-65.
Fujimori et al., "A modeling analysis of monoclonal antibody percolation through tumors: a binding-site barrier", J Nucl Med. Jul. 1990;31(7):1191-8.
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.
Mason et al., "Value of monoclonal anti-CD22 (p135) antibodies for the detection of normal and neoplastic B lymphoid cells", Blood. Mar. 1987;69(3):836-40.
Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).
Morrison et al., "Chimeric human antibody molecules: mouse antigen-binding domains with human constant region domains", Proc Natl Acad Sci USA Nov. 1984;81(21):6851-5.
Murthy et al., "Lymphoma imaging with a new technetium-99m labelled antibody, LL2", Eur J Nucl Med. 1992;19(6):394-401.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human lymphoma", Cancer Res. 49(16):4568-77 (1989).
Perrotta et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates", Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).

Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86(24):10029-33.
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79(6):1979-83 (1982).
Rudnick et al., "Affinity and avidity in antibody-based tumor targeting", Cancer Biother Radiopharm. Apr. 2009;24(2):155-61.
Saltzman et al., "Transport rates of proteins in porous materials with known microgeometry", Biophys. J. 55(1):163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sherwood et al., "Controlled antibody delivery systems", Biotechnology 10(11):1446-9 (1992).
Shin et al., "Internalization and intracellular processing of an anti-B-cell lymphoma monoclonal antibody, LL2", Int J Cancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Tallarida, RJ., Drug Synergism and Dose Effect Analysis, Ed. Chapman & Hall, 2000, pp. 1-8; 10-13; 57-71.
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Tsang et al.,"Reactive oxygen species mediate doxorubicin induced p53-independent apoptosis", Life Sci. Sep. 5, 2003;73(16):2047-58.
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Wilson et al., "cDNA cloning of the B cell membrane protein CD22: a mediator of B-B cell interactions", J Exp Med. Jan. 1, 1991;173(1):137-46.
Wilson et al., "Genomic structure and chromosomal mapping of the human CD22 gene", J Immunol. Jun. 1, 1993;150(11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies for their capacity to induce cell-mediated lysis of malignant B cells", Cancer Res. Jul. 15, 1998;58(14):3051-8.

* cited by examiner

| Patient Summary | | | | | | | | |
|---|---|---|---|---|---|---|---|---|
| | | | CORE | | | | | 255-029 |
| | | | Modality CT Measurement Longest Diameter | | | | | |
| | | | Protocol: 13-541 Phase I/II: IMMU-132 in Patients with Epithelial Cancer | | | | | |
| Patient: XXXXXXXX Initials: JWG DOB: 09/28/1967 XXXXXXXX Disease: Breast Treatment Start Date: 02/12/2015 | | | | | | | | |
| # | Location | Target | Baseline | Scan 2 | Scan 3 | Scan 4 | Scan 5 | Scan 6 |
| | | | 01/29/15 | 04/07/15 | 05/19/15 | 07/19/15 | 09/13/15 | 11/15/15 |
| 1 | Lung LUL | Y | 23.7 x 18.8 mm (S:6, I:51) | 13.9 x 9.9 mm (S:3, I:50) | 13.8 x 9.0 mm (S:2, I:39) | 13.4 x 7.1 mm (S:2, I:39) | 12.1 x 5.2 mm (S:2, I:40) | 12.0 x 6.8 mm (S:2, I:36) |
| 2 | Lymph Node Mediastinal | Y | 17.2 x 28.9 mm (S:6, I:49) | 14.0 x 25.3 mm (S:3, I:53) | 10.9 x 22.6 mm (S:2, I:39) | 9.0 x 19.4 mm (S:2, I:40) | 9.0 x 18.4 mm (S:2, I:41) | 8.4 x 18.5 mm (S:2, I:39) |
| 3 | Lymph Node Hilar Left | Y | 19.1 x 24.0 mm (S:6, I:55) | 12.2 x 14.0 mm (S:3, I:56) | 6.6 x 12.4 mm (S:2, I:42) | 7.6 x 12.2 mm (S:2, I:42) | 7.5 x 13.7 mm (S:2, I:45) | 7.5 x 13.0 mm (S:2, I:42) |
| 4 | Lymph Node Mediastinal & Hilar | N | NM (S:6, I:65) | SD (S:3, I:65) | SD (S:2, I:49) | SD (S:2, I:50) | SD (S:2, I:51) | SD (S:2, I:49) |
| | RECIST1.1 | | 60.0 | 40.1 | 31.3 | 30.0 | 28.6 | 27.9 |
| | % change from Baseline: | | 0 | -33.2 | -47.8 | -50 | -52.3 | -53.5 |
| | % change from Nadir: | | 0 | -33.2 | -21.9 | -4.2 | -4.7 | -2.4 |
| | Scan used for Nadir: | | | Baseline | Scan 2 | Scan 3 | Scan 4 | Scan 5 |
| | % change from Prior: | | 0 | -33.2 | -21.9 | -4.2 | -4.7 | -2.4 |
| | Response: | | BL | PR | PR | PR | PR | PR |
| | Comment: | | CAP CT & PET-CT: LUL pulmonary nodule. Mediastinal and left hilar lymphadenopathy. These lesions are FDG-avid. In PET-CT there is a FDG-avid lesion in right lower internal mammary with no correlation on CT. | CAP CT: Interval decrease in tumor burden. | CAP CT: Stable to slight decrease in tumor burden. | CAP CT: Stable appearance compared to prior scan. | No new lesions. | CAP CT: Stable appearance with no new lesions. |
| | Radiologist: | | Nikhil Ramaiya, M.D. | Nikhil Ramaiya, M.D. | Nikhil Ramaiya, M.D. | Fiona Fennessy, M.D. | Avinash Kambadakone, M.D. | George Oliveira, M.D. |
| | Approval Date: | | 2/9/2015 8:29:00 am | 4/9/2015 9:38:00 am | 5/21/2015 8:45:00 am | 7/22/2015 9:28:00 am | 9/14/2015 1:55:00 pm | 11/16/2015 2:04:00 pm |

*FIG. 1*

FIG. 3
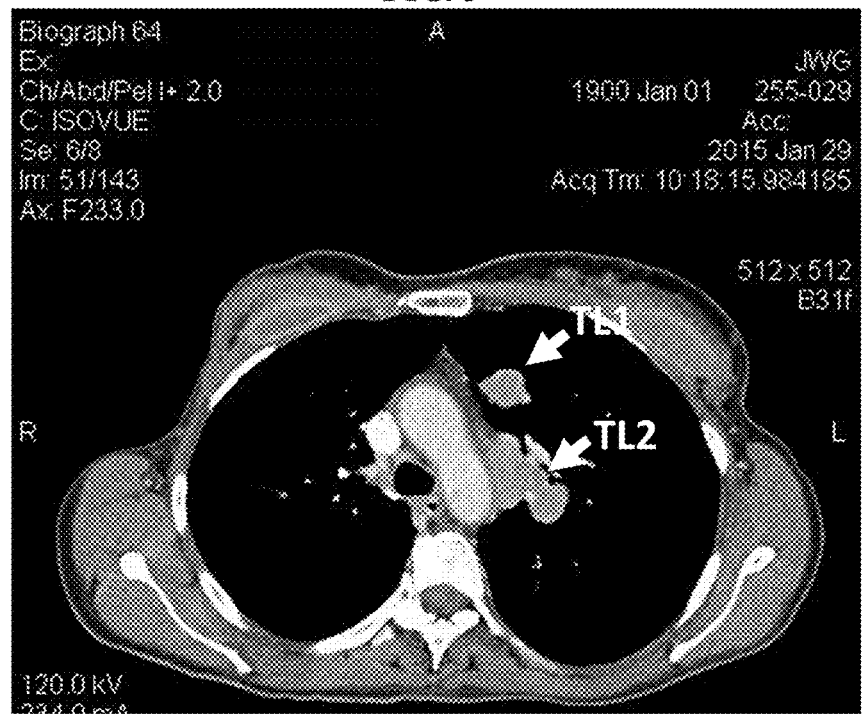
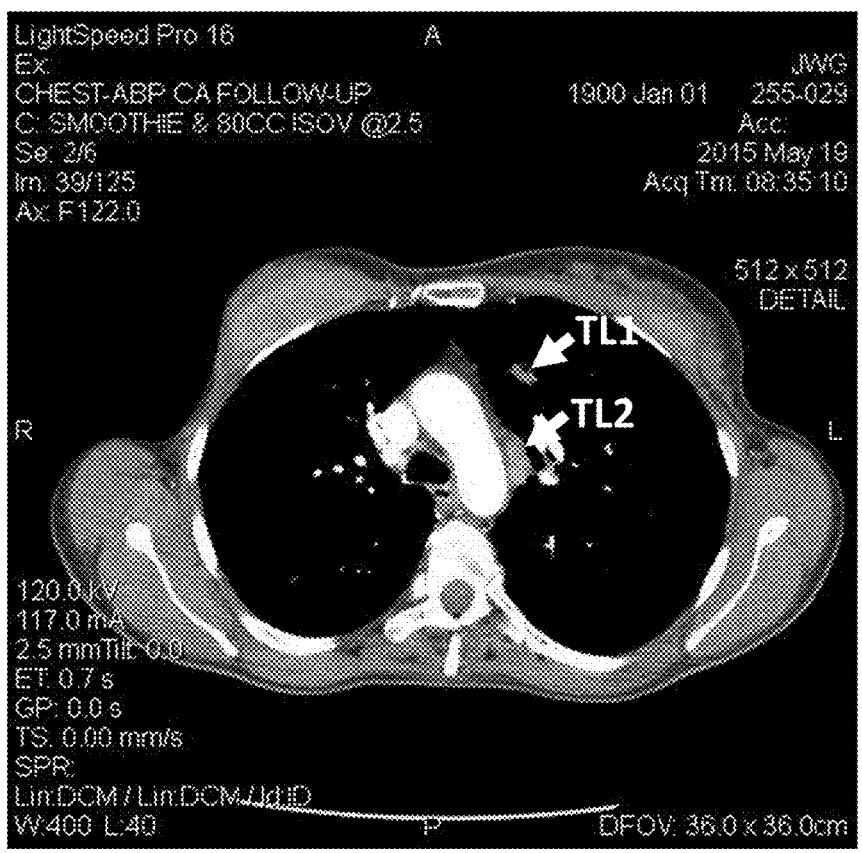

*FIG. 4*
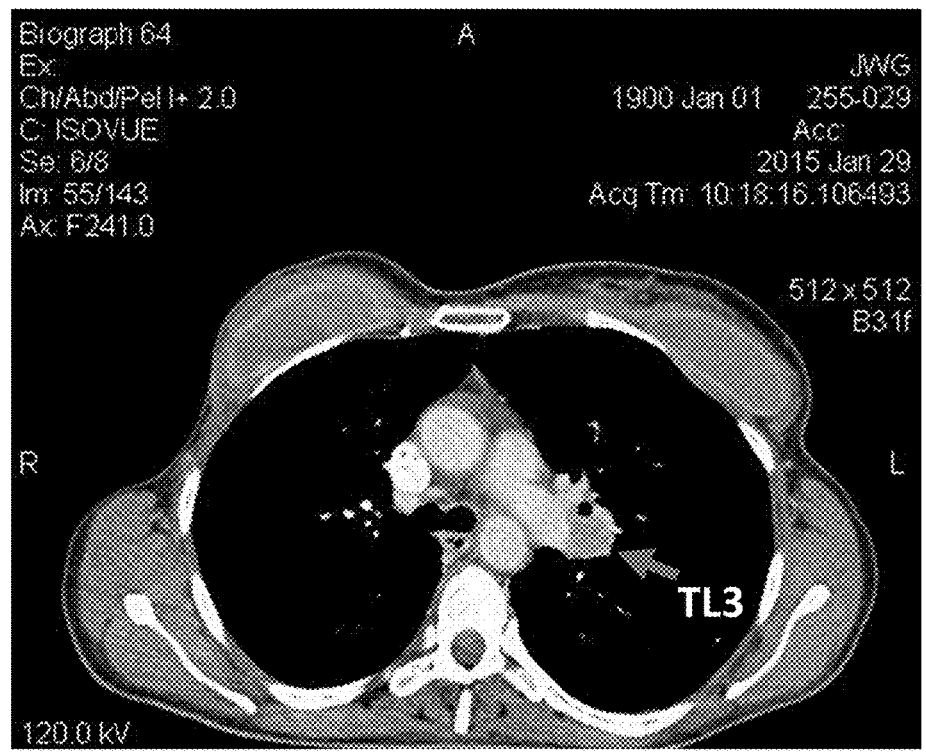
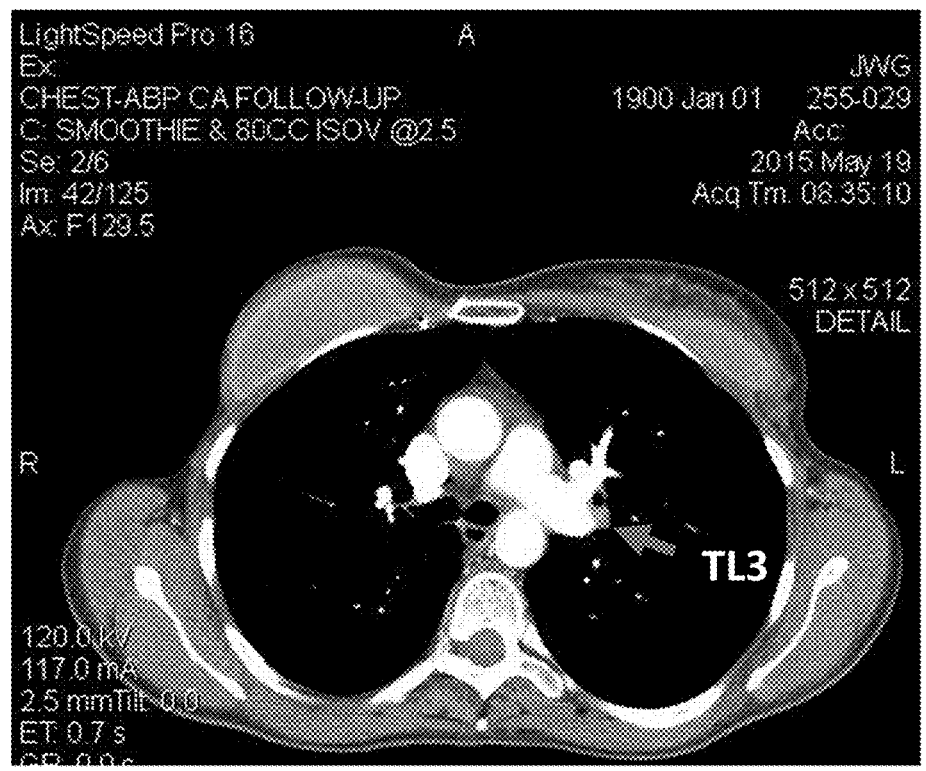

FIG. 5

| Patient ID | Age | Sex | # of Prior Tx | CPI | # line CPI | Response to CPI | Duration of treatment with CPI (mos) | IMMU-132 Doses | IMMU-132 best response | Best % change TL | Histo | PFS (mo) |
|---|---|---|---|---|---|---|---|---|---|---|---|---|
| 181-047 | 78 | M | 2 | Nivolumab | 2 | Yes | 8 | 9 | SD | 0 | SQ | 1.2+ |
| 252-011 | 63 | F | 6 | Nivolumab | 2 | Not specified | 1 | 5 | SDc | 7 | AC | 3.7+ |
| 254-046 | 77 | F | 1 | Atezolizumab | 1 | Yes | 23 | 4 | SD | -13 | AC | 1.8+ |
| 255-061 | 61 | M | 6 | Atezolizumab | 4 | No | 3 | 10 | SDc | -23 | AC | 3.1+ |
| 255-065 | 66 | F | 2 | Nivolumab | 2 | No | 9 | 6 | SDc | -28 | AC | 2.7+ |
| 255-069 | 69 | M | 3 | Atezolizumab | 3 | No | 2 | 6 | SD | 1 | AC | 1.6+ |
| 255-072 | 74 | M | 3 | Nivolumab | 3 | No | 6 | 5 | PR | -50 | SQ | 2.0+ |
| 255-073 | 67 | F | 3 | Nivolumab | 3 | No | 5 | 6 | SD | 10 | AC | 1.9+ |

SEQUENCE LISTING

<160> NUMBER OF SEQ ID NOS: 20

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1

Lys Ala Ser Gln Asp Val Ser Ile Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Tyr Arg Tyr Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln His Tyr Ile Thr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Tyr Gly Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Thr Tyr Thr Gly Glu Pro Thr Tyr Thr Asp Asp Phe Lys
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Phe Gly Ser Ser Tyr Trp Tyr Phe Asp Val
1               5                   10

<210> SEQ ID NO 7
```

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 8
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ile Glu Tyr Leu Ala Lys Gln Ile Val Asp Asn Ala Ile Gln Gln
1               5                   10                  15

Ala

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 11
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 11

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 12
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 14
<211> LENGTH: 51
<212> TYPE: PRT
<213> ORGANISM: Homo sapiens

<400> SEQUENCE: 14

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 15
<211> LENGTH: 54
<212> TYPE: PRT

<213> ORGANISM: Homo sapiens

<400> SEQUENCE: 15

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
        50

<210> SEQ ID NO 16
<211> LENGTH: 44
<212> TYPE: PRT
<213> ORGANISM: Homo sapiens

<400> SEQUENCE: 16

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 17
<211> LENGTH: 44
<212> TYPE: PRT
<213> ORGANISM: Homo sapiens

<400> SEQUENCE: 17

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 18
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                     150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Leu Ala Leu
1
```

EFFICACY OF ANTI-TROP-2-SN-38 ANTIBODY DRUG CONJUGATES FOR THERAPY OF TUMORS RELAPSED/REFRACTORY TO CHECKPOINT INHIBITORS

RELATED APPLICATIONS

This application claims the benefit under 35 U.S.C. 119(e) of U.S. Provisional Patent Application 62/328,289, filed Apr. 27, 2016, the entire text of which is incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 5, 2017, is named IMM366US2_SL.txt. and is 13,002 bytes in size.

FIELD OF THE INVENTION

The present invention relates to therapeutic use of antibody-drug conjugates (ADCs) comprising anti-Trop-2 antibodies or antigen-binding fragments thereof and camptothecins, such as SN-38, with improved ability to target various cancer cells in human subjects. In preferred embodiments, the antibodies and therapeutic moieties are linked via an intracellularly-cleavable linkage that increases therapeutic efficacy. In more preferred embodiments, the ADCs are administered at specific dosages and/or specific schedules of administration that optimize the therapeutic effect. Surprisingly, the optimized dosages and schedules of administration of SN-38-conjugated antibodies, such as sacituzumab govitecan, show unexpected superior efficacy that could not have been predicted from animal model studies, allowing effective treatment of cancers that are resistant to checkpoint inhibitor antibodies such as atezolizumab, pembrolizumab, nivolumab, pidilizumab, durvalumab, atezolizumab, ipilimumab or tremelimumab. In specific embodiments, the ADC may be administered to a human subject with a Trop-2 positive cancer at a dosage of between 3 and 18 mg/kg, more preferably between 4 and 12 mg/kg, most preferably between 8 and 10 mg/kg. Surprisingly, the anti-Trop-2-SN38 antibody drug conjugates (ADCs) are effective to treat Trop-2 positive cancers in patients who had relapsed from or shown resistance to checkpoint inhibitor therapy, such as pancreatic cancer, triple-negative breast cancer, small cell lung cancer, endometrial cancer, urothelial cancer and non-small cell lung cancer.

BACKGROUND OF THE INVENTION

For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed, but have had mixed success in the therapy of cancer in humans, and virtually no application in other diseases, such as infectious and autoimmune diseases. The toxic agent is most commonly a chemotherapeutic drug, although particle-emitting radionuclides, or bacterial or plant toxins, have also been conjugated to MAbs, especially for the therapy of cancer (Sharkey and Goldenberg, CA Cancer J Clin. 2006 July-August; 56(4):226-243) and, more recently, with radioimmunoconjugates for the preclinical therapy of certain infectious diseases (Dadachova and Casadevall, Q J Nucl Med Mol Imaging 2006; 50(3):193-204).

The advantages of using MAb-chemotherapeutic drug conjugates are that (a) the chemotherapeutic drug itself is structurally well defined; (b) the chemotherapeutic drug is linked to the MAb protein using very well-defined conjugation chemistries, often at specific sites remote from the MAbs' antigen binding regions; (c) MAb-chemotherapeutic drug conjugates can be made more reproducibly and usually with less immunogenicity than chemical conjugates involving MAbs and bacterial or plant toxins, and as such are more amenable to commercial development and regulatory approval; and (d) the MAb-chemotherapeutic drug conjugates are orders of magnitude less toxic systemically than radionuclide MAb conjugates, particularly to the radiation-sensitive bone marrow.

Camptothecin (CPT) and its derivatives are a class of potent antitumor agents. Irinotecan (also referred to as CPT-11) and topotecan are CPT analogs that are approved cancer therapeutics (Iyer and Ratain, Cancer Chemother. Phamacol. 42: S31-S43 (1998)). CPTs act by inhibiting topoisomerase I enzyme by stabilizing topoisomerase I-DNA complex (Liu, et al. in The Camptothecins: Unfolding Their Anticancer Potential, Liehr J. G., Giovanella, B. C. and Verschraegen (eds), NY Acad Sci., NY 922:1-10 (2000)). CPTs present specific issues in the preparation of conjugates. One issue is the insolubility of most CPT derivatives in aqueous buffers. Second, CPTs provide specific challenges for structural modification for conjugating to macromolecules. For instance, CPT itself contains only a tertiary hydroxyl group in ring-E. The hydroxyl functional group in the case of CPT must be coupled to a linker suitable for subsequent protein conjugation; and in potent CPT derivatives, such as SN-38, the active metabolite of the chemotherapeutic CPT-11, and other C-10-hydroxyl-containing derivatives such as topotecan and 10-hydroxy-CPT, the presence of a phenolic hydroxyl at the C-10 position complicates the necessary C-20-hydroxyl derivatization. Third, the lability under physiological conditions of the δ-lactone moiety of the E-ring of camptothecins results in greatly reduced antitumor potency. Therefore, the conjugation protocol is performed such that it is carried out at a pH of 7 or lower to avoid the lactone ring opening. However, conjugation of a bifunctional CPT possessing an amine-reactive group such as an active ester would typically require a pH of 8 or greater. Fourth, an intracellularly-cleavable moiety preferably is incorporated in the linker/spacer connecting the CPTs and the antibodies or other binding moieties.

A need exists for more effective methods of preparing and administering antibody-CPT conjugates, such as anti-Trop-2-SN-38 conjugates (e.g., sacituzumab govitecan). Preferably, the methods comprise optimized dosing and administration schedules that maximize efficacy and minimize toxicity, for use in patients with Trop-2 positive cancers that are relapsed from or resistant to checkpoint inhibitor antibodies.

SUMMARY OF THE INVENTION

As used herein, the abbreviation "CPT" may refer to camptothecin or any of its derivatives, such as SN-38, unless expressly stated otherwise. The present invention resolves an unfulfilled need in the art by providing improved methods and compositions for preparing and administering CPT-antibody ADCs. Preferably, the camptothecin is SN-38 and the antibody is an anti-Trop-2 antibody (e.g., sacituzumab govitecan). The disclosed methods and compositions are of use for the treatment of diseases which are refractory or less responsive to other forms of therapy, such as Trop-2+ cancers that are resistant to or relapsed from treatment with checkpoint inhibitor antibodies.

Preferably, the antibody moiety of the ADC is a monoclonal antibody, antibody fragment, bispecific or other multivalent antibody, or other antibody-based molecule or compound. The antibody can be of various isotypes, preferably human IgG1, IgG2, IgG3 or IgG4, more preferably comprising human IgG1 hinge and constant region sequences. The antibody or fragment thereof can be a chimeric human-mouse, a chimeric human-primate, a humanized (human framework and murine hypervariable (CDR) regions), or fully human antibody, as well as variations thereof, such as half-IgG4 antibodies (referred to as "unibodies"), as described by van der Neut Kolfschoten et al. (*Science* 2007; 317:1554-1557). More preferably, the antibody or fragment thereof may be designed or selected to comprise human constant region sequences that belong to specific allotypes, which may result in reduced immunogenicity when the ADC is administered to a human subject. Preferred allotypes for administration include a non-G1 ml allotype (nG1m1), such as G1m3, G1m3,1, G1m3,2 or G1m3,1,2. More preferably, the allotype is selected from the group consisting of the nG1m1, G1m3, nG1 m1,2 and Km3 allotypes.

An exemplary anti-Trop-2 antibody is a humanized RS7 (hRS7) antibody, comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDD-FKG, SEQ ID NO:5) and CDR3 (GGFGSSYWYFDV, SEQ ID NO:6).

In a preferred embodiment, the chemotherapeutic moiety is selected from camptothecin (CPT) and its analogs and derivatives and is more preferably SN-38. However, other chemotherapeutic moieties that may be utilized include taxanes (e.g, baccatin III, taxol), epothilones, anthracyclines (e.g., doxorubicin (DOX), epirubicin, morpholinodoxorubicin (morpholino-DOX), cyanomorpholino-doxorubicin (cyanomorpholino-DOX), 2-pyrrolinodoxorubicin (2-PDOX) or a prodrug form of 2-PDOX (pro-2-PDOX); see, e.g., Priebe W (ed.), ACS symposium series 574, published by American Chemical Society, Washington D.C., 1995 (332 pp) and Nagy et al., *Proc. Natl. Acad. Sci. USA* 93:2464-2469, 1996), benzoquinoid ansamycins exemplified by geldanamycin (DeBoer et al., *Journal of Antibiotics* 23:442-447, 1970; Neckers et al., *Invest. New Drugs* 17:361-373, 1999), and the like. Preferably, the antibody or fragment thereof links to at least one chemotherapeutic moiety; preferably 1 to about 5 chemotherapeutic moieties; more preferably 6 or more chemotherapeutic moieties, most preferably about 6 to about 12 chemotherapeutic moieties.

Various embodiments may concern use of the subject methods and compositions to treat cancers that express human Trop-2, including but not limited to carcinomas such as carcinomas of the esophagus, pancreas, lung, stomach, colon and rectum, urinary bladder, breast, ovary, uterus, kidney, urothelium and prostate.

In certain embodiments involving treatment of cancer, the drug conjugates may be used in combination with surgery, radiation therapy, chemotherapy, immunotherapy with naked antibodies, radioimmunotherapy, immunomodulators, vaccines, and the like. These combination therapies can allow lower doses of each therapeutic to be given in such combinations, thus reducing certain severe side effects, and potentially reducing the courses of therapy required. When there is no or minimal overlapping toxicity, ful doses of each can also be given. In alternative embodiments, the ADCs may be administered in combination with an interferon, a checkpoint inhibitor antibody, a Bruton tyrosine kinase inhibitor, a PI3K inhibitor, a PARP inhibitor or a microtubule inhibitor, as discussed below.

Preferred optimal dosing of ADCs may include an i.v. dosage of between 3 mg/kg and 18 mg/kg, preferably given either weekly, twice weekly or every other week. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. Exemplary dosages of use may include 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, and 18 mg/kg. Preferred dosages are 4, 6, 8, 9, 10, or 12 mg/kg.

In certain alternative embodiments, where the ADC is administered subcutaneously, dosages of ADCs such as sacituzumab govitecan (IMMU-132) may be limited by the ability to concentrate the ADC without precipitation or aggregation, as well as the volume of administration that may be given subcutaneously (preferably, 1, 2, or 3 ml or less). Consequently, for subcutaneous administration the ADC may be given at 1.5 to 4 mg/kg, given daily for 1 week, or 3 times weekly for 2 weeks, or twice weekly for two weeks, followed by rest. Where multiple sites of s.c. injection are used, dosages of up to 8 mg/kg may be provided. Maintenance doses of ADC may be administered i.v. or s.c. every two to three weeks or monthly after induction. Alternatively, induction may occur with two to four cycles of i.v. administration at 8-10 mg/kg (each cycle with ADC administration on Days 1 and 8 of two 21-day cycles with a one-week rest period in between), followed by s.c. administration as active dosing one or more times weekly or as maintenance therapy. Dosing may be adjusted based on interim tumor scans and/or by analysis of Trop-2 positive circulating tumor cells.

The person of ordinary skill will realize that a variety of factors, such as age, general health, specific organ function or weight, as well as effects of prior therapy on specific organ systems (e.g., bone marrow) may be considered in selecting an optimal dosage of ADC, and that the dosage and/or frequency of administration may be increased or decreased during the course of therapy. The dosage may be repeated as needed, with evidence of tumor shrinkage observed after as few as 4 to 8 doses. The optimized dosages and schedules of administration disclosed herein show unexpected superior efficacy and reduced toxicity in human subjects, which could not have been predicted from animal model studies. Surprisingly, the superior efficacy allows treatment of tumors that were previously found to be resistant to one or more standard anti-cancer therapies, including checkpoint inhibitor therapy.

The subject methods may include use of CT and/or PET/CT, or MRI, to measure tumor response at regular intervals. Blood levels of tumor markers, such as CEA (carcinoembryonic antigen), CA19-9, AFP, CA 15.3, or PSA, may also be monitored. Dosages and/or administration schedules may be adjusted as needed, according to the results of imaging and/or marker blood levels.

A surprising result with the instant claimed compositions and methods is the unexpected tolerability of high doses of antibody-drug conjugate, even with repeated infusions, with only relatively low-grade toxicities of nausea and vomiting observed, or manageable neutropenia. A further surprising result is the lack of accumulation of the antibody-drug conjugate, unlike other products that have conjugated SN-38 to albumin, PEG or other carriers. The lack of accumulation is associated with improved tolerability and lack of serious toxicity even after repeated or increased dosing. These surprising results allow optimization of dosage and delivery schedule, with unexpectedly high efficacies and low toxicities. The claimed methods provide for shrinkage of solid tumors, in individuals with previously resistant cancers, of 15% or more, preferably 20% or more, preferably 30% or more, more preferably 40% or more in size (as measured by longest diameter). The person of ordinary skill will realize that tumor size may be measured by a variety of different techniques, such as total tumor volume, maximal tumor size in any dimension or a combination of size measurements in several dimensions. This may be with standard radiological procedures, such as computed tomography, ultrasonography, and/or positron-emission tomography. The means of measuring size is less important than observing a trend of decreasing tumor size with ADC treatment, preferably resulting in elimination of the tumor.

While the ADC may be administered as a periodic bolus injection, in alternative embodiments the ADC may be administered by continuous infusion of antibody-drug conjugates. In order to increase the Cmax and extend the PK of the ADC in the blood, a continuous infusion may be administered for example by indwelling catheter. Such devices are known in the art, such as HICKMAN®, BROVIAC® or PORT-A-CATH® catheters (see, e.g., Skolnik et al., *Ther Drug Monit* 32:741-48, 2010) and any such known indwelling catheter may be used. A variety of continuous infusion pumps are also known in the art and any such known infusion pump may be used. The dosage range for continuous infusion may be between 0.1 and 3.0 mg/kg per day. More preferably, these ADCs can be administered by intravenous infusions over relatively short periods of 2 to 5 hours, more preferably 2-3 hours.

In particularly preferred embodiments, the ADCs and dosing schedules may be efficacious in patients resistant to standard therapies. For example, the anti-Trop-2 sacituzumab govitecan may be administered to a patient who has not responded to prior therapy with irinotecan, the parent agent of SN-38. Surprisingly, the irinotecan-resistant patient may show a partial or even a complete response to sacituzumab govitecan. The ability of the ADC to specifically target the tumor tissue may overcome tumor resistance by improved targeting and enhanced delivery of the therapeutic agent. The ADCs may show similar improved efficacy and/or decreased toxicity, compared to alternative standard therapeutic treatments such as checkpoint inhibitor antibodies.

A specific preferred subject may be a metastatic colorectal cancer patient, metastatic pancreatic cancer patient, a triple-negative breast cancer patient, a HER+, ER+, progesterone+ breast cancer patient, a metastatic non-small-cell lung cancer (NSCLC) patient, a metastatic small-cell lung cancer patient, a metastatic stomach cancer patient, a metastatic renal cancer patient, a metastatic urothelial cancer patient, a metastatic urinary bladder cancer patient, a metastatic ovarian cancer patient, or a metastatic uterine cancer patient.

BRIEF DESCRIPTION OF THE DRAWINGS

FIG. 1. Summary of CT scan results for patient with checkpoint inhibitor resistant metastatic TNBC, treated with 10 mg/kg sacituzumab govitecan.

FIG. 3. Comparison of CT scans for target lesions 1 and 2, before and after treatment with 10 mg/kg sacituzumab govitecan (IMMU-132). Baseline image is shown on top and second response assessment after sacituzumab govitecan therapy is shown on the bottom. Shrinkage of tumors induced by IMMU-132 was clearly observed.

FIG. 4. Comparison of CT scans for target lesion 3, before and after treatment with 10 mg/kg sacituzumab govitecan (IMMU-132). Baseline image is shown on top and second response assessment after sacituzumab govitecan therapy is shown on the bottom. Shrinkage of tumor induced by IMMU-132 was clearly observed.

FIG. 5. Summary of results for patients with checkpoint inhibitor resistant tumors treated with IMMU-132.

DETAILED DESCRIPTION OF THE INVENTION

Definitions

Figure 2:
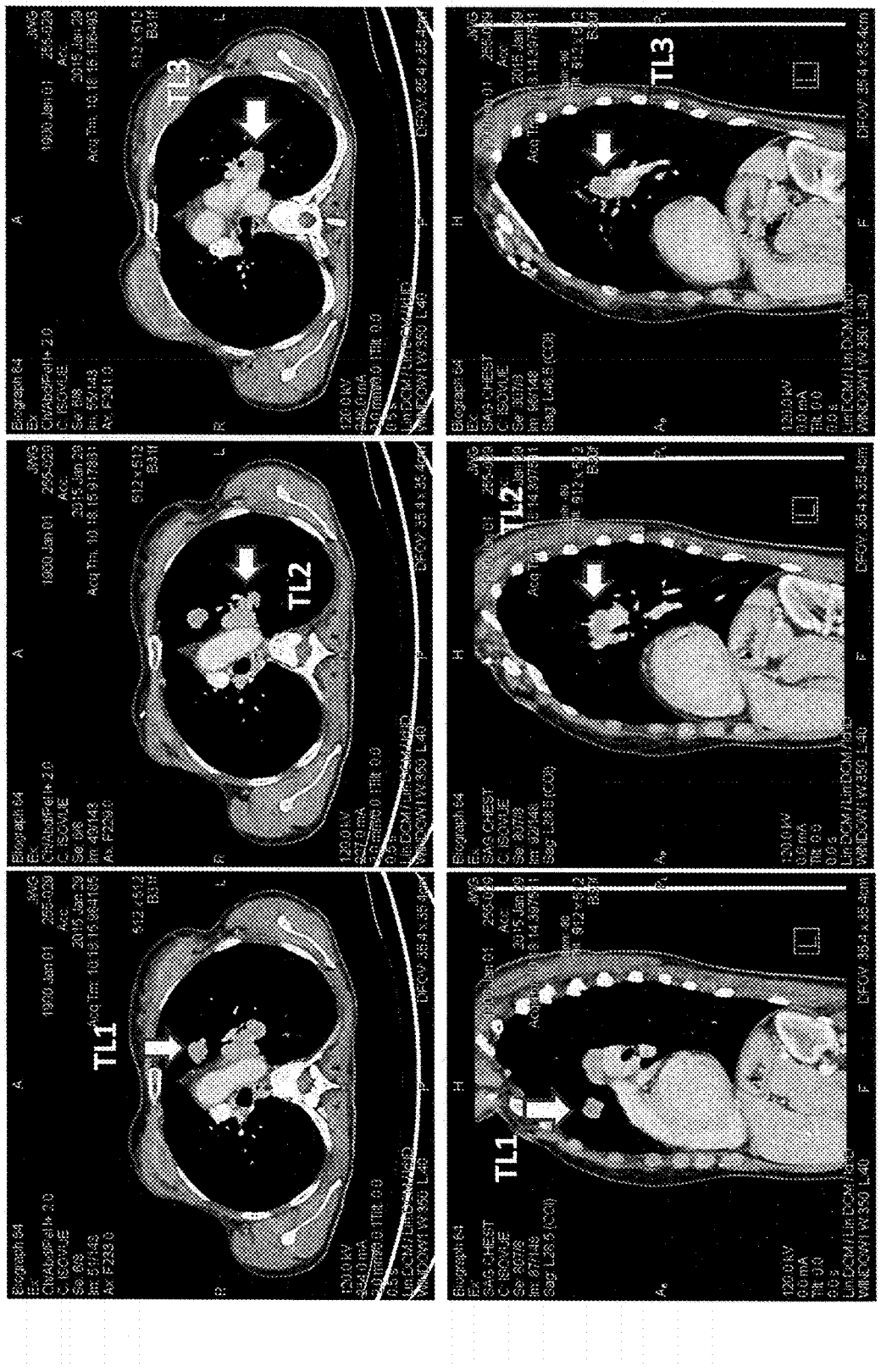
FIG. 2. Baseline CT images for patient with checkpoint inhibitor resistant metastatic TNBC, showing axial images (top row) and sagittal images (bottom row). Tumors are indicated by arrows.

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

The term about is used herein to mean plus or minus ten percent (10%) of a value. For example, "about 100" refers to any number between 90 and 110.

An antibody, as used herein, refers to a full-length (i.e., naturally occurring or formed by normal immunoglobulin gene fragment recombinatorial processes) immunoglobulin molecule (e.g., an IgG antibody) or an antigen-binding portion of an immunoglobulin molecule, such as an antibody fragment. An antibody or antibody fragment may be conjugated or otherwise derivatized within the scope of the claimed subject matter. Such antibodies include but are not limited to IgG1, IgG2, IgG3, IgG4 (and IgG4 subforms), as well as IgA isotypes. As used below, the abbreviation "MAb" may be used interchangeably to refer to an antibody, antibody fragment, monoclonal antibody or multispecific antibody.

An antibody fragment is a portion of an antibody such as F(ab')$_2$, F(ab)$_2$, Fab', Fab, Fv, scFv (single chain Fv), single domain antibodies (DABS or VHHs) and the like, including the half-molecules of IgG4 cited above (van der Neut Kolfschoten et al. (Science 2007; 317(14 September):1554-1557). Regardless of structure, an antibody fragment of use binds with the same antigen that is recognized by the intact antibody. The term "antibody fragment" also includes synthetic or genetically engineered proteins that act like an antibody by binding to a specific antigen to form a complex. For example, antibody fragments include isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). The fragments may be constructed in different ways to yield multivalent and/or multispecific binding forms.

A naked antibody is generally an entire antibody that is not conjugated to a therapeutic agent. A naked antibody may exhibit therapeutic and/or cytotoxic effects, for example by Fc-dependent functions, such as complement fixation (CDC) and ADCC (antibody-dependent cell cytotoxicity). However, other mechanisms, such as apoptosis, anti-angiogenesis, anti-metastatic activity, anti-adhesion activity, inhibition of heterotypic or homotypic adhesion, and interference in signaling pathways, may also provide a therapeutic effect. Naked antibodies include polyclonal and monoclonal antibodies, naturally occurring or recombinant antibodies, such as chimeric, humanized or human antibodies and fragments thereof. In some cases a "naked antibody" may also refer to a "naked" antibody fragment. As defined herein, "naked" is synonymous with "unconjugated," and means not linked or conjugated to a therapeutic agent.

A chimeric antibody is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a primate, cat or dog.

A humanized antibody is a recombinant protein in which the CDRs from an antibody from one species; e.g., a murine antibody, are transferred from the heavy and light variable chains of the murine antibody into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody.

A human antibody is an antibody obtained, for example, from transgenic mice that have been "engineered" to produce human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for various antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, human antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, the Examples section of each of which is incorporated herein by reference.

A therapeutic agent is an atom, molecule, or compound that is useful in the treatment of a disease. Examples of therapeutic agents include, but are not limited to, antibodies, antibody fragments, immunoconjugates, drugs, cytotoxic agents, pro-apopoptotic agents, toxins, nucleases (including DNAses and RNAses), hormones, immunomodulators, chelators, boron compounds, photoactive agents or dyes, radionuclides, oligonucleotides, interference RNA, siRNA, RNAi, anti-angiogenic agents, chemotherapeutic agents, cyokines, chemokines, prodrugs, enzymes, binding proteins or peptides or combinations thereof.

An immunoconjugate is an antibody, antigen-binding antibody fragment, antibody complex or antibody fusion protein that is conjugated to a therapeutic agent. Conjugation may be covalent or non-covalent. Preferably, conjugation is covalent. Where the therapeutic agent is a drug, the resulting immunoconjugate is an antibody-drug conjugate or ADC.

As used herein, the term antibody fusion protein is a recombinantly-produced antigen-binding molecule in which one or more natural antibodies, single-chain antibodies or antibody fragments are linked to another moiety, such as a protein or peptide, a toxin, a cytokine, a hormone, etc. In certain preferred embodiments, the fusion protein may comprise two or more of the same or different antibodies, antibody fragments or single-chain antibodies fused together, which may bind to the same epitope, different epitopes on the same antigen, or different antigens.

An immunomodulator is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. However, in some cases an immunomodulator may suppress proliferation or activation of immune cells. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation. Exemplary interferons include interferon-$\alpha$, interferon-$\beta$, interferon-$\gamma$ and interferon-$\lambda$.

CPT is an abbreviation for camptothecin, and as used in the present application CPT represents camptothecin itself or an analog or derivative of camptothecin, such as SN-38. The structures of camptothecin and some of its analogs, with the numbering indicated and the rings labeled with letters A-E, are given in formula 1 in Chart 1 below.

Chart 1

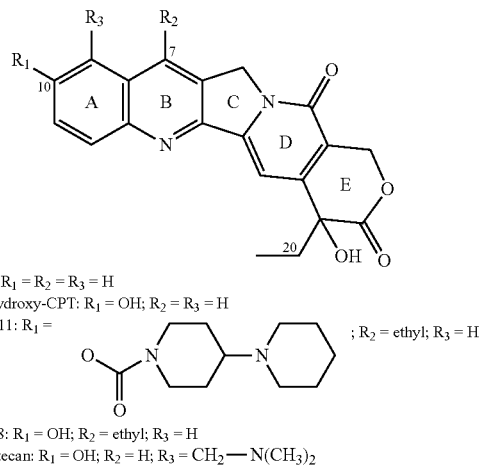

CPT: $R_1 = R_2 = R_3 = H$
10-Hydroxy-CPT: $R_1 = OH; R_2 = R_3 = H$
CPT-11: $R_1 = $ [structure]; $R_2 = $ ethyl; $R_3 = H$ SN-38: $R_1 = OH; R_2 = $ ethyl; $R_3 = H$
Topotecan: $R_1 = OH; R_2 = H; R_3 = CH_2-N(CH_3)_2$ Anti-Trop-2 Antibodies Various embodiments concern use of antibodies or fragments thereof that bind to Trop-2. In a specific preferred embodiment, the anti-Trop-2 antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6).

The RS7 antibody was a murine $IgG_1$ raised against a crude membrane preparation of a human primary squamous cell lung carcinoma. (Stein et al., Cancer Res. 50: 1330, 1990) The RS7 antibody recognizes a 46-48 kDa glycoprotein, characterized as cluster 13. (Stein et al., Int. J. Cancer Supp. 8:98-102, 1994) The antigen was designated as EGP-1 (epithelial glycoprotein-1), but is also referred to as Trop-2.

Trop-2 is a type-I transmembrane protein and has been cloned from both human (Fornaro et al., Int J Cancer 1995; 62:610-8) and mouse cells (Sewedy et al., Int J Cancer 1998; 75:324-30). The amino acid sequence of human Trop-2 is publicly known (see, e.g., NCBI Accession No. P09758.3). In addition to its role as a tumor-associated calcium signal transducer (Ripani et al., Int J Cancer 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5).

The growing interest in Trop-2 as a therapeutic target for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell (Fong et al., Modern Pathol 2008; 21:186-91) carcinomas. The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

Flow cytometry and immunohistochemical staining studies have shown that the RS7 MAb detects antigen on a variety of tumor types, with limited binding to normal human tissue (Stein et al., 1990). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., 1990; Stein et al., 1991).

Strong RS7 staining has been demonstrated in tumors from the lung, breast, bladder, ovary, uterus, stomach, and prostate. (Stein et al., Int. J. Cancer 55:938, 1993) The lung cancer cases comprised both squamous cell carcinomas and adenocarcinomas. (Stein et al., Int. J. Cancer 55:938, 1993) Both cell types stained strongly, indicating that the RS7 antibody does not distinguish between histologic classes of non-small-cell carcinoma of the lung.

The RS7 MAb is rapidly internalized into target cells (Stein et al., 1993). The internalization rate constant for RS7 MAb is intermediate between the internalization rate constants of two other rapidly internalizing MAbs, which have been demonstrated to be useful for ADC production. (Id.) It is well documented that internalization of ADCs is a requirement for anti-tumor activity. (Pastan et al., Cell 47:641, 1986) Internalization of drug ADCs has been described as a major factor in anti-tumor efficacy. (Yang et al., Proc. Nat'l Acad. Sci. USA 85: 1189, 1988) Thus, the RS7 antibody exhibits several important properties for therapeutic applications.

While the hRS7 antibody is preferred, other anti-Trop-2 antibodies are known and/or publicly available and in alternative embodiments may be utilized in the subject ADCs. While humanized or human antibodies are preferred for reduced immunogenicity, in alternative embodiments a chimeric antibody may be of use. As discussed below, methods of antibody humanization are well known in the art and may be utilized to convert an available murine or chimeric antibody into a humanized form.

Anti-Trop-2 antibodies are commercially available from a number of sources and include LS-C126418, LS-C178765, LS-C126416, LS-C126417 (LifeSpan BioSciences, Inc., Seattle, Wash.); 10428-MM01, 10428-MM02, 10428-R001, 10428-R030 (Sino Biological Inc., Beijing, China); MR54 (eBioscience, San Diego, Calif.); sc-376181, sc-376746, Santa Cruz Biotechnology (Santa Cruz, Calif.); MM0588-49D6, (Novus Biologicals, Littleton, Colo.); ab79976, and ab89928 (ABCAM®, Cambridge, Mass.).

Other anti-Trop-2 antibodies have been disclosed in the patent literature. For example, U.S. Publ. No. 2013/0089872 discloses anti-Trop-2 antibodies K5-70 (Accession No. FERM BP-11251), K5-107 (Accession No. FERM BP-11252), K5-116-2-1 (Accession No. FERM BP-11253), T6-16 (Accession No. FERM BP-11346), and T5-86 (Accession No. FERM BP-11254), deposited with the International Patent Organism Depositary, Tsukuba, Japan. U.S. Pat. No. 5,840,854 disclosed the anti-Trop-2 monoclonal antibody BR110 (ATCC No. HB11698). U.S. Pat. No. 7,420,040 disclosed an anti-Trop-2 antibody produced by hybridoma cell line AR47A6.4.2, deposited with the IDAC (International Depository Authority of Canada, Winnipeg, Canada) as accession number 141205-05. U.S. Pat. No. 7,420,041 disclosed an anti-Trop-2 antibody produced by hybridoma cell line AR52A301.5, deposited with the IDAC as accession number 141205-03. U.S. Publ. No. 2013/0122020 disclosed anti-Trop-2 antibodies 3E9, 6G11, 7E6, 15E2, 18B1. Hybridomas encoding a representative antibody were deposited with the American Type Culture Collection (ATCC), Accession Nos. PTA-12871 and PTA-12872. ADC PF 06263507, comprising an anti-5T4 (anti-Trop-2) antibody attached to the tubulin inhibitor monomethylauristatin F (MMAF) is available from Pfizer, Inc. (Groton, Conn.) (see, e.g., Sapra et al., 2013, Mol Cancer Ther 12:38-47). U.S. Pat. No. 8,715,662 discloses anti-Trop-2 antibodies produced by hybridomas deposited at the AID-ICLC (Genoa, Italy) with deposit numbers PD 08019, PD 08020 and PD 08021. U.S. Patent Application Publ. No. 20120237518 discloses anti-Trop-2 antibodies 77220, KM4097 and KM4590. U.S. Pat. No. 8,309,094 (Wyeth) discloses antibodies A1 and A3, identified by sequence listing. The Examples section of each patent or patent application cited above in this paragraph is incorporated herein by reference. Non-patent publication Lipinski et al. (1981, Proc Natl. Acad Sci USA, 78:5147-50) disclosed anti-Trop-2 antibodies 162-25.3 and 162-46.2.

Numerous anti-Trop-2 antibodies are known in the art and/or publicly available. As discussed below, methods for preparing antibodies against known antigens were routine in the art. Methods for producing humanized, human or chimeric antibodies were also known. The person of ordinary skill, reading the instant disclosure in light of general knowledge in the art, would have been able to make and use the genus of anti-Trop-2 antibodies in the subject ADCs.

Use of antibodies against targets related to Trop-2 has been disclosed for immunotherapeutics other than ADCs. The murine anti-Trop-1 IgG2a antibody edrecolomab (PAN-OREX®) has been used for treatment of colorectal cancer, although the murine antibody is not well suited for human clinical use (Baeuerle & Gires, 2007, Br. J Cancer 96:417-423). Low-dose subcutaneous administration of ecrecolomab was reported to induce humoral immune responses against the vaccine antigen (Baeuerle & Gires, 2007). Adecatumumab (MT201), a fully human anti-Trop-1 antibody, has been used in metastatic breast cancer and early-stage prostate cancer and is reported to act through ADCC and CDC activity (Baeuerle & Gires, 2007). MT110, a single-chain anti-Trop-1/anti-CD3 bispecific antibody construct has reported efficacy against ovarian cancer (Baeuerle & Gires, 2007). Proxinium, an immunotoxin comprising anti-Trop-1 single-chain antibody fused to *Pseudomonas* exotoxin, has been tested in head-and-neck and bladder cancer (Baeuerle & Gires, 2007). None of these studies contained any disclosure of the use of anti-Trop-2 ADCs, particularly in patients resistant to treatment with checkpoint inhibitor antibodies.

Camptothecin Conjugates

Non-limiting methods and compositions for preparing ADCs comprising a camptothecin therapeutic agent attached to an antibody or antigen-binding antibody fragment are described below. In preferred embodiments, the solubility of the drug is enhanced by placing a defined polyethyleneglycol (PEG) moiety (i.e., a PEG containing a defined number of monomeric units) between the drug and the antibody, wherein the defined PEG is a low molecular weight PEG, preferably containing 1-30 monomeric units, more preferably containing 1-12 monomeric units.

Preferably, a first linker connects the drug at one end and may terminate with an acetylene or an azide group at the other end. This first linker may comprise a defined PEG moiety with an azide or acetylene group at one end and a different reactive group, such as carboxylic acid or hydroxyl group, at the other end. Said bifunctional defined PEG may be attached to the amine group of an amino alcohol, and the hydroxyl group of the latter may be attached to the hydroxyl group on the drug in the form of a carbonate. Alternatively, the non-azide (or acetylene) moiety of said defined bifunctional PEG is optionally attached to the N-terminus of an L-amino acid or a polypeptide, with the C-terminus attached to the amino group of amino alcohol, and the hydroxy group of the latter is attached to the hydroxyl group of the drug in the form of carbonate or carbamate, respectively.

A second linker, comprising an antibody-coupling group and a reactive group complementary to the azide (or acetylene) group of the first linker, namely acetylene (or azide), may react with the drug-(first linker) conjugate via acetylene-azide cycloaddition reaction to furnish a final bifunctional drug product that is useful for conjugating to disease-targeting antibodies. The antibody-coupling group is preferably either a thiol or a thiol-reactive group.

Methods for selective regeneration of the 10-hydroxyl group in the presence of the C-20 carbonate in preparations of drug-linker precursor involving CPT analogs such as SN-38 are provided below. Other protecting groups for reactive hydroxyl groups in drugs such as the phenolic hydroxyl in SN-38, for example t-butyldimethylsilyl or t-butyldiphenylsilyl, may also be used, and these are deprotected by tetrabutylammonium fluoride prior to linking of the derivatized drug to an antibody-coupling moiety. The 10-hydroxyl group of CPT analogs is alternatively protected as an ester or carbonate, other than 'BOC', such that the bifunctional CPT is conjugated to an antibody without prior deprotection of this protecting group. The protecting group is readily deprotected under physiological pH conditions after the bioconjugate is administered.

In the acetylene-azide coupling, referred to as 'click chemistry', the azide part may be on L2 with the acetylene part on L3. Alternatively, L2 may contain acetylene, with L3 containing azide. 'Click chemistry' refers to a copper (+1)-catalyzed cycloaddition reaction between an acetylene moiety and an azide moiety (Kolb H C and Sharpless K B, *Drug Discov Today* 2003; 8: 1128-37), although alternative forms of click chemistry are known and may be used. Click chemistry takes place in aqueous solution at near-neutral pH conditions, and is thus amenable for drug conjugation. The advantage of click chemistry is that it is chemoselective, and complements other well-known conjugation chemistries such as the thiol-maleimide reaction.

While the present application focuses on use of antibodies or antibody fragments as targeting moieties, the skilled artisan will realize that where a conjugate comprises an antibody or antibody fragment, another type of targeting moiety, such as an aptamer, avimer, affibody or peptide ligand, may be substituted.

An exemplary preferred embodiment is directed to a conjugate of a drug derivative and an antibody of the general formula 2,

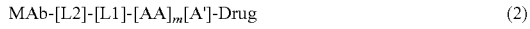

MAb-[L2]-[L1]-[AA]$_m$[A']-Drug  (2)

where MAb is a disease-targeting antibody; L2 is a component of the cross-linker comprising an antibody-coupling moiety and one or more of acetylene (or azide) groups; L1 comprises a defined PEG with azide (or acetylene) at one end, complementary to the acetylene (or azide) moiety in L2, and a reactive group such as carboxylic acid or hydroxyl group at the other end; AA is an L-amino acid; m is an integer with values of 0, 1, 2, 3, or 4; and A' is an additional spacer, selected from the group of ethanolamine, 4-hydroxybenzyl alcohol, 4-aminobenzyl alcohol, or substituted or unsubstituted ethylenediamine. The L amino acids of 'AA' are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. If the A' group contains hydroxyl, it is linked to the hydroxyl group or amino group of the drug in the form of a carbonate or carbamate, respectively.

In a preferred embodiment of formula 2, A' is a substituted ethanolamine derived from an L-amino acid, wherein the carboxylic acid group of the amino acid is replaced by a hydroxymethyl moiety. A' may be derived from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In an example of the conjugate of the preferred embodiment of formula 2, m is 0, A' is L-valinol, and the drug is exemplified by SN-38. The resultant structure is shown in formula 3.

removal of protecting groups at both lysine side chain and SN-38 gives the product of this example, shown in formula 3.

While not wishing to be bound by theory, the small MW SN-38 product, namely valinol-SN-38 carbonate, generated after intracellular proteolysis, has the additional pathway of liberation of intact SN-38 through intramolecular cyclization involving the amino group of valinol and the carbonyl of the carbonate.

In another preferred embodiment, A' of the general formula 2 is A-OH, whereby A-OH is a collapsible moiety such as 4-aminobenzyl alcohol or a substituted 4-aminobenzyl alcohol substituted with a $C_1$-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the antibody-binding group.

(3)

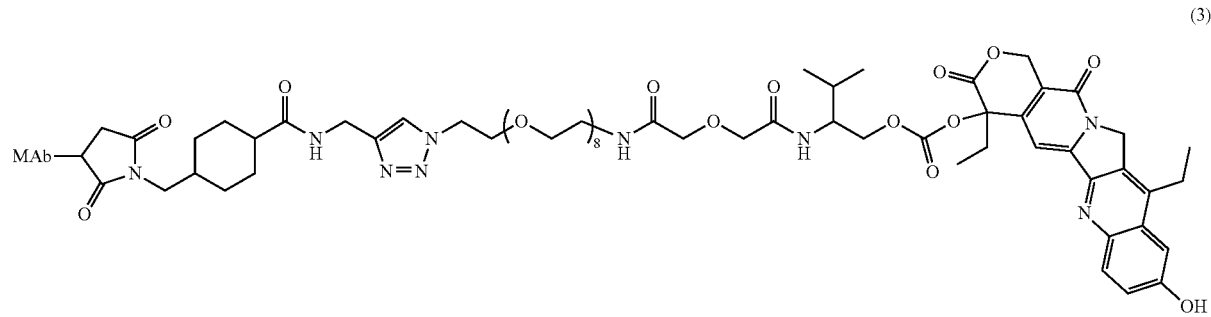

In another example of the conjugate of the preferred embodiment of formula 2, m is 1 and represented by a derivatized L-lysine, A' is L-valinol, and the drug is exemplified by SN-38. The structure is shown in formula 4.

An example of a preferred embodiment is given below, wherein the A-OH embodiment of A' of general formula (2) is derived from substituted 4-aminobenzyl alcohol, and 'AA' is comprised of a single L-amino acid with m=1 in the (4)

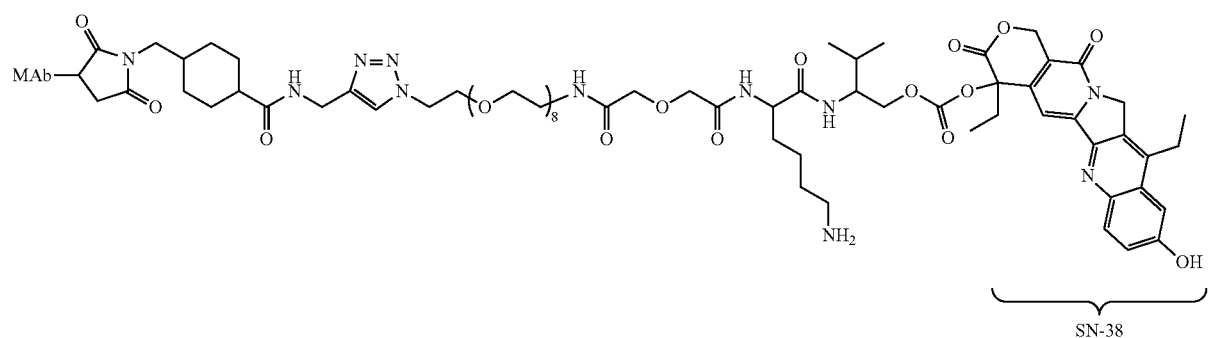

In this embodiment, an amide bond is first formed between the carboxylic acid of an amino acid such as lysine and the amino group of valinol, using orthogonal protecting groups for the lysine amino groups. The protecting group on the N-terminus of lysine is removed, keeping the protecting group on the side chain of lysine intact, and the N-terminus is coupled to the carboxyl group on the defined PEG with azide (or acetylene) at the other end. The hydroxyl group of valinol is then attached to the 20-chloroformate derivative of 10-hydroxy-protected SN-38, and this intermediate is coupled to an L2 component carrying the antibody-binding moiety as well as the complementary acetylene (or azide) group involved in the click cycloaddition chemistry. Finally, general formula (2), and the drug is exemplified with SN-38. The structure is represented below (formula 5, referred to as MAb-CLX-SN-38). Single amino acid of AA is selected from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The substituent R on 4-aminobenzyl alcohol moiety (A-OH embodiment of A') is hydrogen or an alkyl group selected from C1-C10 alkyl groups.

(5)

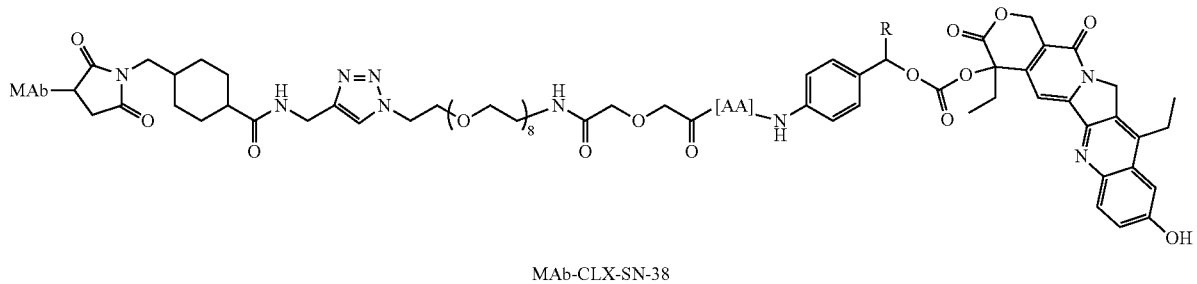

MAb-CLX-SN-38

A particularly preferred embodiment of MAb-CLX-SN-38 of formula 5, wherein the single amino acid AA is L-lysine and R=H, and the drug is exemplified by SN-38 (formula 6; referred to as MAb-CL2A-SN-38). The structure differs from the linker MAb-CL2-SN-38 in the substitution of a single lysine residue for a Phe-Lys dipeptide found in the CL2 linker. The Phe-Lys dipeptide was designed as a cathepsin B cleavage site for lysosomal enzyme, which was considered to be important for intracellular release of bound drug. Surprisingly, despite the elimination of the cathepsin-cleavage site, ADCs comprising a CL2A linker are at least as efficacious, and may be more efficacious in vivo than those comprising a CL2 linker the example of SN-38 as the drug, the more reactive 10-hydroxy group of the drug is derivatized leaving the 20-hydroxyl group unaffected. Within the general formula 2, A' is a substituted ethylenediamine. An example of this embodiment is represented by the formula '7' below, wherein the phenolic hydroxyl group of SN-38 is derivatized as a carbamate with a substituted ethylenediamine, with the other amine of the diamine derivatized as a carbamate with a 4-aminobenzyl alcohol, and the latter's amino group is attached to Phe-Lys dipeptide. In this structure (formula 7), R and R' are independently hydrogen or methyl. It is referred (6)

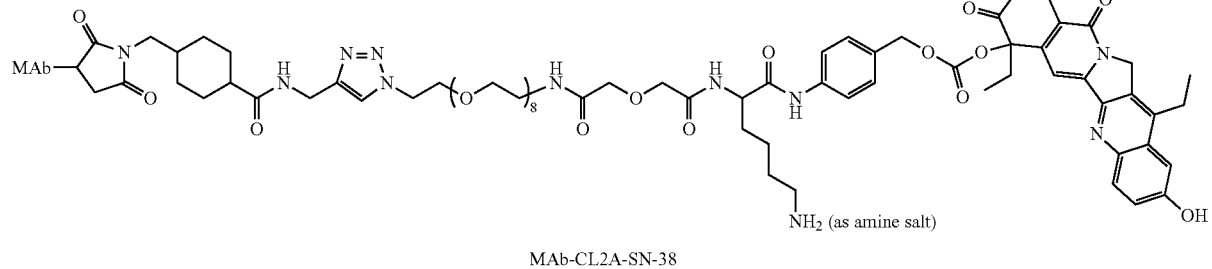

MAb-CL2A-SN-38

Other embodiments are possible within the context of 10-hydroxy-containing camptothecins, such as SN-38. In to as MAb-CL17-SN-38 or MAb-CL2E-SN-38, when R=R'=methyl.

(7)

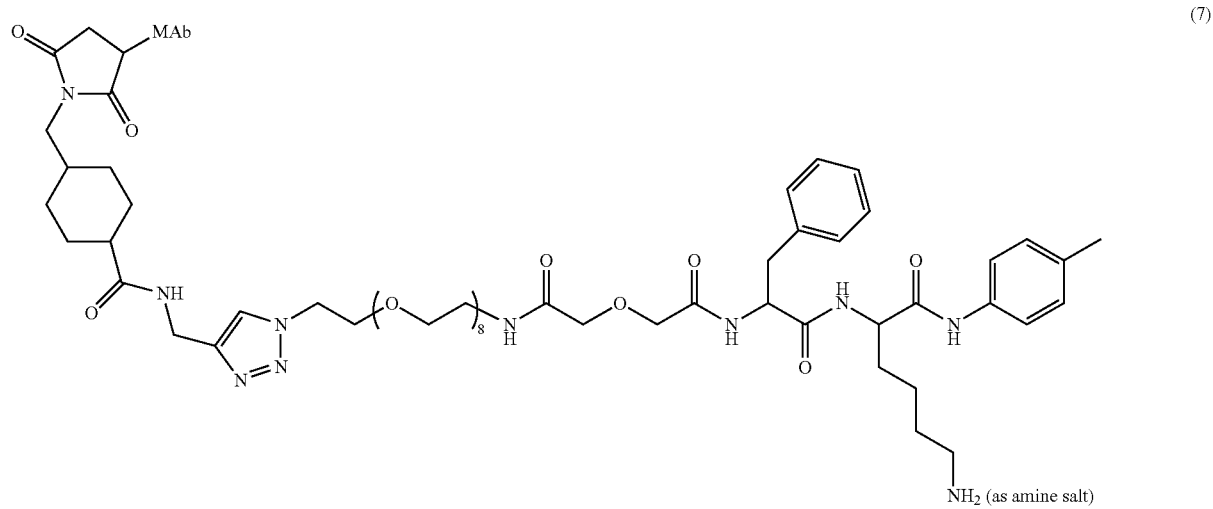

-continued

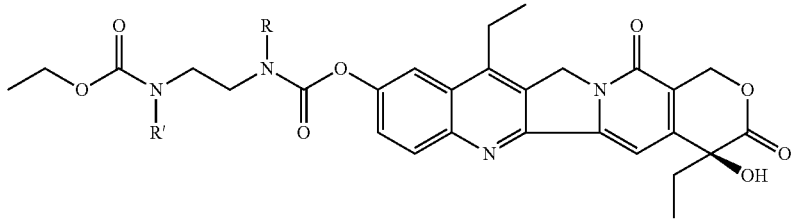

In certain embodiments, AA comprises a polypeptide moiety, preferably a di, tri or tetrapeptide, that is cleavable by intracellular peptidase. Examples are: Ala-Leu, Leu-Ala-Leu, and Ala-Leu-Ala-Leu (SEQ ID NO: 20) (Trouet et al., 1982). Another example is a Phe-Lys moiety that is cleavable by lysosomal cathepsin.

In a preferred embodiment, the L1 component of the conjugate contains a defined polyethyleneglycol (PEG) spacer with 1-30 repeating monomeric units. In a further preferred embodiment, PEG is a defined PEG with 1-12

In a preferred embodiment, L2 has a plurality of acetylene (or azide) groups, ranging from 2-40, but preferably 2-20, and more preferably 2-5, and a single antibody-binding moiety.

A representative SN-38 conjugate of an antibody containing multiple drug molecules and a single antibody-binding moiety is shown below. The 'L2' component of this structure is appended to 2 acetylenic groups, resulting in the attachment of two azide-appended SN-38 molecules. The bonding to MAb is represented as a succinimide.

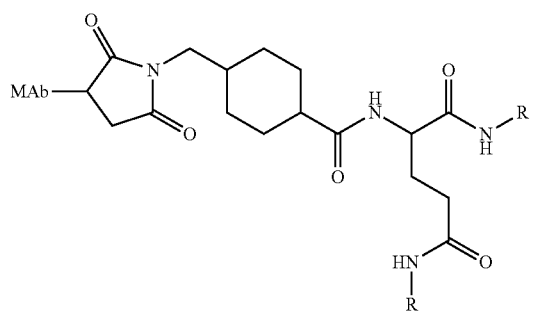

Where R residue is:

(9)

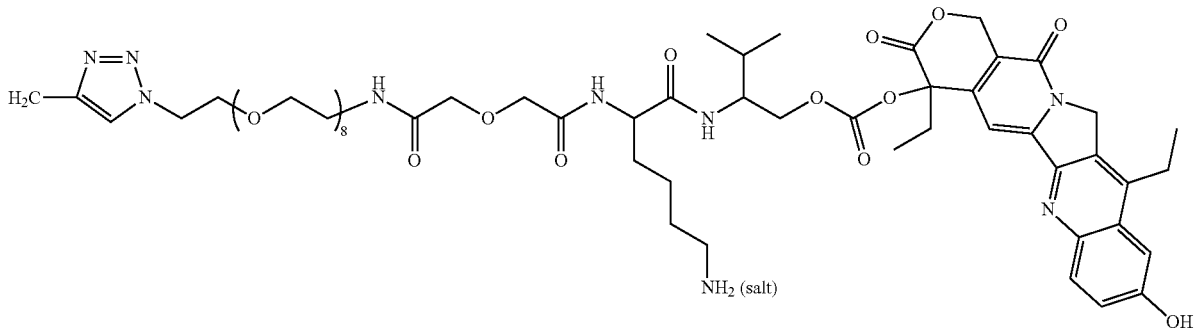

repeating monomeric units. The introduction of PEG may involve using heterobifunctionalized PEG derivatives which are available commercially. The heterobifunctional PEG may contain an azide or acetylene group. An example of a heterobifunctional defined PEG containing 8 repeating monomeric units, with 'NHS' being succinimidyl, is given below in formula 8:

(8)

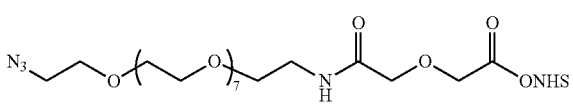

In preferred embodiments, when the bifunctional drug contains a thiol-reactive moiety as the antibody-binding group, the thiols on the antibody are generated on the lysine groups of the antibody using a thiolating reagent. Methods for introducing thiol groups onto antibodies by modifications of MAb's lysine groups are well known in the art (Wong in *Chemistry of protein conjugation and cross-linking*, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple drug moieties in the interchain region of the MAb away from the antigen-binding region. In a more preferred embodiment, attachment of SN-38 to reduced disulfide sulfhydryl groups results in formation of an antibody-SN-38 ADC with 6 SN-38 moieties covalently attached per antibody molecule. Other methods of providing cysteine residues for attachment of drugs or other therapeutic agents are known, such as the use of cysteine engineered antibodies (see U.S. Pat. No. 7,521,541, the Examples section of which is incorporated herein by reference.)

In alternative preferred embodiments, the chemotherapeutic moiety is selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), Pro-2PDOX, CPT, 10-hydroxy camptothecin, SN-38, topotecan, lurtotecan, 9-aminocamptothecin, 9-nitrocamptothecin, taxanes, geldanamycin, ansamycins, and epothilones. In a more preferred embodiment, the chemotherapeutic moiety is SN-38. Preferably, in the conjugates of the preferred embodiments, the antibody links to at least one chemotherapeutic moiety; preferably 1 to about 12 chemotherapeutic moieties; most preferably about 6 to about 12 chemotherapeutic moieties.

Furthermore, in a preferred embodiment, the linker component 'L2' comprises a thiol group that reacts with a thiol-reactive residue introduced at one or more lysine side chain amino groups of said antibody. In such cases, the antibody is pre-derivatized with a thiol-reactive group such as a maleimide, vinylsulfone, bromoacetamide, or iodoacetamide by procedures well described in the art.

In the context of this work, a process was surprisingly discovered by which CPT drug-linkers can be prepared wherein CPT additionally has a 10-hydroxyl group. This process involves, but is not limited to, the protection of the 10-hydroxyl group as a t-butyloxycarbonyl (BOC) derivative, followed by the preparation of the penultimate intermediate of the drug-linker conjugate. Usually, removal of BOC group requires treatment with strong acid such as trifluoroacetic acid (TFA). Under these conditions, the CPT 20-O-linker carbonate, containing protecting groups to be removed, is also susceptible to cleavage, thereby giving rise to unmodified CPT. In fact, the rationale for using a mildly removable methoxytrityl (MMT) protecting group for the lysine side chain of the linker molecule, as enunciated in the art, was precisely to avoid this possibility (Walker et al., 2002). It was discovered that selective removal of phenolic BOC protecting group is possible by carrying out reactions for short durations, optimally 3-to-5 minutes. Under these conditions, the predominant product was that in which the 'BOC' at 10-hydroxyl position was removed, while the carbonate at '20' position was intact.

An alternative approach involves protecting the CPT analog's 10-hydroxy position with a group other than 'BOC', such that the final product is ready for conjugation to antibodies without a need for deprotecting the 10-OH protecting group. The 10-hydroxy protecting group, which converts the 10-OH into a phenolic carbonate or a phenolic ester, is readily deprotected by physiological pH conditions or by esterases after in vivo administration of the conjugate. The faster removal of a phenolic carbonate at the 10 position vs. a tertiary carbonate at the 20 position of 10-hydroxycamptothecin under physiological condition has been described by He et al. (He et al., *Bioorganic & Medicinal Chemistry* 12: 4003-4008 (2004)). A 10-hydroxy protecting group on SN-38 can be 'COR' where R can be a substituted alkyl such as "$N(CH_3)_2$—$(CH_2)_n$—" where n is 1-10 and wherein the terminal amino group is optionally in the form of a quaternary salt for enhanced aqueous solubility, or a simple alkyl residue such as "$CH_3$—$(CH_2)_n$—" where n is 0-10, or it can be an alkoxy moiety such as "$CH_3$—$(CH_2)$ n-O—" where n is 0-10, or "$N(CH_3)_2$—$(CH_2)_n$—O—" where n is 2-10, or "$R_1O$—$(CH_2$—$CH_2$—$O)_n$—$CH_2$—$CH_2$—O—" where $R_1$ is ethyl or methyl and n is an integer with values of 0-10. These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used.

In a preferred process of the preparation of a conjugate of a drug derivative and an antibody of the general formula 2, wherein the descriptors L2, L1, AA and A-X are as described in earlier sections, the bifunctional drug moiety, [L2]-[L1]-[AA]$_m$-[A-X]-Drug is first prepared, followed by the conjugation of the bifunctional drug moiety to the antibody (indicated herein as "MAb").

In a preferred process of the preparation of a conjugate of a drug derivative and an antibody of the general formula 2, wherein the descriptors L2, L1, AA and A-OH are as described in earlier sections, the bifunctional drug moiety is prepared by first linking A-OH to the C-terminus of AA via an amide bond, followed by coupling the amine end of AA to a carboxylic acid group of L1. If AA is absent (i.e. m=0), A-OH is directly attached to L1 via an amide bond. The cross-linker, [L1]-[AA]$_m$-[A-OH], is attached to drug's hydroxyl or amino group, and this is followed by attachment to the L1 moiety, by taking recourse to the reaction between azide (or acetylene) and acetylene (or azide) groups in L1 and L2 via click chemistry.

In one embodiment, the antibody is a monoclonal antibody (MAb). In other embodiments, the antibody may be a multivalent and/or multispecific MAb. The antibody may be a murine, chimeric, humanized, or human monoclonal antibody, and said antibody may be in intact, fragment (Fab, Fab', F(ab)$_2$, F(ab')$_2$), or sub-fragment (single-chain constructs) form, or of an IgG1, IgG2a, IgG3, IgG4, IgA isotype, or submolecules therefrom.

In a preferred embodiment, the antibody binds to an antigen or epitope of an antigen expressed on a cancer or malignant cell, most preferably Trop-2. The cancer cell is preferably a cell from a hematopoietic tumor, carcinoma, sarcoma, melanoma or a glial tumor. A preferred malignancy to be treated according to the present invention is a malignant solid tumor or hematopoietic neoplasm.

In a preferred embodiment, the intracellularly-cleavable moiety may be cleaved after it is internalized into the cell upon binding by the MAb-drug conjugate to a receptor thereof.

Checkpoint Inhibitor Antibodies

Studies with checkpoint inhibitor antibodies for cancer therapy have generated unprecedented response rates in cancers previously thought to be resistant to cancer treatment (see, e.g., Ott & Bhardwaj, 2013, Frontiers in Immunology 4:346; Menzies & Long, 2013, Ther Adv Med Oncol 5:278-85; Pardoll, 2012, Nature Reviews 12:252-264; Mavilio & Lugli,). Therapy with antagonistic checkpoint blocking antibodies against CTLA-4, PD-1 and PD-L1 are one of the most promising new avenues of immunotherapy for cancer and other diseases. In contrast to the majority of anti-cancer agents, checkpoint inhibitor do not target tumor cells directly, but rather target lymphocyte receptors or their ligands in order to enhance the endogenous antitumor activity of the immune system. (Pardoll, 2012, Nature Reviews 12:252-264) Because such antibodies act primarily by regulating the immune response to diseased cells, tissues or pathogens, they may be used in combination with other therapeutic modalities, such as antibody-drug conjugates (ADCs), to enhance the anti-tumor effect of the ADCs.

Programmed cell death protein 1 (PD-1, also known as CD279) encodes a cell surface membrane protein of the immunoglobulin superfamily, which is expressed in B cells and NK cells (Shinohara et al., 1995, Genomics 23:704-6; Blank et al., 2007, Cancer Immunol Immunother 56:739-45; Finger et al., 1997, Gene 197:177-87; Pardoll, 2012, Nature Reviews 12:252-264). Anti-PD1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85).

Exemplary anti-PD1 antibodies include pembrolizumab (MK-3475, MERCK), nivolumab (BMS-936558, BRISTOL-MYERS SQUIBB), and pidilizumab (CT-011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4).

Programmed cell death 1 ligand 1 (PD-L1, also known as CD274) is a ligand for PD-1, found on activated T cells, B cells, myeloid cells and macrophages. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PDL1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51).

Exemplary anti-PDL1 antibodies include MDX-1105 (MEDAREX), durvalumab (MEDI4736, MEDIMMUNE) atezolizumab (TECENTRIQ®, MPDL3280A, GENENTECH) and BMS-936559 (BRISTOL-MYERS SQUIBB). Anti-PDL1 antibodies are also commercially available, for example from AFFYMETRIX EBIOSCIENCE (MIH1).

Cytotoxic T-lymphocyte antigen 4 (CTLA-4, also known as CD152) is also a member of the immunoglobulin superfamily that is expressed exclusively on T-cells. CTLA-4 acts to inhibit T cell activation and is reported to inhibit helper T cell activity and enhance regulatory T cell immunosuppressive activity (Pardoll, 2012, Nature Reviews 12:252-264). Anti-CTL4A antibodies have been used in clinical trials for treatment of melanoma, prostate cancer, small cell lung cancer, non-small cell lung cancer (Robert & Ghirinhelli, 2009, Oncologist 14:848-61; Ott et al., 2013, Clin Cancer Res 19:5300; Weber, 2007, Oncologist 12:864-72; Wada et al., 2013, J Transl Med 11:89).

Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, J Transl Med 11:89).

These and other known checkpoint inhibitor antibodies may be used in combination with IMMU-132. In preferred embodiments, IMMU-132, alone or in combination, is effective to treat patients with cancers refractory to checkpoint inhibitor antibodies alone.

General Antibody Techniques

Techniques for preparing monoclonal antibodies against virtually any target antigen are well known in the art. See, for example, Köhler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures. The person of ordinary skill will realize that where antibodies are to be administered to human subjects, the antibodies will bind to human antigens.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

The skilled artisan will realize that the claimed methods and compositions may utilize any of a wide variety of antibodies known in the art. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441;

6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953; 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Isolated antibodies may be conjugated to therapeutic agents, such as camptothecins, using the techniques disclosed herein.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, *Hybridoma* 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, *Nature*, 321:522; Riechmann et al., *Nature*, 1988, 332:323; Verhoeyen et al., 1988, *Science*, 239:1534; Carter et al., 1992, *Proc. Nat'l Acad. Sci. USA*, 89:4285; Sandhu, *Crit. Rev. Biotech.*, 1992, 12:437; Tempest et al., 1991, *Biotechnology* 9:266; Singer et al., *J. Immun.*, 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., *Int. J. Cancer* 46: 310 (1990). In another embodiment, an antibody may be a human monoclonal antibody. Such antibodies may be obtained from transgenic mice that have been engineered to produce specific human antibodies in response to antigenic challenge, as discussed below.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the µ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A non-limiting example of such a system is the XENOMOUSE® (e.g., Green et al., 1999, *J. Immunol. Methods* 231:11-23, incorporated herein by reference) from Abgenix (Fremont, Calif.), in which the mouse antibody genes have been inactivated and replaced by functional human antibody genes, while the remainder of the mouse immune system remains intact.

The transgenic mice were transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of genetically engineered mice are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Production of Antibody Fragments

Some embodiments of the claimed methods and/or compositions may concern antibody fragments. Such antibody fragments may be obtained, for example, by pepsin or papain digestion of whole antibodies by conventional methods. For example, antibody fragments may be produced by enzymatic cleavage of antibodies with pepsin to provide a 5S fragment denoted F(ab')$_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. Nos. 4,036,945; 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as E. coli. The recombinant host cells synthesize a single polypeptide chain with a linker peptide bridging the two V domains. Methods for producing scFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780). Other types of antibody fragments may comprise one or more complementarity-determining regions (CDRs). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Antibody Variations

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797; each incorporated herein by reference).

Target Antigens and Exemplary Antibodies

In a preferred embodiment, antibodies are used that recognize and/or bind to antigens that are expressed at high levels on target cells and that are expressed predominantly or exclusively on diseased cells versus normal tissues. More preferably, the antibodies internalize rapidly following binding. An exemplary rapidly internalizing antibody is the LL1 (anti-CD74) antibody, with a rate of internalization of approximately $8 \times 10^6$ antibody molecules per cell per day (e.g., Hansen et al., 1996, Biochem J. 320:293-300). Thus, a "rapidly internalizing" antibody may be one with an internalization rate of $1 \times 10^6$ to about $1 \times 10^7$ antibody molecules per cell per day. Antibodies of use in the claimed compositions and methods may include MAbs with properties as recited above. Exemplary antibodies of use for therapy of, for example, cancer include but are not limited to LL1 (anti-CD74), LL2 or RFB4 (anti-CD22), veltuzumab (hA20, anti-CD20), rituximab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as TROP-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin)

and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730,300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU-31 (U.S. Pat. No. 7,300,655), hLL1 (U.S. Pat. No. 7,312,318,), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PGI-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections. In a particularly preferred embodiment, the antibody is hRS7. The person of ordinary skill will realize that in certain embodiments, antibodies against other TAAs besides Trop-2 may be used in combination with an anti-Trop-2 antibody.

Other useful antigens that may be targeted include carbonic anhydrase IX, B7, CCL19, CCL21, CSAp, HER-2/neu, BrE3, CD1, CD1a, CD2, CD3, CD4, CD8, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., bevacizumab, fibronectin splice variant), ED-B fibronectin (e.g., L19), EGP-1 (TROP-2), EGP-2 (e.g., 17-1A), EGF receptor (ErbB1) (e.g., cetuximab), ErbB2, ErbB3, Factor H, FHL-1, Flt-3, folate receptor, Ga 733, GRO-β, HMGB-1, hypoxia inducible factor (HIF), HM1.24, HER-2/neu, insulin-like growth factor (ILGF), IFN-γ, IFN-α, IFN-X, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (PlGF), PSA (prostate-specific antigen), PSMA, PAM4 antigen, PD-1 receptor, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, *Blood* prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J. Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba et al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8). Another useful target for breast cancer therapy is the LIV-1 antigen described by Taylor et al. (*Biochem. J.* 2003; 375:51-9). The CD47 antigen is a further useful target for cancer stem cells (see, e.g., Naujokat et al., 2014, Immunotherapy 6:290-308; Goto et al., 2014, Eur J Cancer 50:1836-46; Unanue, 2013, Proc Natl Acad Sci USA 110:10886-7).

For multiple myeloma therapy, suitable targeting antibodies have been described against, for example, CD38 and CD138 (Stevenson, *Mol Med* 2006; 12(11-12):345-346; Tassone et al., *Blood* 2004; 104(12):3688-96), CD74 (Stein et al., ibid.), CS1 (Tai et al., *Blood* 2008; 112(4):1329-37, and CD40 (Tai et al., 2005; *Cancer Res.* 65(13):5898-5906).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, *BMC Cancer* 12:34; Shachar & Haran, 2011, *Leuk Lymphoma* 52:1446-54); autoimmune diseases such as rheumatoid arthritis and systemic lupus erythematosus (Morand & Leech, 2005, *Front Biosci* 10:12-22; Shachar & Haran, 2011, *Leuk Lymphoma* 52:1446-54); kidney diseases such as renal allograft rejection (Lan, 2008, *Nephron Exp Nephrol.* 109:e79-83); and numerous inflammatory diseases (Meyer-Siegler et al., 2009, *Mediators Inflamm* epub Mar. 22, 2009; Takahashi et al., 2009, *Respir Res* 10:33; Milatuzumab (hLL1) is an exemplary anti-CD74 antibody of therapeutic use for treatment of MIF-mediated diseases.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, *Diabetes* 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-a4 integrin) and omalizumab (anti-IgE).

In another preferred embodiment, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., *Immunology* 98:296-302 (1999)). A review of the use of CD74 antibodies in cancer is contained in Stein et al., *Clin Cancer Res.* 2007 Sep. 15; 13(18 Pt 2):5556s-5563s, incorporated herein by reference.

The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. *Lancet.* 1990; 355:368-371). A preferred bispecific antibody is an anti-CD3 X anti-CD19 antibody. In alternative embodiments, an anti-CD3 antibody or fragment thereof may be attached to an antibody or fragment against another B-cell associated antigen, such as anti-CD3 X anti-Trop-2, anti-CD3 X anti-CD20, anti-CD3 X anti-CD22, anti-CD3 X anti-HLA-DR or anti-CD3 X anti-CD74. In certain embodiments, the techniques and compositions for ADC therapy disclosed herein may be used in combination with bispecific or multispecific antibodies. For example, an anti-Trop-2 x anti-CD3 bsAb may be administered before, simultaneously with or after an anti-Trop-2 ADC.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, *Nature,* 1983; 305:537-540).

Another method for producing bispecific antibodies uses heterobifunctional cross-linkers to chemically tether two different monoclonal antibodies (Staerz, et al. *Nature,* 1985; 314:628-631; Perez, et al. *Nature,* 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. *Proc Natl Acad Sci USA.* 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. *Proc Natl Acad Sci USA.* 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. Nos. 4,946,778 and 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens.

Dock-and-Lock™ (Dnl®)

In preferred embodiments, a bivalent or multivalent antibody is formed as a DOCK-AND-LOCK® (DNL®) complex (see, e.g., U.S. Pat. Nos. 7,521,056; 7,527,787; 7,534, 866; 7,550,143; 7,666,400; 7,858,070; 7,871,622; 7,906, 121; 7,906,118; 8,163,291; 7,901,680; 7,981,398; 8,003,111 and 8,034,352, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264. Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL® complex comprises a trimer with two DDD-linked molecules attached to one AD-linked molecule, variations in complex structure allow the formation of dimers, trimers, tetramers, pentamers, hexamers and other multimers. In some embodiments, the DNL® complex may comprise two or more antibodies, antibody fragments or fusion proteins which bind to the same antigenic determinant or to two or more different antigens. The DNL® complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., *J. Biol. Chem.* 1968; 243:3763). The structure of the holoenzyme consists of two catalytic subunits held in an inactive form by the R subunits (Taylor, *J. Biol. Chem.* 1989; 264:8443). Isozymes of PKA are found with two types of R subunits (RI and RII), and each type has □ and □ isoforms (Scott, *Pharmacol. Ther.* 1991; 50:123). Thus, the four isoforms of PKA regulatory subunits are RI□, RI□, RII□ and RII□. The R subunits have been isolated only as stable dimers and the dimerization domain has been shown to consist of the first 44 amino-terminal residues of RIIα (Newlon et al., *Nat. Struct. Biol.* 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., *J. Biol. Chem.* 1990; 265; 21561)

Since the first AKAP, microtubule-associated protein-2, was characterized in 1984 (Lohmann et al., *Proc. Natl. Acad. Sci USA.* 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, *Nat. Rev. Mol. Cell Biol.* 2004; 5:959). The AD of AKAPs for PKA is an amphipathic helix of 14-18 residues (Carr et al., *J. Biol. Chem.* 1991; 266:14188). The amino acid sequences of the AD are quite varied among individual AKAPs, with the binding affinities reported for RII dimers ranging from 2 to 90 nM (Alto et al., *Proc. Natl. Acad. Sci. USA.* 2003; 100:4445). AKAPs will only bind to dimeric R subunits. For human RII□, the AD binds to a hydrophobic surface formed by the 23 amino-terminal residues (Colledge and Scott, *Trends Cell Biol.* 1999; 6:216). Thus, the dimerization domain and AKAP binding domain of human RII□ are both located within the same N-terminal 44 amino acid sequence (Newlon et al., *Nat. Struct. Biol.* 1999; 6:222; Newlon et al., *EMBO J.* 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_1b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., *Proc. Natl. Acad. Sci. USA.* 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527, 787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL® construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., *Molecular Cloning, A laboratory manual*, 2$^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

In various embodiments, an antibody or antibody fragment may be incorporated into a DNL™ complex by, for example, attaching a DDD or AD moiety to the C-terminal end of the antibody heavy chain, as described in detail below. In more preferred embodiments, the DDD or AD moiety, more preferably the AD moiety, may be attached to the C-terminal end of the antibody light chain (see, e.g., U.S. patent application Ser. No. 13/901,737, filed May 24, 2013, the Examples section of which is incorporated herein by reference.)

Structure-Function Relationships in AD and DDD Moieties

For different types of DNL™ constructs, different AD or DDD sequences may be utilized. Exemplary DDD and AD sequences are provided below.

```
DDD1
                                       (SEQ ID NO: 7)
SHIQIPPGLTELLQGYTVEVLRQQPPDLVEFAVEYFTRLREARA

DDD2
                                       (SEQ ID NO: 8)
CGHIQIPPGLTELLQGYTVEVLRQQPPDLVEFAVEYFTRLREARA

AD1
                                       (SEQ ID NO: 9)
QIEYLAKQIVDNAIQQA

AD2
                                       (SEQ ID NO: 10)
CGQIEYLAKQIVDNAIQQAGC
```

The skilled artisan will realize that DDD1 and DDD2 are based on the DDD sequence of the human RII☐☐ isoform of protein kinase A. However, in alternative embodiments, the DDD and AD moieties may be based on the DDD sequence of the human RI☐☐ form of protein kinase A and a corresponding AKAP sequence, as exemplified in DDD3, DDD3C and AD3 below.

```
DDD3
                                       (SEQ ID NO: 11)
SLRECELYVQKHNIQALLKDSIVQLCTARPERPMAFLREYFERLEKEEAK

DDD3C
                                       (SEQ ID NO: 12)
MSCGGSLRECELYVQKHNIQALLKDSIVQLCTARPERPMAFLREYFERLE
KEEAK

AD3
                                       (SEQ ID NO: 13)
CGFEELAWKIAKMIWSDVFQQGC
```

In other alternative embodiments, other sequence variants of AD and/or DDD moieties may be utilized in construction of the DNL® complexes. For example, there are only four variants of human PKA DDD sequences, corresponding to the DDD moieties of PKA RIα, RIIα, RIβ and RIIβ. The RIIα DDD sequence is the basis of DDD I and DDD2 disclosed above. The four human PKA DDD sequences are shown below. The DDD sequence represents residues 1-44 of RIIα, 1-44 of RIIβ, 12-61 of RIα and 13-66 of RIP. (Note that the sequence of DDD1 is modified slightly from the human PKA RIIα DDD moiety.)

```
PKA RIα
                                       (SEQ ID NO: 14)
SLRECELYVQKHNIQALLKDVSIVQLCTARPERPMAFLREYFEKLEKEE
AK

PKA RIβ
                                       (SEQ ID NO: 15)
SLKGCELYVQLHGIQQVLKDCIVHLCISKPERPMKFLREHFEKLEKEEN
RQILA

PKA RIIα
                                       (SEQ ID NO: 16)
SHIQIPPGLTELLQGYTVEVGQQPPDLVDFAVEYFTRLREARRQ

PKA RIIβ
                                       (SEQ ID NO: 17)
SIEIPAGLTELLQGFTVEVLRHQPADLLEFALQHFTRLQQENER.
```

The structure-function relationships of the AD and DDD domains have been the subject of investigation. (See, e.g., Burns-Hamuro et al., 2005, *Protein Sci* 14:2982-92; Can et al., 2001, *J Biol Chem* 276:17332-38; Alto et al., 2003, *Proc Natl Acad Sci USA* 100:4445-50; Hundsrucker et al., 2006, *Biochem J* 396:297-306; Stokka et al., 2006, *Biochem J* 400:493-99; Gold et al., 2006, *Mol Cell* 24:383-95; Kinderman et al., 2006, *Mol Cell* 24:397-408, the entire text of each of which is incorporated herein by reference.)

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:18) and veltuzumab (SEQ ID NO:19).

```
Rituximab heavy chain variable region sequence
                                      (SEQ ID NO: 18)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKA

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

Veltuzumab heavy chain variable region
                                      (SEQ ID NO: 19)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

Jefferis and Lefranc (2009, *mAbs* 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1 m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotypoe characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, *J Clin Oncol* 27:3346-53; Goldenberg et al., 2009, *Blood* 113:1062-70; Robak & Robak, 2011, *BioDrugs* 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | |
|---|---|---|---|---|---|
| | Complete allotype | 214 (allotype) | 356/358 (allotype) | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Avimers

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, *Nat. Biotechnol.* 23:1493-94; Silverman et al., 2006, *Nat. Biotechnol.* 24:220). The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, *Science* 228:1315-1317; Smith and Scott, 1993, *Meth. Enzymol.* 21:228-257). In addition to peptides, larger protein domains such as single-chain antibodies may also be displayed on the surface of phage particles (Arap et al., 1998, Science 279: 377-380).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat. Nos. 5,475,096 and 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S. Not all linkages in an oligomer need to be identical.

Affibodies and Fynomers

Certain alternative embodiments may utilize affibodies in place of antibodies. Affibodies are commercially available from Affibody AB (Solna, Sweden). Affibodies are small proteins that function as antibody mimetics and are of use in binding target molecules. Affibodies were developed by combinatorial engineering on an alpha helical protein scaffold (Nord et al., 1995, Protein Eng 8:601-8; Nord et al., 1997, Nat Biotechnol 15:772-77). The affibody design is based on a three helix bundle structure comprising the IgG binding domain of protein A (Nord et al., 1995; 1997). Affibodies with a wide range of binding affinities may be produced by randomization of thirteen amino acids involved in the Fc binding activity of the bacterial protein A (Nord et al., 1995; 1997). After randomization, the PCR amplified library was cloned into a phagemid vector for screening by phage display of the mutant proteins. The phage display library may be screened against any known antigen, using standard phage display screening techniques (e.g., Pasqualini and Ruoslahti, 1996, Nature 380:364-366; Pasqualini, 1999, Quart. J. Nucl. Med. 43:159-162), in order to identify one or more affibodies against the target antigen.

A $^{177}$Lu-labeled affibody specific for HER2/neu has been demonstrated to target HER2-expressing xenografts in vivo (Tolmachev et al., 2007, Cancer Res 67:2773-82). Although renal toxicity due to accumulation of the low molecular weight radiolabeled compound was initially a problem, reversible binding to albumin reduced renal accumulation, enabling radionuclide-based therapy with labeled affibody (Id.).

The feasibility of using radiolabeled affibodies for in vivo tumor imaging has been recently demonstrated (Tolmachev et al., 2011, Bioconjugate Chem 22:894-902). A maleimide-derivatized NOTA was conjugated to the anti-HER2 affibody and radiolabeled with $^{111}$In (Id.). Administration to mice bearing the HER2-expressing DU-145 xenograft, followed by gamma camera imaging, allowed visualization of the xenograft (Id.).

Fynomers can also bind to target antigens with a similar affinity and specificity to antibodies. Fynomers are based on the human Fyn SH3 domain as a scaffold for assembly of binding molecules. The Fyn SH3 domain is a fully human, 63 amino acid protein that can be produced in bacteria with high yields. Fynomers may be linked together to yield a multispecific binding protein with affinities for two or more different antigen targets. Fynomers are commercially available from COVAGEN AG (Zurich, Switzerland).

The skilled artisan will realize that affibodies or fynomers may be used as targeting molecules in the practice of the claimed methods and compositions.

Immunoconjugates

In certain embodiments, a cytotoxic drug or other therapeutic or diagnostic agent may be covalently attached to an antibody or antibody fragment to form an immunoconjugate. In some embodiments, a drug or other agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio) propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the ADC is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for ADC formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2]azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetylmannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or Vκ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of ADC formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

The preferred conjugation protocol is based on a thiol-maleimide, a thiol-vinylsulfone, a thiol-bromoacetamide, or a thiol-iodoacetamide reaction that is facile at neutral or acidic pH. This obviates the need for higher pH conditions for conjugations as, for instance, would be necessitated when using active esters. Further details of exemplary conjugation protocols are described below in the Examples section.

Therapeutic Treatment

In another aspect, the invention relates to a method of treating a subject, comprising administering to a subject a therapeutically effective amount of an antibody-drug conjugate (ADC), such as IMMU-132, as described herein. Preferably the subject has a Trop-2 positive cancer that is resistant to therapy with checkpoint inhibitor antibodies. The ADCs can be given once or repeatedly, depending on the disease state and tolerability of the conjugate, and can also be used optionally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. It is not intended that the term be limited to a particular age or sex. Thus, adult and newborn subjects, as well as fetuses, whether male or female, are encompassed by the term. Doses given herein are for humans, but can be adjusted to the size of other mammals, as well as children, in accordance with weight or square meter size.

In a preferred embodiment, therapeutic conjugates comprising an anti-TROP-2 antibody such as the hRS7 MAb can be used to treat carcinomas such as carcinomas of the esophagus, pancreas, lung, stomach, colon and rectum, urinary bladder, breast, ovary, uterus, kidney and prostate, as disclosed in U.S. Pat. Nos. 7,238,785; 7,517,964 and 8,084,583, the Examples section of which is incorporated herein by reference. An hRS7 antibody is a humanized antibody that comprises light chain complementarity-determining region (CDR) sequences CDR1 (KASQDVSIAVA, SEQ ID NO:1); CDR2 (SASYRYT, SEQ ID NO:2); and CDR3 (QQHYITPLT, SEQ ID NO:3) and heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6).

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy.

In a preferred embodiment, a more effective incorporation into cells can be accomplished by using multivalent, multispecific or multivalent, monospecific antibodies. Examples of such bivalent and bispecific antibodies are found in U.S. Pat. Nos. 7,387,772; 7,300,655; 7,238,785; and 7,282,567, the Examples section of each of which is incorporated herein by reference. These multivalent or multispecific antibodies are particularly preferred in the targeting of cancers and infectious organisms (pathogens), which express multiple antigen targets and even multiple epitopes of the same antigen target, but which often evade antibody targeting and sufficient binding for immunotherapy because of insufficient expression or availability of a single antigen target on the cell or pathogen. By targeting multiple antigens or epitopes, said antibodies show a higher binding and residence time on the target, thus affording a higher saturation with the drug being targeted in this invention.

In another preferred embodiment, a therapeutic agent used in combination with the camptothecin conjugate of this invention may comprise one or more isotopes. Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{227}$Th and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}C$, $^{13}N$, $^{15}O$, $^{75}Br$, $^{198}Au$, $^{224}Ac$, $^{126}I$, $^{133}I$, $^{77}Br$, $^{113m}In$, $^{95}Ru$, $^{97}Ru$, $^{103}Ru$, $^{105}Ru$, $^{107}Hg$, $^{203}Hg$, $^{121m}Te$, $^{122m}Te$, $^{125m}Te$, $^{165}Tm$, $^{167}Tm$, $^{168}Tm$, $^{197}Pt$, $^{109}Pd$, $^{105}Rh$, $^{142}Pr$, $^{143}Pr$, $^{161}Tb$, $^{161}Ho$, $^{199}Au$, $^{57}Co$, $^{58}Co$, $^{51}Cr$, $^{59}Fe$, $^{75}Se$, $^{201}Tl$, $^{225}Ac$, $^{76}Br$, $^{169}Yb$, and the like.

Radionuclides and other metals may be delivered, for example, using chelating groups attached to an antibody or conjugate. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}Ra$, may be used.

Therapeutic agents of use in combination with the camptothecin conjugates described herein also include, for example, chemotherapeutic drugs such as *vinca* alkaloids, anthracyclines, epidophyllotoxins, taxanes, antimetabolites, tyrosine kinase inhibitors, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Exemplary drugs of use include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epipodophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839. Such agents may be part of the conjugates described herein or may alternatively be administered in combination with the described conjugates, either prior to, simultaneously with or after the conjugate.

Therapeutic agents that may be used in concert with the camptothecin conjugates also may comprise toxins conjugated to targeting moieties. Toxins that may be used in this regard include ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin. (See, e.g., Pastan. et al., *Cell* (1986), 47:641, and Sharkey and Goldenberg, *CA Cancer J Clin.* 2006 July-August; 56(4):226-43.) Additional toxins suitable for use herein are known to those of skill in the art and are disclosed in U.S. Pat. No. 6,077,499.

Yet another class of therapeutic agent may comprise one or more immunomodulators. Immunomodulators of use may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -γ or -λ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-β, IL-14, IL-15, IL-16, IL-17, IL-18, IL-21, IL-25, LIF, kit-ligand or FLT-3, angiostatin, thrombospondin, endostatin, tumor necrosis factor and lymphotoxin (LT). As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

In certain embodiments, a therapeutic agent to be used in combination with an anti-Trop-2 ADC is a microtubule inhibitor, such as a *vinca* alkaloid, a taxanes, a maytansinoid or an auristatin. Exemplary known microtubule inhibitors include paclitaxel, vincristine, vinblastine, mertansine, epothilone, docetaxel, discodermolide, combrestatin, podophyllotoxin, CI-980, phenylahistins, steganacins, curacins, 2-methoxy estradiol, E7010, methoxy benzenesuflonamides, vinorelbine, vinflunine, vindesine, dolastatins, spongistatin, rhizoxin, tasidotin, halichondrins, hemiasterlins, cryptophycin 52, MMAE and eribulin mesylate.

In an alternative embodiment, a therapeutic agent to be used in combination with an ADC is a PARP inhibitor, such as olaparib, talazoparib (BMN-673), rucaparib, veliparib, CEP 9722, MK 4827, BGB-290, ABT-888, AG014699, BSI-201, CEP-8983 or 3-aminobenzamide.

In another alternative, a therapeutic agent used in combination with an ADC is a Bruton tyrosine kinase inhibitor, such as such as ibrutinib (PCI-32765), PCI-45292, CC-292 (AVL-292), ONO-4059, GDC-0834, LFM-A13 or RN486.

In yet another alternative, a therapeutic agent used in combination with an ADC is a PI3K inhibitor, such as idelalisib, Wortmannin, demethoxyviridin, perifosine, PX-866, IPI-145 (duvelisib), BAY 80-6946, BEZ235, RP6530, TGR1202, SF1126, INK1117, GDC-0941, BKM120, XL147, XL765, Palomid 529, GSK1059615, ZSTK474, PWT33597, IC87114, TG100-115, CAL263, PI-103, GNE477, CUDC-907, AEZS-136 or LY294002.

The person of ordinary skill will realize that the subject ADCs, comprising a camptothecin conjugated to an antibody or antibody fragment, may be used alone or in combination with one or more other therapeutic agents, such as a second antibody, second antibody fragment, second immunoconjugate, radionuclide, toxin, drug, chemotherapeutic agent, radiation therapy, chemokine, cytokine, immunomodulator, enzyme, hormone, oligonucleotide, RNAi or siRNA. Such additional therapeutic agents may be administered separately, in combination with, or attached to the subject antibody-drug ADCs.

Formulation and Administration

Suitable routes of administration of the conjugates include, without limitation, oral, parenteral, subcutaneous, rectal, transmucosal, intestinal administration, intramuscular, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

ADCs can be formulated according to known methods to prepare pharmaceutically useful compositions, whereby the ADC is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

In a preferred embodiment, the ADC is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino)ethanesulfonic acid (MES); 3-(N-morpholino)propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The ADC can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Where subcutaneous administration is desired, the antibody may be concentrated, for example as disclosed in U.S. Pat. No. 9,180,205, the Examples section of which is incorporated herein by reference. Subcutaneous injections may be administered as 1, 2, or 3 ml injections, which may be administered at a single site or at two or more sites. Each injection would typically contain between 1.5 and 4 mg/kg of concentrated ADC.

Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the ADC. For example, biocompatible polymers include matrices of polyethylene-co-vinyl acetate) and matrices of a polyanhydride copolymer of a stearic acid dimer and sebacic acid. Sherwood et al., *Bio/Technology* 10: 1446 (1992). The rate of release of an ADC from such a matrix depends upon the molecular weight of the ADC, the amount of ADC within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered ADC for humans will vary depending upon such factors as the patient's age, weight, height, sex, general medical condition and previous medical history. It may be desirable to provide the recipient with a dosage of ADC that is in the range of from about 1 mg/kg to 24 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. Preferred dosages may include, but are not limited to, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Any amount in the range of 1 to 24 mg/kg may be used. The dosage is preferably administered multiple times, once or twice a week. A minimum dosage schedule of 4 weeks, more preferably 8 weeks, more preferably 16 weeks or longer may be used. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 4, 6, 8, 10, 12, 16 or 20 times or more.

Alternatively, an ADC may be administered as one dosage every 2 or 3 weeks, repeated for a total of at least 3 dosages. Or, twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 12 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the ADCs are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenström's macroglobulinemia, Wilms' tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W.B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodei Hal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodennal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias; e.g., acute lymphocytic leukemia, acute myelocytic leukemia [including myeloblastic, promyelocytic, myelomonocytic, monocytic, and erythroleukemia]) and chronic leukemias (e.g., chronic myelocytic [granulocytic] leukemia and chronic lymphocytic leukemia), polycythemia vera, lymphomas (e.g., Hodgkin's disease and non-Hodgkin's disease), multiple myeloma, Waldenström's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Autoimmune diseases that may be treated with ADCs may include acute and chronic immune thrombocytopenias, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

Kits

Various embodiments may concern kits containing components suitable for treating diseased tissue in a patient. Exemplary kits may contain at least one ADC or other targeting moiety as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers.

Another component that can be included is instructions to a person using a kit for its use.

EXAMPLES

Various embodiments of the present invention are illustrated by the following examples, without limiting the scope thereof.

Example 1. Production and Use of Anti-Trop-2-SN-38 Antibody-Drug Conjugate

The humanized RS7 (hRS7) anti-Trop-2 antibody was produced as described in U.S. Pat. No. 7,238,785, the Figures and Examples section of which are incorporated herein by reference. SN-38 attached to a CL2A linker was produced and conjugated to hRS7 (anti-Trop-2), hPAM4 (anti-MUC5ac), hA20 (anti-CD20) or hMN-14 (anti-CEACAM5) antibodies according to U.S. Pat. No. 7,999,083 (Example 10 and 12 of which are incorporated herein by reference). The conjugation protocol resulted in a ratio of about 6 SN-38 molecules attached per antibody molecule.

Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. In a Capan 1 pancreatic tumor model, specific CL2A-SN-38 conjugates of hRS7 (anti-Trop-2), hPAM4 (anti-MUC-5ac), and hMN-14 (anti-CEACAM5) antibodies showed better efficacies than control hA20-CL2A-SN-38 conjugate (anti-CD20) and untreated control (not shown). Similarly in a BXPC3 model of human pancreatic cancer, the specific hRS7-CL2A-SN-38 showed better therapeutic efficacy than control treatments (not shown).

Example 2. Therapeutic Use of Anti-Trop-2 ADC (Sacituzumab Govitecan) in Patients Refractory to Checkpoint Inhibitor Therapy Summary IMMU-132 (sacituzumab govitecan, aka hRS7-CL2A-SN-38) has shown promising therapeutic results in phase II trials of patients with metastatic triple-negative breast and other cancers who were heavily pretreated (ClinicalTrials.gov, NCT01631552), and who express high levels of Trop-2. This novel Trop-2-targeting humanized antibody is conjugated with 7.6 moles of SN-38, the active form of irinotecan, by the CL2A linker discussed above, and is less glucuronidated in vivo than irinotecan, accounting for a significantly lower incidence of diarrhea in patients treated with the agent.

Surprisingly, IMMU-132 is highly efficacious in patients who have previously relapsed from or shown resistance to many standard anti-cancer therapies, including the parent compound irinotecan. A new class of anti-cancer agents, known as checkpoint inhibitors, include antibodies or other inhibitory agents against cytotoxic T-lymphocyte antigen 4 (CTLA-4), programmed cell death protein (PD-1) and programmed cell death ligand 1 (PD-L1). As described herein, IMMU-132 shows surprising and unexpected efficacy against tumors that are relapsed/refractory to checkpoint inhibitors as well as other anti-cancer agents.

The data below summarizes results for an exemplary case study of a patient (255-029) who responded to therapy with IMMU-132 after having shown resistance to a PD-L1 inhibitor.

Cancer: TNBC (patient progressed after PD-L1 therapy)
Best Response: Partial response, confirmed (54% shrinkage)
IMMU-132 starting dose: 10 mg/kg
Number IMMU-132 treatments: 40+
Time to Progression: 12.4+ months (not reached)
End of study: Continuing treatment
Medical History—

The patient is a 47-year old female who was first diagnosed in October 2007 with a 1.8 cm mass in her right breast. She underwent a right mastectomy with a sentinel node biopsy (no malignancy in nodes). The tumor was determined to be negative for ER, PR and Her-2 (i.e., TNBC). She proceeded with 4 cycles of AC (doxorubicin and cyclophosphamide) therapy, followed by weekly low dose paclitaxel (×12). In October 2008, a CT study showed a previously unnoticed pulmonary nodule and an enlarged mammary node; the node was cancer. She had local surgery to remove the node and then received XRT (radiation therapy) through March 2009. In June 2010 CT documented recurrent pulmonary and bone involvement. The patient enrolled in a clinical trial using AVASTIN® (bevacizumab), METMAB® (onartuzumab, anti-hepatocyte growth factor), and TAXOL® (paclitaxel), which she was maintained on until March 2013, having a complete response, but eventual progression of peripheral lung nodule and node in AP (aortopulmonary) window. In September 2014, she started on PD-L1 antibody (MPDL3280A) for 6 cycles, but progressed in January 2015. She was then referred to the IMMU-132 trial.

IMMU-132 Treatment—

The patient initiated treatment on 6 Feb. 2015 at a dose of 10 mg/kg, and has continued to receive this dose without reduction or delay in planned schedule now for 40+ doses.

Results

The patient initially presented with 3 target lesions (1 lung, 2 lymph nodes in the chest) with a sum of diameters equaling 60 mm, and an additional non-target lesion (another lymph node in the chest) (FIG. 2). On first assessment (7 Apr. 2015), the patient's sum of the target lesion diameters decreased 33%, qualifying as a RECIST 1.1 partial response. A confirmatory follow-CT performed weeks later (18 May 2015) showed the response improving, with a 48% overall reduction (FIG. 3, FIG. 4). On 19 Jul. 2015, CT showed the patient continued with a partial response, having 50% shrinkage. A CT on 13 Sep. 2015 showed a continuing PR with a 52% shrinkage, and one on 15 Nov. 15 showed a 54% shrinkage. The latest CT performed on 25 Feb. 2016 showed the PR was continuing with a 46% shrinkage.

A summary of CT results is shown in FIG. 1. Baseline CT scans are shown in FIG. 2, with axial images on the top row and sagittal images on the bottom row (tumors indicated by arrows). A direct comparison of the target lesions is seen in FIG. 3 and FIG. 4. FIG. 3 shows both target lesions 1 and 2, taken in the same plane. Baseline (29 Jan. 2015) is shown on top. A significant shrinkage in both L1 and L2 was apparent on the second response assessment (19 May 2015), shown on the bottom. FIG. 4 shows the equivalent images for target lesion 3, with baseline on top and second response assessment on the bottom. The patient is continuing treatment and continues to show a partial response to IMMU-132, after previously failing checkpoint inhibitor therapy.

Immunohistochemical analysis for Trop-2 expression of the patient's tumors showed positive expression, with a staining level of 2+ (data not shown).

Toxicities—

As of the date of this report, the most severe adverse effect has been a G3 hypophosphatemia (not related), with likely related toxicities being a G2 neutropenia 2002 Apr. 15; dose 6), fatigue (G1), nausea (G1), a maculo-popular rash (G1), alopecia (G2), and rhinorrhea (G1).

These results demonstrate that IMMU-132 is highly efficacious in patients who had previously been relapsed from or resistant to checkpoint inhibitor therapy. At a therapeutic dosage of IMMU-132, the patient showed only manageable toxicities. These results show the utility of IMMU-132 for Trop-2 positive cancers, such as triple negative breast cancer (TNBC).

Example 3. ADCC Activity of Anti-Trop-2 ADCs

The ADCC activity of various hRS7-ADC conjugates was determined in comparison to hRS7 IgG (not shown). PBMCs were purified from blood purchased from the Blood Center of New Jersey. A Trop-2-positive human pancreatic adenocarcinoma cell line (BxPC-3) was used as the target cell line with an effector to target ratio of 100:1. ADCC mediated by hRS7 IgG was compared to hRS7-Pro-2-PDox, hRS7-CL2A-SN-38, and the reduced and capped hRS7-NEM. All were used at 33.3 nM.

Overall activity was low, but significant (not shown). There was 8.5% specific lysis for the hRS7 IgG which was not significantly different from hRS7-Pro-2-PDox. Both were significantly better than hLL2 control and hRS7-NEM and sacituzumab govitecan (P<0.02, two-tailed t-test). There was no difference between hRS7-NEM and sacituzumab govitecan.

Example 4. Efficacy of anti-Trop-2-SN-38 ADC Against Diverse Epithelial Cancers

In Vivo

Abstract

The purpose of this study was to evaluate the efficacy of an SN-38-anti-Trop-2 (hRS7) ADC against several human solid tumor types, and to assess its tolerability in mice and monkeys, the latter with tissue cross-reactivity to hRS7 similar to humans Two SN-38 derivatives, CL2-SN-38 and CL2A-SN-38, were conjugated to the anti-Trop-2-humanized antibody, hRS7. The ADCs were characterized in vitro for stability, binding, and cytotoxicity. Efficacy was tested in five different human solid tumor-xenograft models that expressed Trop-2 antigen. Toxicity was assessed in mice and in Cynomolgus monkeys.

The hRS7 conjugates of the two SN-38 derivatives were equivalent in drug substitution (~6), cell binding ($K_d$~1.2 nmol/L), cytotoxicity ($IC_{50}$~2.2 nmol/L), and serum stability in vitro ($t_{1/2}$~20 hours). Exposure of cells to the ADC demonstrated signaling pathways leading to PARP cleavage, but differences versus free SN-38 in p53 and p21 upregulation were noted. Significant antitumor effects were produced by sacituzumab govitecan at nontoxic doses in mice bearing Calu-3 (P≤0.05), Capan-1 (P<0.018), BxPC-3 (P<0.005), and COLO 205 tumors (P<0.033) when compared to nontargeting control ADCs. Mice tolerated a dose of 2×12 mg/kg (SN-38 equivalents) with only short-lived elevations in ALT and AST liver enzyme levels. Cynomolgus monkeys infused with 2×0.96 mg/kg exhibited only transient decreases in blood counts, although, importantly, the values did not fall below normal ranges.

In summary, the anti-Trop-2 hRS7-CL2A-SN-38 ADC provided significant and specific antitumor effects against a range of human solid tumor types. It was well tolerated in monkeys, with tissue Trop-2 expression similar to humans, at clinically relevant doses.

Introduction

Successful irinotecan treatment of patients with solid tumors has been limited, due in large part to the low conversion rate of the CPT-11 prodrug into the active SN-38 metabolite. Others have examined nontargeted forms of SN-38 as a means to bypass the need for this conversion and to deliver SN-38 passively to tumors. We conjugated SN-38 covalently to a humanized anti-Trop-2 antibody, hRS7. This antibody-drug conjugate has specific antitumor effects in a range of s.c. human cancer xenograft models, including non-small cell lung carcinoma, pancreatic, colorectal, and squamous cell lung carcinomas, all at nontoxic doses (e.g., ≤3.2 mg/kg cumulative SN-38 equivalent dose). Trop-2 is widely expressed in many epithelial cancers, but also some normal tissues, and therefore a dose escalation study in Cynomolgus monkeys was performed to assess the clinical safety of this conjugate. Monkeys tolerated 24 mg SN-38 equivalents/kg with only minor, reversible, toxicities. Given its tumor-targeting and safety profile, sacituzumab govitecan provides a significant improvement in the management of solid tumors responsive to irinotecan.

Material and Methods

Cell Lines, Antibodies, and Chemotherapeutics—

All human cancer cell lines used in this study were purchased from the American Type Culture Collection. These include Calu-3 (non-small cell lung carcinoma), SK-MES-1 (squamous cell lung carcinoma), COLO 205 (colonic adenocarcinoma), Capan-1 and BxPC-3 (pancreatic adenocarcinomas), and PC-3 (prostatic adenocarcinomas). Humanized RS7 IgG and control humanized anti-CD20 (hA20 IgG, veltuzumab) and anti-CD22 (hLL2 IgG, epratuzumab) antibodies were prepared at Immunomedics, Inc. Irinotecan (20 mg/mL) was obtained from Hospira, Inc.

SN-38 ADCs and In Vitro Aspects—

Synthesis of CL2-SN-38 has been described previously (Moon et al., 2008, J Med Chem 51:6916-26). Its conjugation to hRS7 IgG and serum stability were performed as described (Moon et al., 2008, J Med Chem 51:6916-26; Govindan et al., 2009, Clin Chem Res 15:6052-61). Preparations of CL2A-SN-38 (M.W. 1480) and its hRS7 conjugate, and stability, binding, and cytotoxicity studies, were conducted as described in the preceding Examples.

In Vivo Therapeutic Studies—

For all animal studies, the doses of SN-38 ADCs and irinotecan are shown in SN-38 equivalents. Based on a mean SN-38/IgG substitution ratio of 6, a dose of 500m ADC to a 20-g mouse (25 mg/kg) contains 0.4 mg/kg of SN-38. Irinotecan doses are likewise shown as SN-38 equivalents (i.e., 40 mg irinotecan/kg is equivalent to 24 mg/kg of SN-38).

NCr female athymic nude (nu/nu) mice, 4 to 8 weeks old, and male Swiss-Webster mice, 10 weeks old, were purchased from Taconic Farms. Tolerability studies were performed in Cynomolgus monkeys (*Macaca fascicularis*, 2.5-4 kg male and female) by SNBL USA, Ltd. Animals were implanted subcutaneously with different human cancer cell lines. Tumor volume (TV) was determined by measurements in 2 dimensions using calipers, with volumes defined as: L×w²/2, where L is the longest dimension of the tumor and w is the shortest. Tumors ranged in size between 0.10 and 0.47 cm³ when therapy began. Treatment regimens, dosages, and number of animals in each experiment are described in the Results. The lyophilized sacituzumab govitecan and control ADC were reconstituted and diluted as required in sterile saline. All reagents were administered intraperitoneally (0.1 mL), except irinotecan, which was administered intravenously. The dosing regimen was influenced by our prior investigations, where the ADC was given every 4 days or twice weekly for varying lengths of time (Moon et al., 2008, J Med Chem 51:6916-26; Govindan et al., 2009, Clin Chem Res 15:6052-61). This dosing frequency reflected a consideration of the conjugate's serum half-life in vitro, to allow a more continuous exposure to the ADC.

Statistics—

Growth curves are shown as percent change in initial TV over time. Statistical analysis of tumor growth was based on area under the curve (AUC). Profiles of individual tumor growth were obtained through linear-curve modeling. An f-test was employed to determine equality of variance between groups before statistical analysis of growth curves. A 2-tailed t-test was used to assess statistical significance between the various treatment groups and controls, except for the saline control, where a 1-tailed t-test was used (significance at $P \leq 0.05$). Statistical comparisons of AUC were performed only up to the time that the first animal within a group was euthanized due to progression.

Pharmacokinetics and Biodistribution—

$^{111}$In-radiolabeled sacituzumab govitecan and hRS7 IgG were injected into nude mice bearing s.c. SK-MES-1 tumors ($\sim$0.3 cm$^3$). One group was injected intravenously with 20 µCi (250-µg protein) of $^{111}$In-sacituzumab govitecan, whereas another group received 20 µCi (250-µg protein) of $^{111}$In-hRS7 IgG. At various timepoints mice (5 per timepoint) were anesthetized, bled via intracardiac puncture, and then euthanized. Tumors and various tissues were removed, weighed, and counted by γ scintillation to determine the percentage injected dose per gram tissue (% ID/g). A third group was injected with 250 µg of unlabeled sacituzumab govitecan 3 days before the administration of $^{111}$In-sacituzumab govitecan and likewise necropsied. A 2-tailed t-test was used to compare sacituzumab govitecan and hRS7 IgG uptake after determining equality of variance using the f-test. Pharmacokinetic analysis on blood clearance was performed using WinNonLin software (Parsight Corp.).

Tolerability in Swiss-Webster Mice and Cynomolgus Monkeys—

Briefly, mice were sorted into 4 groups each to receive 2-mL i.p. injections of either a sodium acetate buffer control or 3 different doses of sacituzumab govitecan (4, 8, or 12 mg/kg of SN-38) on days 0 and 3 followed by blood and serum collection, as described in Results. Cynomolgus monkeys (3 male and 3 female; 2.5-4.0 kg) were administered 2 different doses of sacituzumab govitecan. Dosages, times, and number of monkeys bled for evaluation of possible hematologic toxicities and serum chemistries are described in the Results.

Results

Stability and Potency of hRS7-SN-38—

Two different linkages were used to conjugate SN-38 to hRS7 IgG (not shown). The first is termed CL2-SN-38 and has been described previously (Moon et al., 2008, J Med Chem 51:6916-26; Govindan et al., 2009, Clin Chem Res 15:6052-61). A change in the synthesis of CL2 to remove the phenylalanine moiety within the linker was used to produce the CL2A linker. This change simplified the synthesis, but did not affect the conjugation outcome (e.g., both CL2-SN-38 and CL2A-SN-38 incorporated $\sim$6 SN-38 per IgG molecule). Side-by-side comparisons found no significant differences in serum stability, antigen binding, or in vitro cytotoxicity. This result was surprising, since the phenylalanine residue in CL2 is part of a designed cleavage site for cathepsin B, a lysosomal protease.

To confirm that the change in the SN-38 linker from CL2 to CL2A did not impact in viva potency, sacituzumab govitecan and hRS7-CL2-SN-38 were compared in mice bearing COLO 205 (not shown) or Capan-1 tumors (not shown), using 0.4 mg or 0.2 mg/kg SN-38 twice weekly×4 weeks, respectively, and with starting tumors of 0.25 cm$^3$ size in both studies. Both the sacituzumab govitecan and CL2-SN-38 conjugates significantly inhibited tumor growth compared to untreated ($AUC_{14days}$ P<0.002 vs. saline in COLO 205 model; $AUC_{21days}$ P<0.001 vs. saline in Capan-1 model), and a nontargeting anti-CD20 control ADC, hA20-CL2A-SN-38 ($AUC_{14days}$ P<0.003 in COLO-205 model; $AUC_{35days}$: P<0.002 in Capan-1 model). At the end of the study (day 140) in the Capan-1 model, 50% of the mice treated with sacituzumab govitecan and 40% of the hRS7-CL2-SN-38 mice were tumor-free, whereas only 20% of the hA20-ADC-treated animals had no visible sign of disease. The CL2A linker resulted in a higher efficacy compared to CL2 (not shown).

Mechanism of Action—

In vitro cytotoxicity studies demonstrated that sacituzumab govitecan had IC$_{50}$ values in the nmol/L range against several different solid tumor lines (Table 2). The IC$_{50}$ with free SN-38 was lower than the conjugate in all cell lines. Although there was no apparent correlation between Trop-2 expression and sensitivity to sacituzumab govitecan, the IC$_{50}$ ratio of the ADC versus free SN-38 was lower in the higher Trop-2-expressing cells, most likely reflecting the enhanced ability to internalize the drug when more antigen is present.

SN-38 is known to activate several signaling pathways in cells, leading to apoptosis (e.g., Cusack et al., 2001, Cancer Res 61:3535-40; Liu et al. 2009, Cancer Lett 274:47-53; Lagadec et al., 2008, Br J Cancer 98:335-44). Our initial studies examined the expression of 2 proteins involved in early signaling events (p21$^{Waf1/Cip1}$ and p53) and 1 late apoptotic event [cleavage of poly-ADP-ribose polymerase (PARP)] in vitro (not shown). In BxPC-3, SN-38 led to a 20-fold increase in p21$^{Waf1/Cip1}$ expression (not shown), whereas sacituzumab govitecan resulted in only a 10-fold increase (not shown), a finding consistent with the higher activity with free SN-38 in this cell line (Table 2). However, sacituzumab govitecan increased p21$^{Waf1/Cip1}$ expression in Calu-3 more than 2-fold over free SN-38 (not shown).

A greater disparity between sacituzumab govitecan- and free SN-38-mediated signaling events was observed in p53 expression (not shown). In both BxPC-3 and Calu-3, upregulation of p53 with free SN-38 was not evident until 48 hours, whereas sacituzumab govitecan upregulated p53 within 24 hours (not shown). In addition, p53 expression in cells exposed to the ADC was higher in both cell lines compared to SN-38 (not shown). Interestingly, although hRS7 IgG had no appreciable effect on p21$^{Waf1/Cip1}$ expression, it did induce the upregulation of p53 in both BxPC-3 and Calu-3, but only after a 48-hour exposure (not shown). In terms of later apoptotic events, cleavage of PARP was evident in both cell lines when incubated with either SN-38 or the conjugate (not shown). The presence of the cleaved PARP was higher at 24 hours in BxPC-3 (not shown), which correlates with high expression of p21 and its lower IC$_{50}$. The higher degree of cleavage with free SN-38 over the ADC was consistent with the cytotoxicity findings.

Efficacy of hRS7-SN-38—

Because Trop-2 is widely expressed in several human carcinomas, studies were performed in several different human cancer models, which started using the hRS7-CL2-SN-38 linkage, but later, conjugates with the CL2A-linkage were used. Calu-3-bearing nude mice given 0.04 mg SN-38/kg of the hRS7-CL2-SN-38 every 4 days×4 had a significantly improved response compared to animals administered the equivalent amount of non-targeting hLL2-CL2-SN-38 (TV=0.14±0.22 cm$^3$ vs. 0.80±0.91 cm$^3$, respectively; AUC$_{42days}$ P<0.026; not shown). A dose-response was observed when the dose was increased to 0.4 mg/kg SN-38 (not shown). At this higher dose level, all mice given the specific hRS7 conjugate were "cured" within 28 days, and remained tumor-free until the end of the study on day 147, whereas tumors regrew in animals treated with the irrelevant ADC (specific vs. irrelevant AUC$_{98days}$: P=0.05). In mice receiving the mixture of hRS7 IgG and SN-38, tumors progressed >4.5-fold by day 56 (TV=1.10±0.88 cm$^3$; AUC$_{56days}$ P<0.006 vs. hRS7-CL2-SN-38) (not shown).

Efficacy also was examined in human colonic (COLO 205) and pancreatic (Capan-1) tumor xenografts. In COLO 205 tumor-bearing animals, (not shown), hRS7-CL2-SN-38 (0.4 mg/kg, q4dx8) prevented tumor growth over the 28-day treatment period with significantly smaller tumors compared to control anti-CD20 ADC (hA20-CL2-SN-38), or hRS7 IgG (TV=0.16±0.09 cm$^3$, 1.19±0.59 cm$^3$, and 1.77±0.93 cm$^3$, respectively; AUC$_{28days}$ P<0.016).

Studies with the sacituzumab govitecan ADC were then extended to 2 other models of human epithelial cancers. In mice bearing BxPC-3 human pancreatic tumors (not shown), sacituzumab govitecan again significantly inhibited tumor growth in comparison to control mice treated with saline or an equivalent amount of nontargeting hA20-CL2A-SN-38 (TV=0.24±0.11 cm$^3$ vs. 1.17±0.45 cm$^3$ and 1.05±0.73 cm$^3$, respectively; AUC$_{day21}$P<0.001), or irinotecan given at a 10-fold higher SN-38 equivalent dose (TV=0.27±0.18 cm$^3$ vs. 0.90±0.62 cm$^3$, respectively; AUC$_{day25}$P<0.004) (not shown). Interestingly, in mice bearing SK-MES-1 human squamous cell lung tumors treated with 0.4 mg/kg of the ADC (not shown), tumor growth inhibition was superior to saline or unconjugated hRS7 IgG (TV=0.36±0.25 cm$^3$ vs. 1.02±0.70 cm$^3$ and 1.30±1.08 cm$^3$, respectively; AUC$_{28 days}$; P<0.043), but nontargeting hA20-CL2A-SN-38 or the MTD of irinotecan provided the same antitumor effects as the specific hRS7-SN-38 conjugate (not shown). In all murine studies, the hRS7-SN-38 ADC was well tolerated in terms of body weight loss (not shown).

Biodistribution of Sacituzumab Govitecan—

The biodistributions of sacituzumab govitecan or unconjugated hRS7 IgG were compared in mice bearing SK-MES-1 human squamous cell lung carcinoma xenografts (not shown), using the respective $^{111}$In-labeled substrates. A

TABLE 2

Expression of Trop-2 in vitro cytotoxicity of SN-38 and hRS7-SN-38 in various solid tumor lines

| | Trop-2 expression via FACS | | Cytotoxicity results | | | | |
|---|---|---|---|---|---|---|---|
| | | | SN-38 | 95% CI | hRS7-SN-38 | 95% CI | |
| Cell line | Median fluorescence (background) | Percent positive | IC$_{50}$ (nmol/L) | IC$_{50}$ (nmol/L) | IC$_{50}$ (nmol/L) | IC$_{50}$ (nmol/L) | ADC/free SN-38 ratio |
| Calu-3 | 282.2 (4.7) | 99.6% | 7.19 | 5.77-8.95 | 9.97 | 8.12-12.25 | 1.39 |
| COLO 205 | 141.5 (4.5) | 99.5% | 1.02 | 0.66-1.57 | 1.95 | 1.26-3.01 | 1.91 |
| Capan-1 | 100.0 (5.0) | 94.2% | 3.50 | 2.17-5.65 | 6.99 | 5.02-9.72 | 2.00 |
| PC-3 | 46.2 (5.5) | 73.6% | 1.86 | 1.16-2.99 | 4.24 | 2.99-6.01 | 2.28 |
| SK-MES-1 | 44.0 (3.5) | 91.2% | 8.61 | 6.30-11.76 | 23.14 | 17.98-29.78 | 2.69 |
| BxPC-3 | 26.4 (3.1) | 98.3% | 1.44 | 1.04-2.00 | 4.03 | 3.25-4.98 | 2.80 |

The MTD of irinotecan (24 mg SN-38/kg, q2dx5) was as effective as hRS7-CL2-SN-38 in COLO 205 cells, because mouse serum can more efficiently convert irinotecan to SN-38 (Morton et al., 2000, Cancer Res 60:4206-10) than human serum, but the SN-38 dose in irinotecan (2,400 μg cumulative) was 37.5-fold greater than with the conjugate (64 μg total).

Animals bearing Capan-1 (not shown) showed no significant response to irinotecan alone when given at an SN-38-dose equivalent to the hRS7-CL2-SN-38 conjugate (e.g., on day 35, average tumor size was 0.04±0.05 cm$^3$ in animals given 0.4 mg SN-38/kg hRS7-SN-38 vs. 1.78±0.62 cm$^3$ in irinotecan-treated animals given 0.4 mg/kg SN-38; AUC$_{day35}$ P<0.001; not shown). When the irinotecan dose was increased 10-fold to 4 mg/kg SN-38, the response improved, but still was not as significant as the conjugate at the 0.4 mg/kg SN-38 dose level (TV=0.17±0.18 cm$^3$ vs. 1.69±0.47 cm$^3$, AUC$_{day49}$P<0.001) (not shown). An equal dose of nontargeting hA20-CL2-SN-38 also had a significant antitumor effect as compared to irinotecan-treated animals, but the specific hRS7 conjugate was significantly better than the irrelevant ADC (TV=0.17±0.18 cm$^3$ vs. 0.80±0.68 cm$^3$, AUC$_{day49}$P<0.018) (not shown).

pharmacokinetic analysis was performed to determine the clearance of sacituzumab govitecan relative to unconjugated hRS7 (not shown). The ADC cleared faster than the equivalent amount of unconjugated hRS7, with the ADC exhibiting ~40% shorter half-life and mean residence time. Nonetheless, this had a minimal impact on tumor uptake (not shown). Although there were significant differences at the 24- and 48-hour timepoints, by 72 hours (peak uptake) the amounts of both agents in the tumor were similar. Among the normal tissues, hepatic and splenic differences were the most striking (not shown). At 24 hours postinjection, there was >2-fold more sacituzumab govitecan in the liver than hRS7 IgG (not shown). Conversely, in the spleen there was 3-fold more parental hRS7 IgG present at peak uptake (48-hour timepoint) than sacituzumab govitecan (not shown). Uptake and clearance in the rest of the tissues generally reflected differences in the blood concentration (not shown).

Because twice-weekly doses were given for therapy, tumor uptake in a group of animals that first received a predose of 0.2 mg/kg (250 μg protein) of the hRS7 ADC 3 days before the injection of the $^{111}$In-labeled antibody was examined. Tumor uptake of $^{111}$In-sacituzumab govitecan in predosed mice was substantially reduced at every timepoint in comparison to animals that did not receive the predose (e.g., at 72 hours, predosed tumor uptake was 12.5%±3.8% ID/g vs. 25.4%±8.1% ID/g in animals not given the predose; P=0.0123; not shown). Predosing had no appreciable impact on blood clearance or tissue uptake (not shown). These studies suggest that in some tumor models, tumor accretion of the specific antibody can be reduced by the preceding dose(s), which likely explains why the specificity of a therapeutic response could be diminished with increasing ADC doses and why further dose escalation is not indicated.

Tolerability of Sacituzumab Govitecan in Swiss-Webster Mice and Cynomolgus Monkeys Swiss-Webster mice tolerated 2 doses over 3 days, each of 4, 8, and 12 mg SN-38/kg of sacituzumab govitecan, with minimal transient weight loss (not shown). No hematopoietic toxicity occurred and serum chemistries only revealed elevated aspartate transaminase (AST, not shown) and alanine transaminase (ALT, not shown). Seven days after treatment, AST rose above normal levels (>298 U/L) in all 3 treatment groups (not shown), with the largest proportion of mice being in the 2×8 mg/kg group. However, by 15 days posttreatment, most animals were within the normal range. ALT levels were also above the normal range (>77 U/L) within 7 days of treatment (not shown) and with evidence of normalization by Day 15. Livers from all these mice did not show histologic evidence of tissue damage (not shown). In terms of renal function, only glucose and chloride levels were somewhat elevated in the treated groups. At 2×8 mg/kg, 5 of 7 mice had slightly elevated glucose levels (range of 273-320 mg/dL, upper end of normal 263 mg/dL) that returned to normal by 15 days postinjection. Similarly, chloride levels were slightly elevated, ranging from 116 to 127 mmol/L (upper end of normal range 115 mmol/L) in the 2 highest dosage groups (57% in the 2×8 mg/kg group and 100% of the mice in the 2×12 mg/kg group), and remained elevated out to 15 days postinjection. This also could be indicative of gastrointestinal toxicity, because most chloride is obtained through absorption by the gut; however, at termination, there was no histologic evidence of tissue damage in any organ system examined (not shown).

Because mice do not express the Trop-2 target antigen of hRS7 in normal tissues, a more suitable model was required to determine the potential of the hRS7 conjugate for clinical use. Immunohistology studies revealed binding in multiple tissues in both humans and Cynomolgus monkeys (breast, eye, gastrointestinal tract, kidney, lung, ovary, fallopian tube, pancreas, parathyroid, prostate, salivary gland, skin, thymus, thyroid, tonsil, ureter, urinary bladder, and uterus; not shown). Based on this cross-reactivity, a tolerability study was performed in monkeys.

The group receiving 2×0.96 mg SN-38/kg of sacituzumab govitecan had no significant clinical events following the infusion and through the termination of the study. Weight loss did not exceed 7.3% and returned to acclimation weights by day 15. Transient decreases were noted in most of the blood count data (not shown), but values did not fall below normal ranges. No abnormal values were found in the serum chemistries. Histopathology of the animals necropsied on day 11 (8 days after last injection) showed microscopic changes in hematopoietic organs (thymus, mandibular and mesenteric lymph nodes, spleen, and bone marrow), gastrointestinal organs (stomach, duodenum, jejunum, ileum, cecum, colon, and rectum), female reproductive organs (ovary, uterus, and vagina), and at the injection site. These changes ranged from minimal to moderate and were fully reversed at the end of the recovery period (day 32) in all tissues, except in the thymus and gastrointestinal tract, which were trending towards full recovery at this later timepoint (not shown).

At the 2×1.92 mg SN-38/kg dose level of the conjugate, there was 1 death arising from gastrointestinal complications and bone marrow suppression, and other animals within this group showed similar, but more severe adverse events than the 2×0.96 mg/kg group (not shown). These data indicate that dose-limiting toxicities were identical to that of irinotecan; namely, intestinal and hematologic. Thus, the MTD for sacituzumab govitecan lies between 2×0.96 and 1.92 mg SN-38/kg, which represents a human equivalent dose of 2×0.3 to 0.6 mg/kg SN-38.

Discussion

Trop-2 is a protein expressed on many epithelial tumors, including lung, breast, colorectal, pancreas, prostate, and ovarian cancers, making it a potentially important target for delivering cytotoxic agents (Ohmachi et al., 2006, Clin Cancer Res 12:3057-63; Fong et al., 2008, Br J Cancer 99:1290-95; Cubas et al., 2009, Biochim Biophys Acta 1796:309-14). The RS7 antibody internalizes when bound to Trop-2 (Shih et al., 1995, Cancer Res 55:5857s-63s), which enables direct intracellular delivery of cytotoxics.

SN-38 is a potent topoisomerase-I inhibitor, with $IC_{50}$ values in the nanomolar range in several cell lines. It is the active form of the prodrug, irinotecan, that is used for the treatment of colorectal cancer, and which also has activity in lung, breast, and brain cancers. We reasoned that a directly targeted SN-38, in the form of an ADC, would be a significantly improved therapeutic over CPT-11, by overcoming the latter's low and patient-variable bioconversion to active SN-38 (Mathijssen et al., 2001, Clin Cancer Res 7:2182-94).

The Phe-Lys peptide inserted in the original CL2 derivative allowed for possible cleavage via cathepsin B. To simplify the synthetic process, in CL2A the phenylalanine was eliminated, and thus the cathepsin B cleavage site was removed. Interestingly, this product had a better-defined chromatographic profile compared to the broad profile obtained with CL2 (not shown), but more importantly, this change had no impact on the conjugate's binding or stability, and surprisingly produced a small increase in potency in side-by-side testing.

In vitro cytotoxicity of hRS7 ADC against a range of solid tumor cell lines consistently had $IC_{50}$ values in the nmol/L range. However, cells exposed to free SN-38 demonstrated a lower $IC_{50}$ value compared to the ADC. This disparity between free and conjugated SN-38 was also reported for ENZ-2208 (Sapra et al., 2008, Clin Cancer Res 14:1888-96, Zhao et al., 2008, Bioconjug Chem 19:849-59) and NK012 (Koizumi et al., 2006, Cancer Res 66:10048-56). ENZ-2208 utilizes a branched PEG to link about 3.5 to 4 molecules of SN-38 per PEG, whereas NK012 is a micelle nanoparticle containing 20% SN-38 by weight. With our ADC, this disparity (i.e., ratio of potency with free vs. conjugated SN-38) decreased as the Trop-2 expression levels increased in the tumor cells, suggesting an advantage to targeted delivery of the drug. In terms of in vitro serum stability, both the CL2- and CL2A-SN-38 forms of hRS7-SN-38 yielded a $t_{1/2}$ of ~20 hours, which is in contrast to the short $t_{1/2}$ of 12.3 minutes reported for ENZ-2208 (Zhao et al., 2008, Bioconjug Chem 19:849-59), but similar to the 57% release of SN-38 from NK012 under physiological conditions after 24 hours (Koizumi et al., 2006, Cancer Res 66:10048-56). Treatment of tumor-bearing mice with hRS7-SN-38 (either with CL2-SN-38 or CL2A-SN-38) significantly inhibited tumor growth in 5 different tumor models. In 4 of them, tumor regressions were observed, and in the case of Calu-3, all mice receiving the highest dose of hRS7-SN-38 were tumor-free at the conclusion of study. Unlike in humans, irinotecan is very efficiently converted to SN-38 by a plasma esterase in mice, with a greater than 50% conversion rate, and yielding higher efficacy in mice than in humans (Morton et al., 2000, Cancer Res 60:4206-10; Furman et al., 1999, J Clin Oncol 17:1815-24). When irinotecan was administered at 10-fold higher or equivalent SN-38 levels, hRS7-SN-38 was significantly better in controlling tumor growth. Only when irinotecan was administered at its MTD of 24 mg/kg q2dx5 (37.5-fold more SN-38) did it equal the effectiveness of hRS7-SN-38. In patients, we would expect this advantage to favor sacituzumab govitecan even more, because the bioconversion of irinotecan would be substantially lower.

We also showed in some antigen-expressing cell lines, such as SK-MES-1, that using an antigen-binding ADC does not guarantee better therapeutic responses than a nonbinding, irrelevant conjugate. This is not an unusual or unexpected finding. Indeed, the nonbinding SN-38 conjugates mentioned earlier enhance therapeutic activity when compared to irinotecan, and so an irrelevant IgG-SN-38 conjugate is expected to have some activity. This is related to the fact that tumors have immature, leaky vessels that allow the passage of macromolecules better than normal tissues (Jain, 1994, Sci Am 271:58-61). With our conjugate, 50% of the SN-38 will be released in ~13 hours when the pH is lowered to a level mimicking lysosomal levels (e.g., pH 5.3 at 37° C.; data not shown), whereas at the neutral pH of serum, the release rate is reduced nearly 2-fold. If an irrelevant conjugate enters an acidic tumor microenvironment, it is expected to release some SN-38 locally. Other factors, such as tumor physiology and innate sensitivities to the drug, will also play a role in defining this "baseline" activity. However, a specific conjugate with a longer residence time should have enhanced potency over this baseline response as long as there is ample antigen to capture the specific antibody. Biodistribution studies in the SK-MES-1 model also showed that if tumor antigen becomes saturated as a consequence of successive dosing, tumor uptake of the specific conjugate is reduced, which yields therapeutic results similar to that found with an irrelevant conjugate.

Although it is challenging to make direct comparisons between our ADC and the published reports of other SN-38 delivery agents, some general observations can be made. In our therapy studies, the highest individual dose was 0.4 mg/kg of SN-38. In the Calu-3 model, only 4 injections were given for a total cumulative dose of 1.6 mg/kg SN-38 or 32 µg SN-38 in a 20 g mouse. Multiple studies with ENZ-2208 were done using its MTD of 10 mg/kg×5 (Sapra et al., 2008, Clin Cancer Res 14:1888-96; Pastorini et al., 2010, Clin Cancer Res 16:4809-21), and preclinical studies with NK012 involved its MTD of 30 mg/kg×3 (Koizumi et al., 2006, Cancer Res 66:10048-56). Thus, significant antitumor effects were obtained with hRS7-SN-38 at 30-fold and 55-fold less SN-38 equivalents than the reported doses in ENZ-2208 and NK012, respectively. Even with 10-fold less hRS7 ADC (0.04 mg/kg), significant antitumor effects were observed, whereas lower doses of ENZ-2208 were not presented, and when the NK012 dose was lowered 4-fold to 7.5 mg/kg, efficacy was lost (Koizumi et al., 2006, Cancer Res 66:10048-56). Normal mice showed no acute toxicity with a cumulative dose over 1 week of 24 mg/kg SN-38 (1,500 mg/kg of the conjugate), indicating that the MTD was higher. Thus, tumor-bearing animals were effectively treated with 7.5- to 15-fold lower amounts of SN-38 equivalents.

Biodistribution studies revealed that sacituzumab govitecan had similar tumor uptake as the parental hRS7 IgG, but cleared substantially faster with 2-fold higher hepatic uptake, which may be due to the hydrophobicity of SN-38. With the ADC being cleared through the liver, hepatic and gastrointestinal toxicities were expected to be dose limiting. Although mice had evidence of increased hepatic transaminases, gastrointestinal toxicity was mild at best, with only transient loss in weight and no abnormalities noted upon histopathologic examination. Interestingly, no hematological toxicity was noted. However, monkeys showed an identical toxicity profile as expected for irinotecan, with gastrointestinal and hematological toxicity being dose-limiting.

Because Trop-2 recognized by hRS7 is not expressed in mice, it was important to perform toxicity studies in monkeys that have a similar tissue expression of Trop-2 as humans. Monkeys tolerated 0.96 mg/kg/dose (~12 mg/m$^2$) with mild and reversible toxicity, which extrapolates to a human dose of ~0.3 mg/kg/dose (~11 mg/m$^2$). In a Phase I clinical trial of NK012, patients with solid tumors tolerated 28 mg/m$^2$ of SN-38 every 3 weeks with Grade 4 neutropenia as dose-limiting toxicity (DLT; Hamaguchi et al., 2010, *Clin Cancer Res* 16:5058-66). Similarly, Phase I clinical trials with ENZ-2208 revealed dose-limiting febrile neutropenia, with a recommendation to administer 10 mg/m$^2$ every 3 weeks or 16 mg/m$^2$ if patients were administered G-CSF (Kurzrock et al., *AACR-NCI-EORTC International Conference on Molecular Targets and Cancer Therapeutics;* 2009 Nov. 15-19; Boston, Mass.; Poster No C216; Patnaik et al., *AACR-NCI-EORTC International Conference on Molecular Targets and Cancer Therapeutics;* 2009 Nov. 15-19; Boston, Mass.; Poster No C221). Because monkeys tolerated a cumulative human equivalent dose of 22 mg/m$^2$, it appears that even though hRS7 binds to a number of normal tissues, the MTD for a single treatment of the hRS7 ADC could be similar to that of the other nontargeting SN-38 agents. Indeed, the specificity of the anti-Trop-2 antibody did not appear to play a role in defining the DLT, because the toxicity profile was similar to that of irinotecan. More importantly, if antitumor activity can be achieved in humans as in mice that responded with human equivalent dose of just at 0.03 mg SN-38 equivalents/kg/dose, then significant antitumor responses may be realized clinically.

In conclusion, toxicology studies in monkeys, combined with in vivo human cancer xenograft models in mice, have indicated that this ADC targeting Trop-2 is an effective therapeutic in several tumors of different epithelial origin.

Example 5. Cell Binding Assay of Anti-Trop-2 Antibodies

Two different murine monoclonal antibodies against human Trop-2 were obtained for ADC conjugation. The first, 162-46.2, was purified from a hybridoma (ATCC, HB-187) grown up in roller-bottles. A second antibody, MAB650, was purchased from R&D Systems (Minneapolis, Minn.). For a comparison of binding, the Trop-2 positive human gastric carcinoma, NCI-N87, was used as the target. Cells (1.5× 10$^5$/well) were plated into 96-well plates the day before the binding assay. The following morning, a dose/response curve was generated with 162-46.2, MAB650, and murine RS7 (0.03 to 66 nM). These primary antibodies were incubated with the cells for 1.5 h at 4° C. Wells were washed and an anti-mouse-HRP secondary antibody was added to all the wells for 1 h at 4° C. Wells are washed again followed by the addition of a luminescence substrate. Plates were read using Envision plate reader and values are reported as relative luminescent units.

All three antibodies had similar $K_D$-values of 0.57 nM for RS7, 0.52 nM for 162-46.2 and 0.49 nM for MAB650. However, when comparing the maximum binding ($B_{max}$) of 162-46.2 and MAB650 to RS7 they were reduced by 25% and 50%, respectively ($B_{Max}$ 11,250 for RS7, 8,471 for 162-46.2 and 6,018 for MAB650) indicating different binding properties in comparison to RS7.

Example 6. Cytotoxicity of Anti-Trop-2 ADC (MAB650-SN-38)

A novel anti-Trop-2 ADC was made with SN-38 and MAB650, yielding a mean drug to antibody substitution ratio of 6.89. Cytotoxicity assays were performed to compare the MAB650-SN-38 and sacituzumab govitecan ADCs using two different human pancreatic adenocarcinoma cell lines (BxPC-3 and Capan-1) and a human triple negative breast carcinoma cell line (MDA-MB-468) as targets.

One day prior to adding the ADCs, cells were harvested from tissue culture and plated into 96-well plates. The next day cells were exposed to sacituzumab govitecan, MAB650-SN-38, and free SN-38 at a drug range of $3.84\times10^{-12}$ to $2.5\times10^{-7}$ M. Unconjugated MAB650 was used as a control at protein equivalent doses as the MAB650-SN-38. Plates were incubated at 37° C. for 96 h. After this incubation period, an MTS substrate was added to all of the plates and read for color development at half-hour intervals until an $OD_{492nm}$ of approximately 1.0 was reached for the untreated cells. Growth inhibition was measured as a percent of growth relative to untreated cells using Microsoft Excel and Prism software (non-linear regression to generate sigmoidal dose response curves which yield $IC_{50}$-values.

Sacituzumab govitecan and MAB650-SN-38 had similar growth-inhibitory effects with $IC_{50}$-values in the low nM range which is typical for SN-38-ADCs in these cell lines (not shown). In the human Capan-1 pancreatic adenocarcinoma cell line (not shown), the sacituzumab govitecan ADC showed an $IC_{50}$ of 3.5 nM, compared to 4.1 nM for the MAB650-SN-38 ADC and 1.0 nM for free SN-38. In the human BxPC-3 pancreatic adenocarcinoma cell line (not shown), the sacituzumab govitecan ADC showed an $IC_{50}$ of 2.6 nM, compared to 3.0 nM for the MAB650-SN-38 ADC and 1.0 nM for free SN-38. In the human NCI-N87 gastric adenocarcinoma cell line (not shown), the sacituzumab govitecan ADC showed an $IC_{50}$ of 3.6 nM, compared to 4.1 nM for the MAB650-SN-38 ADC and 4.3 nM for free SN-38.

In summary, in these in vitro assays, the SN-38 conjugates of two anti-Trop-2 antibodies, hRS7 and MAB650, showed equal efficacies against several tumor cell lines, which was similar to that of free SN-38. Because the targeting function of the anti-Trop-2 antibodies would be a much more significant factor in vivo than in vitro, the data support that anti-Trop-2-SN-38 ADCs as a class would be highly efficacious in vivo, as demonstrated in the Examples above for sacituzumab govitecan.

Example 7. Cytotoxicity of Anti-Trop-2 ADC (162-46.2-SN-38)

A novel anti-Trop-2 ADC was made with SN-38 and 162-46.2, yielding a drug to antibody substitution ratio of 6.14. Cytotoxicity assays were performed to compare the 162-46.2-SN-38 and hRS7-SN-38 ADCs using two different Trop-2-positive cell lines as targets, the BxPC-3 human pancreatic adenocarcinoma and the MDA-MB-468 human triple negative breast carcinoma.

One day prior to adding the ADC, cells were harvested from tissue culture and plated into 96-well plates at 2000 cells per well. The next day cells were exposed to sacituzumab govitecan, 162-46.2-SN-38, or free SN-38 at a drug range of $3.84\times10^{42}$ to $2.5\times10^{-7}$ M. Unconjugated 162-46.2 and hRS7 were used as controls at the same protein equivalent doses as the 162-46.2-SN-38 and sacituzumab govitecan, respectively. Plates were incubated at 37° C. for 96 h. After this incubation period, an MTS substrate was added to all of the plates and read for color development at half-hour intervals until untreated control wells had an $OD_{492nm}$ reading of approximately 1.0. Growth inhibition was measured as a percent of growth relative to untreated cells using Microsoft Excel and Prism software (non-linear regression to generate sigmoidal dose response curves which yield $IC_{50}$-values).

The 162-46.2-SN-38 ADC had a similar $IC_{50}$-values when compared to sacituzumab govitecan (not shown). When tested against the BxPC-3 human pancreatic adenocarcinoma cell line (not shown), sacituzumab govitecan had an $IC_{50}$ of 5.8 nM, compared to 10.6 nM for 162-46.2-SN-38 and 1.6 nM for free SN-38. When tested against the MDA-MB-468 human breast adenocarcinoma cell line (not shown), sacituzumab govitecan had an $IC_{50}$ of 3.9 nM, compared to 6.1 nM for 162-46.2-SN-38 and 0.8 nM for free SN-38. The free antibodies alone showed little cytotoxicity to either Trop-2 positive cancer cell line.

In summary, comparing the efficacies in vitro of three different anti-Trop-2 antibodies conjugated to the same cytotoxic drug, all three ADCs exhibited equivalent cytotoxic effects against a variety of Trop-2 positive cancer cell lines. These data support that the class of anti-Trop-2 antibodies, incorporated into drug-conjugated ADCs, are effective anti-cancer therapeutic agents for Trop-2 expressing solid tumors.

Example 8. Clinical Trials With IMMU-132 (Sacituzumab Govitecan) Anti-Trop-2 ADC Comprising hRS7 Antibody Conjugated to SN-38

Summary

The present Example reports results from a phase I clinical trial and ongoing phase II extension with IMMU-132, an ADC of the internalizing, humanized, hRS7 anti-Trop-2 antibody conjugated by a pH-sensitive linker to SN-38 (mean drug-antibody ratio=7.6). Trop-2 is a type I transmembrane, calcium-transducing, protein expressed at high density ($\sim1\times10^5$), frequency, and specificity by many human carcinomas, with limited normal tissue expression. Preclinical studies in nude mice bearing Capan-1 human pancreatic tumor xenografts have revealed IMMU-132 is capable of delivering as much as 120-fold more SN-38 to tumor than derived from a maximally tolerated irinotecan therapy.

The present Example reports the initial Phase I trial of 25 patients who had failed multiple prior therapies (some including topoisomerase-I/II inhibiting drugs), and the ongoing Phase II extension now reporting on 69 patients, including in colorectal (CRC), small-cell and non-small cell lung (SCLC, NSCLC, respectively), triple-negative breast (TNBC), pancreatic (PDC), esophageal, and other cancers.

As discussed in detail below, Trop-2 was not detected in serum, but was strongly expressed ($\geq2^+$ immunohistochemical staining) in most archived tumors. In a 3+3 trial design, IMMU-132 was given on days 1 and 8 in repeated 21-day cycles, starting at 8 mg/kg/dose, then 12 and 18 mg/kg before dose-limiting neutropenia. To optimize cumulative treatment with minimal delays, phase II is focusing on 8 and 10 mg/kg (n=30 and 14, respectively). In 49 patients reporting related AE at this time, neutropenia ≥Grade 3 occurred in 28% (4% Grade 4). Most common non-hematological toxicities initially in these patients have been fatigue (55%; ≥G3=9%), nausea (53%; ≥G3=0%), diarrhea (47%2G3=9%), alopecia (40%), and vomiting (32%; ≥G3=2%); alopecia also occurred frequently. Homozygous UGT1A1*28/*28 was found in 6 patients, 2 of whom had more severe hematological and GI toxicities.

In the Phase I and the expansion phases, there are now 48 patients (excluding PDC) who are assessable by RECIST/CT for best response. Seven (15%) of the patients had a partial response (PR), including patients with CRC (N=1), TNBC (N=2), SCLC (N=2), NSCLC (N=1), and esophageal cancers (N=1), and another 27 patients (56%) had stable disease (SD), for a total of 38 patients (79%) with disease response; 8 of 13 CT-assessable PDC patients (62%) had SD, with a median time to progression (TTP) of 12.7 wks compared to 8.0 weeks in their last prior therapy. The TTP for the remaining 48 patients is 12.6+ wks (range 6.0 to 51.4 wks). Plasma CEA and CA19-9 correlated with responses who had elevated titers of these antigens in their blood. No anti-hRS7 or anti-SN-38 antibodies were detected despite dosing over months.

The conjugate cleared from the serum within 3 days, consistent with in vivo animal studies where 50% of the SN-38 was released daily, with >95% of the SN-38 in the serum being bound to the IgG in a non-glucoronidated form, and at concentrations as much as 100-fold higher than SN-38 reported in patients given irinotecan. These results show that sacituzumab govitecan is therapeutically active in metastatic solid cancers, with manageable diarrhea and neutropenia.

Pharmacokinetics

Two ELISA methods were used to measure the clearance of the IgG (capture with anti-hRS7 idiotype antibody) and the intact conjugate (capture with anti-SN-38 IgG/probe with anti-hRS7 idiotype antibody). SN-38 was measured by HPLC. Total IMMU-132 fraction (intact conjugate) cleared more quickly than the IgG (not shown), reflecting known gradual release of SN-38 from the conjugate. HPLC determination of SN-38 (Unbound and TOTAL) showed >95% the SN-38 in the serum was bound to the IgG. Low concentrations of SN-38G suggest SN-38 bound to the IgG is protected from glucoronidation. Comparison of ELISA for conjugate and SN-38 HPLC revealed both overlap, suggesting the ELISA is a surrogate for monitoring SN-38 clearance.

A summary of the dosing regiment and patient pool is provided in Table 3.

TABLE 3

Clinical Trial Parameters

| | |
|---|---|
| Dosing regimen | Once weekly for 2 weeks administered every 21 days for up to 8 cycles. In the initial enrollment, the planned dose was delayed and reduced if ≥ Grade 2 treatment-related toxicity; protocol was amended to dose delay and reduction only in the event of ≥ Grade 3 toxicity. |
| Dose level cohorts | 8, 12, 18 mg/kg; later reduced to an intermediate dose level of 10 mg/kg. |
| Cohort size | Standard Phase I [3 + 3] design; expansion includes ~15 patients in select cancers. |
| DLT | Grade 4 ANC ≥7 d; ≥ Grade 3 febrile neutropenia of any duration; G4 Plt ≥5 d; G4 Hgb; Grade 4 N/V/D any duration/G3 N/V/D for >48 h; G3 infusion-related reactions; related ≥ G3 non-hematological toxicity. |
| Maximum Acceptable Dose (MAD) | Maximum dose where ≥2/6 patients tolerate $1^{st}$ 21-d cycle w/o delay or reduction or ≥ G3 toxicity. |
| Patients | Metastatic colorectal, pancreas, gastric, esophageal, lung (NSCLC, SCLC), triple-negative breast (TNBC), prostate, ovarian, renal, urinary bladder, head/neck, hepatocellular. Refractory/relapsed after standard treatment regimens for metastatic cancer. Prior irinotecan-containing therapy NOT required for enrollment. No bulky lesion >5 cm. Must be 4 weeks beyond any major surgery, and 2 weeks beyond radiation or chemotherapy regimen. Gilbert's disease or known CNS metastatic disease are excluded. |

Clinical Trial Status

A total of 69 patients (including 25 patients in Phase I) with diverse metastatic cancers having a median of 3 prior therapies were reported. Eight patients had clinical progression and withdrew before CT assessment. Thirteen CT-assessable pancreatic cancer patients were separately reported. The median TTP (time to progression) in PDC patients was 11.9 wks (range 2 to 21.4 wks) compared to median 8 wks TTP for the preceding last therapy.

A total of 48 patients with diverse cancers had at least 1 CT-assessment from which Best Response (not shown) and Time to Progression (TTP; not shown) were determined. To summarize the Best Response data, of 8 assessable patients with TNBC (triple-negative breast cancer), there were 2 PR (partial response), 4 SD (stable disease) and 2 PD (progressive disease) for a total response [PR+SD] of 6/8 (75%). For SCLC (small cell lung cancer), of 4 assessable patients there were 2 PR, 0 SD and 2 PD for a total response of 2/4 (50%). For CRC (colorectal cancer), of 18 assessable patients there were 1 PR, 11 SD and 6 PD for a total response of 12/18 (67%). For esophageal cancer, of 4 assessable patients there were 1 PR, 2 SD and 1 PD for a total response of 3/4 (75%). For NSCLC (non-small cell lung cancer), of 5 assessable patients there were 1 PR, 3 SD and 1 PD for a total response of 4/5 (80%). Over all patients treated, of 48 assessable patients there were 7 PR, 27 SD and 14 PD for a total response of 34/48 (71%). These results demonstrate that the anti-TROP-2 ADC (hRS7-SN-38) showed significant clinical efficacy against a wide range of solid tumors in human patients.

The reported side effects of therapy (adverse events) are summarized in Table 4. As apparent from the data of Table 4, the therapeutic efficacy of sacituzumab govitecan was achieved at dosages of ADC showing an acceptably low level of adverse side effects.

TABLE 4

Related Adverse Events Listing for IMMU-132-01
Criteria: Total ≥10% or ≥ Grade 3

N = 47 patients

|  | TOTAL | Grade 3 | Grade 4 |
|---|---|---|---|
| Fatigue | 55% | 4 (9%) | 0 |
| Nausea | 53% | 0 | 0 |
| Diarrhea | 47% | 4 (9%) | 0 |
| Neutropenia | 43% | 11 (24%) | 2 (4%) |
| Alopecia | 40% | — | — |
| Vomiting | 32% | 1 (2%) | 0 |
| Anemia | 13% | 2 (4%) | 0 |
| Dysgeusia | 15% | 0 | 0 |
| Pyrexia | 13% | 0 | 0 |
| Abdominal pain | 11% | 0 | 0 |
| Hypokalemia | 11% | 1 (2%) | 0 |
| WBC Decrease | 6% | 1 (2%) | 0 |
| Febrile Neutropenia | 6% | 1 (2%) | 2 (4%) |
| Deep vein thrombosis | 2% | 1 (2%) | 0 |

Grading by CTCAE v 4.0

The study reported in Table 4 has continued, with 261 patients enrolled to date. The results (not shown) have generally followed along the lines indicated in Table 4, with only neutropenia showing an incidence of Grade 3 or higher adverse events of over 10% of the patients tested. For all other adverse events, the incidence of Grade 3 or higher responses was less than 10%. This distinguishes the instant ADCs from the great majority of ADCs and in certain embodiments, the claimed methods and compositions relate to anti-Trop-2 ADCs that show efficacy in diverse solid tumors, with an incidence of Grade 3 or higher adverse events of less than 10% of patients for all adverse events other than neutropenia. In a follow-up study, in a total of 421 samples from 121 patients with baseline and at least one follow-up sample available, no anti-hRS7 or anti-SN-38 antibody response has been detected, despite repeated cycles of treatment.

Exemplary partial responses to the anti-Trop-2 ADC were confirmed by CT data (not shown). As an exemplary PR in CRC, a 62 year-old woman first diagnosed with CRC underwent a primary hemicolectomy. Four months later, she had a hepatic resection for liver metastases and received 7 mos of treatment with FOLFOX and 1 mo 5FU. She presented with multiple lesions primarily in the liver (3+ Trop-2 by immunohistology), entering the sacituzumab govitecan trial at a starting dose of 8 mg/kg about 1 year after initial diagnosis. On her first CT assessment, a PR was achieved, with a 37% reduction in target lesions (not shown). The patient continued treatment, achieving a maximum reduction of 65% decrease after 10 months of treatment (not shown) with decrease in CEA from 781 ng/mL to 26.5 ng/mL), before progressing 3 months later.

As an exemplary PR in NSCLC, a 65 year-old male was diagnosed with stage MB NSCLC (sq. cell). Initial treatment of caboplatin/etoposide (3 mo) in concert with 7000 cGy XRT resulted in a response lasting 10 mo. He was then started on Tarceva maintenance therapy, which he continued until he was considered for IMMU-132 trial, in addition to undergoing a lumbar laminectomy. He received first dose of IMMU-132 after 5 months of Tarceva, presenting at the time with a 5.6 cm lesion in the right lung with abundant pleural effusion. He had just completed his 6$^{th}$ dose two months later when the first CT showed the primary target lesion reduced to 3.2 cm (not shown).

As an exemplary PR in SCLC, a 65 year-old woman was diagnosed with poorly differentiated SCLC. After receiving carboplatin/etoposide (Topoisomerase-II inhibitor) that ended after 2 months with no response, followed with topotecan (Topoisomerase-I inhibitor) that ended after 2 months, also with no response, she received local XRT (3000 cGy) that ended 1 month later. However, by the following month progression had continued. The patient started with IMMU-132 the next month (12 mg/kg; reduced to 6.8 mg/kg; Trop-2 expression 3+), and after two months of IMMU-132, a 38% reduction in target lesions, including a substantial reduction in the main lung lesion occurred (not shown). The patient progressed 3 months later after receiving 12 doses.

These results are significant in that they demonstrate that the anti-Trop-2 ADC was efficacious, even in patients who had failed or progressed after multiple previous therapies. In conclusion, at the dosages used, the primary toxicity was a manageable neutropenia, with few Grade 3 toxicities. IMMU-132 showed evidence of activity (PR and durable SD) in relapsed/refractory patients with triple-negative breast cancer, small cell lung cancer, non-small cell lung cancer, colorectal cancer and esophageal cancer, including patients with a previous history of relapsing on topoisomerase-I inhibitor therapy. These results show efficacy of the anti-Trop-2 ADC in a wide range of cancers that are resistant to existing therapies.

Example 9. Comparative Efficacy of Different Anti-Trop-2 ADCs

The therapeutic efficacy of a murine anti-Trop-2 monoclonal antibody (162-46.2) conjugated with SN-38 was compared to sacituzumab govitecan antibody-drug conjugate (ADC) in mice bearing human gastric carcinoma xenografts (NCI-N87). NCI-N87 cells were expanded in tissue culture and harvested with trypsin/EDTA. Female athymic nude mice were injected s.c. with 200 μL of NCI-N87 cell suspension mixed 1:1 with matrigel such that $1\times10^7$ cells was administered to each mouse. Once tumors reached approximately 0.25 cm$^3$ in size (6 days later), the animals were divided up into seven different treatment groups of nine mice each. For the SN-38 ADCs, mice received 500 μg i.v. injections once a week for two weeks. Control mice received the non-tumor targeting hA20-SN-38 ADC at the same dose/schedule. A final group of mice received only saline and served as the untreated control. Tumors were measured and mice weighed twice a week. Mice were euthanized for disease progression if their tumor volumes exceeded 1.0 cm$^3$ in size.

Mean tumor volumes were determined for the SN-38-ADC treated mice (not shown). As determined by area under the curve (AUC), both sacituzumab govitecan and 162-46.2-SN-38 significantly inhibited tumor growth when compared to saline and hA20-SN-38 control mice (P<0.001). Treatment with sacituzumab govitecan achieved stable disease in 7 of 9 mice with mean time to tumor progression (TTP) of 18.4±3.3 days. Mice treated with 162-46.2-SN-38 achieved a positive response in 6 of 9 mice with the remaining 3 achieving stable disease. Mean TTP was 24.2±6.0 days, which is significantly longer than sacituzumab govitecan treated animals (P=0.0382).

These results confirm the in vivo efficacy of different anti-Trop-2 ADCs for treatment of human gastric carcinoma.

Example 10. Treatment of Patients with Advanced, Metastatic Pancreatic Cancer with Anti-Trop-2 ADC Summary IMMU-132 (sacituzumab govitecan) is an anti-Trop-2 ADC comprising the cancer cell internalizing, humanized, anti-Trop-2 hRS7 antibody, conjugated by a pH-sensitive linker to SN-38, the active metabolite of irinotecan, at a mean drug-antibody ratio of 7.6. Trop-2 is a type-I transmembrane, calcium-transducing protein expressed at high density, frequency, and specificity in many epithelial cancers, including pancreatic ductal adenocarcinoma, with limited normal tissue expression. All 29 pancreatic tumor microarray specimens tested were Trop-2-positive by immunohistochemistry, and human pancreatic cancer cell lines were found to express 115k-891k Trop-2 copies on the cell membrane.

We reported above the results from the IMMU-132 Phase I study enrolling patients with 13 different tumor types using a 3+3 design. The Phase I dose-limiting toxicity was neutropenia. Over 80% of 24 assessable patients in this study had long-term stable disease, with partial responses (RECIST) observed in patients with colorectal (CRC), triple-negative breast (TNBC), small-cell and non-small cell lung (SCLC, NSCLC), and esophageal (EAC) cancers. The present Example reports the results from the IMMU-132 Phase I/II study cohort of patients with metastatic PDC. Patients with PDC who failed a median of 2 prior therapies (range 1-5) were given IMMU-132 on days 1 and 8 in repeated 21-day cycles.

In the subgroup of PDC patients (N=15), 14 received prior gemcitabine-containing regimens. Initial toxicity data from 9 patients found neutropenia [3 of 9≥G3, 33%; and 1 case of G4 febrile neutropenia), which resulted in dose delays or dose reductions. Two patients had Grade 3 diarrhea; no patient had Grade 3-4 nausea or vomiting. Alopecia (Grades 1-2) occurred in 5 of 9 patients. Best response was assessable in 13 of 14 patients, with 8 stable disease for 8 to 21.4 wks (median 12.7 wks; 11.9 wks all 14 patients). One patient who is continuing treatment has not yet had their first CT assessment. Five had progressive disease by RECIST; 1 withdrew after just 1 dose due to clinical progression and was not assessable. Serum CA19-9 titers decreased in 3 of the patients with stable disease by 23 to 72%. Despite multiple administrations, none of the patients developed an antibody response to IMMU-132 or SN-38. Peak and trough serum samples showed that IMMU-132 cleared more quickly than the IgG, which is expected based on the known local release of SN-38 within the tumor cell. Concentrations of SN-38-bound to IgG in peak samples from one patient given 12 mg/kg of IMMU-132 showed levels of 4000 ng/mL, which is 40-times higher than the SN-38 titers reported in patients given irinotecan therapy.

We conclude that IMMU-132 is active (long-term stable disease) in 62% (8/13) of PDC patients who failed multiple prior therapies, with manageable neutropenia and little GI toxicity. Advanced PDC patients can be given repeated treatment cycles (>6) of 8-10 mg/kg IMMU-132 on days 1 and 8 of a 21-day cycle, with some dose adjustments or growth factor support for neutropenia in subsequent treatment cycles. These results agree with the findings in patients with advanced CRC, TNBC, SCLC, NSCLC, EAC who have shown partial responses and long-term stable disease with IMMU-132 administration. In summary, monotherapy IMMU-132 is a novel, efficacious treatment regimen for patients with PDC, including those with tumors that were previously resistant to other therapeutic regimens for PDC.

Methods and Results

Trop-2 Expression—

The expression of Trop-2 on the surface of various cancer cell lines was determined by flow cytometry using QUANT-BRITE® PE beads. The results for number of Trop-2 molecules detected in the different cell lines was: BxPC-3 pancreatic cancer (891,000); NCI-N87 gastric cancer (383,000); MDA-MB-468 breast cancer (341,000); SK-MES-1 squamous cell lung cancer (27,000); Capan-1 pancreatic cancer (115,000); AGS gastric cancer (78,000) COLO 205 colon cancer (52,000). Trop-2 expression was also observed in 29 of 29 (100%) tissue microarrays of pancreatic adenocarcinoma (not shown).

SN-38 Accumulation—

SN-38 accumulation was determined in nude mice bearing Capan-1 human pancreatic cancer xenografts (~0.06-0.27 g). Mice were injected IV with irinotecan 40 mg/kg (773 µg; Total SN-38 equivalents=448 µg). This dose is MTD in mice. Human dose equivalent=3.25 mg/kg or ~126 mg/m$^2$. Or mice were injected IV with IMMU-132 1.0 mg (SN-38:antibody ratio=7.6; SN-38 equivalents=20 µs). This dose is well below the MTD in mice. Human equivalent dose ~4 mg/kg IMMU-132 (=80 µs/kg SN-38 equivalents). Necropsies were performed on 3 animals per interval, in irinotecan injected mice at 5 min, 1, 2, 6 and 24 hours or in IMMU-132 injected mice at 1, 6, 24, 48 and 72 h. Tissues were extracted and analyzed by reversed-phase HPLC analysis for SN-38, SN-38G, and irinotecan. Extracts from IMMU-132-treated animals also were acid hydrolyzed to release SN-38 from the conjugate (i.e., SN-38 (TOTAL]). The results demonstrate that the IMMU-132 ADC has the potential to deliver 120 times more SN-38 to the tumor compared to irinotecan, even though 22-fold less SN-38 equivalents were administered with the ADC (not shown).

IMMU-132 Clinical Protocol

The protocol used in the phase I/II study was as indicated in Table 5 below.

TABLE 5

Clinical Protocol Using IMMU-132: OVERVIEW

| | |
|---|---|
| Dosing regimen | Once weekly for 2 weeks administered every 21 days for up to 8 cycles. Patients with objective responses are allowed to continue beyond 8 cycles. In the initial enrollment, the planned dose was delayed and reduced if ≥ Grade 2 treatment-related toxicity; protocol was amended later in study to dose delay and reduction only in the event of ≥ Grade 3 toxicity. The development of severe toxicities due to treatment requires dose reduction by 25% of the assigned dose for 1$^{st}$ occurrence, 50% for 2$^{nd}$ occurrence, and treatment discontinued entirely in the event of a 3$^{rd}$ occurrence. |
| Dose level cohorts | 8, 12, 18 mg/kg; later reduced to an intermediate dose level of 10 mg/kg. |
| Cohort size | Standard Phase I [3 + 3] design; expansion includes 15 patients in select cancers. |
| DLT | Grade 4 ANC ≥7 d; ≥ Grade 3 febrile neutropenia of any duration; Grade 4 Platelets ≥5 d; Grade 4 Hgb; Grade 4 N/V/D of any duration or any Grade 3 N/V/D for >48 h; Grade 3 infusion-related reactions; ≥ Grade 3 non-heme toxicity at least possibly due to study drug. |

TABLE 5-continued

Clinical Protocol Using IMMU-132: OVERVIEW

| | |
|---|---|
| Maximum Acceptable Dose (MAD) | Maximum dose where ≥2/6 patients tolerate the full 21-d treatment cycle without dose delay or reduction or ≥ Grade 3 toxicity. |
| Patients | Metastatic colorectal, pancreas, gastric, esophageal, lung (NSCLC, SCLC), triple-negative breast, prostate, ovarian, renal, urinary bladder, head and neck, hepatocellular. Refractory/relapsed after standard treatment regimens for metastatic cancer. Prior irinotecan-containing therapy NOT required for enrollment. No bulky lesion >5 cm. Must be 4 weeks beyond any major surgery, and 2 weeks beyond radiation or chemotherapy regimen. Gilbert's disease or known CNS metastatic disease are excluded. |

Patients were administered IMMU-132 according to the protocol summarized above. An exemplary case study is as follows. A 34 y/o white male initially diagnosed with metastatic pancreatic cancer (liver) had progressed on multiple chemotherapy regimens, including gemcitabine/Erlotinib/FG-3019, FOLFIRINOX and GTX prior to introduction of IMMU-132 (8 mg/kg dose given days 1 and 8 of a 21 day cycle). The patient received the drug for 4 mo with good symptomatic tolerance, an improvement in pain, a 72% maximum decline in CA19-9 (from 15885 U/mL to 4418 U/mL) and stable disease by CT RECIST criteria along with evidence of tumor necrosis. Therapy had to be suspended due to a liver abscess; the patient expired ~6 weeks later, 6 mo following therapy initiation.

Conclusions

Preclinical studies indicated that IMMU-132 delivers 120-times the amount of SN-38 to a human pancreatic tumor xenograft than when irinotecan is given. As part of a larger study enrolling patients with diverse metastatic solid cancers, the Phase 2 dose of IMMU-132 was determined to be 8 to 10 mg/kg, based on manageable neutropenia and diarrhea as the major side effects. No anti-antibody or anti-SN-38 antibodies have been detected to-date, even with repeated therapeutic cycles.

A study of 14 advanced PDC patients who relapsed after a median of 2 prior therapies showed CT-confirmed antitumor activity consisting of 8/13 (62%) with stable disease. Median duration of TTP for 13 CT assessable pts was 12.7 weeks compared to 8.0 weeks estimated from last prior therapy. This ADC, with a known drug of nanomolar toxicity, conjugated to an antibody targeting Trop-2 prevalent on many epithelial cancers, by a linker affording cleavage at the tumor site, represents a new efficacious strategy in pancreatic cancer therapy with ADCs. In comparison to the present standard of care for pancreatic cancer patients, the extension of time to progression in pancreatic cancer patients, particularly in those resistant to multiple prior therapies, was surprising and could not have been predicted.

Example 11. Combining Antibody-Targeted Radiation (Radioimmunotherapy) and Anti-Trop-2-SN-38 ADC Improves Pancreatic Cancer Therapy We previously reported effective anti-tumor activity in nude mice bearing human pancreatic tumors with $^{90}$Y-humanized PAM4 IgG (hPAM4; $^{90}$Y-clivatuzumab tetraxetan) that was enhanced when combined with gemcitabine (GEM) (Gold et al., Int J. Cancer 109:618-26, 2004; Clin Cancer Res 9:3929S-37S, 2003). These studies led to clinical testing of fractionated $^{90}$Y-hPAM4 IgG combined with GEM that is showing encouraging objective responses. While GEM is known for its radiosensitizing ability, alone it is not a very effective therapeutic agent for pancreatic cancer and its dose is limited by hematologic toxicity, which is also limiting for $^{90}$Y-hPAM4 IgG.

As discussed in the Examples above, an anti-Trop-2 ADC composed of hRS7 IgG linked to SN-38 shows anti-tumor activity in various solid tumors. This ADC is very well tolerated in mice (e.g., ≥60 mg), yet just 4.0 mg (0.5 mg, twice-weekly×4) is significantly therapeutic. Trop-2 is also expressed in most pancreatic cancers.

The present study examined combinations of $^{90}$Y-hPAM4 IgG with sacituzumab govitecan in nude mice bearing 0.35 cm$^3$ subcutaneous xenografts of the human pancreatic cancer cell line, Capan-1. Mice (n=10) were treated with a single dose of $^{90}$Y-hPAM4 IgG alone (130 µCi, i.e., the maximum tolerated dose (MTD) or 75 µCi), with sacituzumab govitecan alone (as above), or combinations of the 2 agents at the two $^{90}$Y-hPAM4 dose levels, with the first ADC injection given the same day as the $^{90}$Y-hPAM4. All treatments were tolerated, with ≤15% loss in body weight. Objective responses occurred in most animals, but they were more robust in both of the combination groups as compared to each agent given alone. All animals in the 0.13-mCi $^{90}$Y-hPAM4 IgG+sacituzumab govitecan group achieved a tumor-free state within 4 weeks, while other animals continued to have evidence of persistent disease. These studies provide the first evidence that combined radioimmunotherapy and ADC enhances efficacy at safe doses.

In the ongoing PAM4 clinical trials, a four week clinical treatment cycle is performed. In week 1, subjects are administered a dose of $^{111}$In-hPAM4, followed at least 2 days later by gemcitabine dose. In weeks 2, 3 and 4, subjects are administered a $^{90}$Y-hPAM4 dose, followed at least 2 days later by gemcitabine (200 mg/m$^2$). Escalation started at 3×6.5 mCi/m$^2$. The maximum tolerated dose in front-line pancreatic cancer patients was 3×15 mCi/m$^2$ (hematologic toxicity is dose-limiting). Of 22 CT-assessable patients, the disease control rate (CR+PR+SD) was 68%, with 5 (23%) partial responses and 10 (45%) having stabilization as best response by RECIST criteria.

Preparation of Antibody-Drug Conjugate (ADC)

The SN-38 conjugated hRS7 antibody was prepared as described above and according to previously described protocols (Moon et al. J Med Chem 2008, 51:6916-6926; Govindan et al., Clin Cancer Res 2009. 15:6052-6061). A reactive bifunctional derivative of SN-38 (CL2A-SN-38) was prepared. The formula of CL2A-SN-38 is (maleimido-[x]-Lys-PABOCO-20-O-SN-38, where PAB is p-aminobenzyl and 'x' contains a short PEG). Following reduction of disulfide bonds in the antibody with TCEP, the CL2A-SN-38 was reacted with reduced antibody to generate the SN-38 conjugated RS7.

$^{90}$Y-hPAM4 is prepared as previously described (Gold et al., Clin Cancer Res 2003, 9:3929S-37S; Gold et al., *Int J Cancer* 2004, 109:618-26).

Combination RAIT+ADC

The Trop-2 antigen is expressed in most epithelial cancers (lung, breast, prostate, ovarian, colorectal, pancreatic) and sacituzumab govitecan conjugates are being examined in various human cancer-mouse xenograft models. Initial clinical trials with $^{90}$Y-hPAM4 IgG plus radiosensitizing amounts of GEM are encouraging, with evidence of tumor shrinkage or stable disease. However, therapy of pancreatic cancer is very challenging. Therefore, a combination therapy was examined to determine whether it would induce a better response. Specifically, administration of sacituzumab govitecan at effective, yet non-toxic doses was combined with RAIT with $^{90}$Y-hPAM4 IgG.

The results demonstrated that the combination of sacituzumab govitecan with $^{90}$Y-hPAM4 was more effective than either treatment alone, or the sum of the individual treatments (not shown). At a dosage of 75 µCi $^{90}$Y-hPAM4, only 1 of 10 mice was tumor-free after 20 weeks of therapy (not shown), the same as observed with sacituzumab govitecan alone (not shown). However, the combination of sacituzumab govitecan with $^{90}$Y-hPAM4 resulted in 4 of 10 mice that were tumor-free after 20 weeks (not shown), and the remaining subjects showed substantial decrease in tumor volume compared with either treatment alone (not shown). At 130 µCi $^{90}$Y-hPAM4 the difference was even more striking, with 9 of 10 animals tumor-free in the combined therapy group compared to 5 of 10 in the RAIT alone group (not shown). These data demonstrate the synergistic effect of the combination of sacituzumab govitecan with $^{90}$Y-hPAM4. RAIT+ADC significantly improved time to progression and increased the frequency of tumor-free treatment. The combination of ADC with sacituzumab govitecan added to the MTD of RAIT with $^{90}$Y-hPAM4 had minimal additional toxicity, indicated by the % weight loss of the animal in response to treatment (not shown).

The effect of different sequential treatments on tumor survival indicated that the optimal effect is obtained when RAIT is administered first, followed by ADC (not shown). In contrast, when ADC is administered first followed by RAIT, there is a decrease in the incidence of tumor-free animals (not shown). Neither unconjugated hPAM4 nor hRS7 antibodies had anti-tumor activity when given alone (not shown).

Example 12. Use of Sacituzumab Govitecan (IMMU-132) to Treat Therapy-Refractive Metastatic Breast Cancer The patient was a 57-year-old woman with stage IV, triple-negative, breast cancer (ER/PR negative, HER-neu negative), originally diagnosed in 2005. She underwent a lumpectomy of her left breast in 2005, followed by Dose-Dense ACT in adjuvant setting in September 2005. She received radiation therapy, which was completed in November. Local recurrence of the disease was identified when the patient palpated a lump in the contralateral (right) breast in early 2012, and was then treated with CMF (cyclophosphamide, methotrexate, 5-fluorouracil) chemotherapy. Her disease recurred in the same year, with metastatic lesions in the skin of the chest wall. She then received a carboplatin+ TAXOL® chemotherapy regimen, during which thrombocytopenia resulted. Her disease progressed and she was started on weekly doxorubicin, which was continued for 6 doses. The skin disease also was progressing. An FDG-PET scan on Sep. 26, 2012 showed progression of disease on the chest wall and enlarged, solid, axillary nodes. The patient was given oxycodone for pain control.

She was given IXEMPRA® from October 2012 until February 2013 (every 2 weeks for 4 months), when the chest wall lesion opened up and bled. She was then put on XELODA®, which was not tolerated well due to neuropathy in her hands and feet, as well as constipation. The skin lesions were progressive and then she was enrolled in the IMMU-132 trial after giving informed consent. The patient also had a medical history of hyperthyroidism and visual disturbances, with high risk of CNS disease (however, brain MRI was negative for CNS disease). At the time of enrollment to this trial, her cutaneous lesions (target) in the right breast measured 4.4 cm and 2.0 cm in the largest diameter. She had another non-target lesion in the right breast and one enlarged lymph node each in the right and left axilla.

The first IMMU-132 infusion (12 mg/kg) was started on Mar. 12, 2013, which was tolerated well. Her second infusion was delayed due to Grade 3 absolute neutrophil count (ANC) reduction (0.9) on the scheduled day of infusion, one week later. After a week delay and after receiving NEULASTA®, her second IMMU-132 was administered, with a 25% dose reduction at 9 mg/kg. Thereafter she has been receiving IMMU-132 on schedule as per protocol, once weekly for 2 weeks, then one week off. Her first response assessment on May 17, 2013, after 3 therapy cycles, showed a 43% decrease in the sum of the long diameter of the target lesions, constituting a partial response by RECIST criteria. She is continuing treatment at the 9 mg/kg dose level. Her overall health and clinical symptoms improved considerably since she started treatment with IMMU-132.

Example 13. Use of Sacituzumab Govitecan (IMMU-132) to Treat Refractory, Metastatic, Small-Cell Lung Cancer This is a 65-year-old woman with a diagnosis of small-cell lung cancer, involving her left lung, mediastinal lymph nodes, and MRI evidence of a metastasis to the left parietal brain lobe. Prior chemotherapy includes carboplatin, etoposide, and topotecan, but with no response noted. Radiation therapy also fails to control her disease. She is then given IMMU-132 at a dose of 18 mg/kg once every three weeks for a total of 5 infusions. After the second dose, she experiences hypotension and a Grade 2 neutropenia, which improve before the next infusion. After the fifth infusion, a CT study shows 13% shrinkage of her target left lung mass. MRI of the brain also shows a 10% reduction of this metastasis. She continues her IMMU-132 dosing every 3 weeks for another 3 months, and continues to show objective and subjective improvement of her condition, with a 25% reduction of the left lung mass and a 21% reduction of the brain metastasis.

Example 14. Therapy of a Gastric Cancer Patient with Stage IV Metastatic Disease with Sacituzumab Govitecan (IMMU-132)

This patient is a 60-year-old male with a history of smoking and periods of excessive alcohol intake over a 40-year-period. He experiences weight loss, eating discomfort and pain not relieved by antacids, frequent abdominal pain, lower back pain, and most recently palpable nodes in both axilla. He seeks medical advice, and after a workup is shown to have an adenocarcinoma, including some squamous features, at the gastro-esophageal junction, based on biopsy via a gastroscope. Radiological studies (CT and FDG-PET) also reveal metastatic disease in the right and left axilla, mediastinal region, lumbar spine, and liver (2 tumors in the right lobe and 1 in the left, all measuring between 2 and 4 cm in diameter). His gastric tumor is resected and he is then put on a course of chemotherapy with epirubicin, cisplatin, and 5-fluorouracil. After 4 months and a rest period of 6 weeks, he is switched to docetaxel chemotherapy, which also fails to control his disease, based on progression confirmed by CT measurements of the metastatic tumors and some general deterioration.

The patient is then given therapy with IMMU-132 (hRS7-SN-38) at a dose of 10 mg/kg infused every-other-week for a total of 6 doses, after which CT studies are done to assess status of his disease. These infusions are tolerated well, with some mild nausea and diarrhea, controlled with symptomatic medications. The CT studies reveal that the sum of his index metastatic lesions has decreased by 28%, so he continues on this therapy for another 5 courses. Follow-up CT studies show that the disease remains about 35% reduced by RECIST criteria from his baseline measurements prior to IMMU-132 therapy, and his general condition also appears to have improved, with the patient regaining an optimistic attitude toward his disease being under control.

Example 15. Clinical Trials of IMMU-132 in Diverse Trop-2 Positive Cancers

Abstract

Sacituzumab govitecan (IMMU-132, also known as hRS7-CL2A-SN-38) is an antibody-drug conjugate (ADC) targeting Trop-2, a surface glycoprotein expressed on many epithelial tumors, for delivery of SN-38, the active metabolite of irinotecan. Unlike most ADCs that use ultratoxic drugs and stable linkers, IMMU-132 uses a moderately toxic drug with a moderately stable carbonate bond between SN-38 and the linker. Flow cytometry and immunohistochemistry disclosed Trop-2 is expressed in a wide range of tumor types, including gastric, pancreatic, triple-negative breast (TNBC), colonic, prostate, and lung. While cell-binding experiments reveal no significant differences between IMMU-132 and parental hRS7 antibody, surface plasmon resonance analysis using a Trop-2 CM5 chip shows a significant binding advantage for IMMU-132 over hRS7. The conjugate retained binding to the neonatal receptor, but lost greater than 60% of the antibody-dependent cell-mediated cytotoxicity activity compared to hRS7.

Exposure of tumor cells to either free SN-38 or IMMU-132 demonstrated the same signaling pathways, with pJNK1/2 and p21WAF1/Cip1 up-regulation followed by cleavage of caspases 9, 7, and 3, ultimately leading to poly-ADP-ribose polymerase cleavage and double-stranded DNA breaks. Pharmacokinetics of the intact ADC in mice reveals a mean residence time (MRT) of 15.4 h, while the carrier hRS7 antibody cleared at a similar rate as unconjugated antibody (MRT=~300 h). IMMU-132 treatment of mice bearing human gastric cancer xenografts (17.5 mg/kg; twice weekly×4 weeks) resulted in significant anti-tumor effects compared to mice treated with a non-specific control. Clinically relevant dosing schemes of IMMU-132 administered either every other week, weekly, or twice weekly in mice bearing human pancreatic or gastric cancer.

The present Phase I trial evaluated this ADC as a potential therapeutic for pretreated patients with a variety of metastatic solid cancers. In particular embodiments, the therapy is of use to treat patients who had previously been found to be resistant to, or had relapsed from, standard anti-cancer treatments, including but not limited to treatment with irinotecan, the parent compound of SN-38. These results were surprising and unexpected and could not have been predicted.

Sacituzumab govitecan was administered on days 1 and 8 of 21-day cycles, with cycles repeated until dose-limiting toxicity or progression. Dose escalation followed a standard 3+3 scheme with 4 planned dose levels and dose delay or reduction allowed. Twenty-five patients (52-60 years old, 3 median prior chemotherapy regimens) were treated at dose levels of 8 (N=7), 10 (N=6), 12 (N=9), and 18 (N=3) mg/kg. Neutropenia was dose-limiting, with 12 mg/kg the maximum tolerated dose for cycle 1, but too toxic with repeated cycles. Lower doses were acceptable for extended treatment with no treatment-related grade 4 toxicities and grade 3 toxicities limited to fatigue (N=3), neutropenia (N=2), diarrhea (N=1), and leukopenia (N=1). Using CT-based RECIST 1.1 criteria, 3 patients achieved partial responses (triple-negative breast cancer, small-cell lung cancer, colon cancer) and 15 others had stable disease as best response; of these, 12 maintained disease control with continued treatment for 16-36 weeks. No pre-selection of patients based on tumor Trop-2 expression was undertaken.

It was concluded that sacituzumab govitecan is a promising ADC conjugate with acceptable toxicity and encouraging therapeutic activity in patients with difficult-to-treat cancers. The 8 and 10 mg/kg doses were selected for Phase II studies.

INTRODUCTION

Two new antibody-drug conjugates (ADCs) incorporating different ultratoxic (picomolar potency) drugs have been approved, leading to further development of other ADCs based on similar principles, including use of ultratoxic drugs (Younes et al., 2011, Nat Rev Drug Discov 11:19-20; Sievers & Senter, 2013, Ann Rev Med 64:15-29; Krop & Winer, 2014, Clin Cancer Res 20:15-20). Alternatively, Moon et al. (2008, J Med Chem 51:6916-26) and Govindan et al. (2009, Clin Cancer Res 15:6052-61) selected SN-38, a topoisomerase I inhibitor that is the active metabolite of irinotecan, an approved drug with well-known but complex pharmacology (Mathijssen et al., 2001, Clin Cancer Res 7:2182-94). Several linkers for conjugating SN-38 were evaluated for release from the IgG at varying rates, from several hours to days (Moon et al., 2008, J Med Chem 51:6916-26; Govindan et al., 2009, Clin Cancer Res 15:6052-61; Cardillo et al., 2011, Clin Cancer Res 17:3157-69). The optimal linker that was selected, designated CL2A, exhibiting an intermediate conjugate stability in serum, was attached to the hydroxyl group on SN-38's lactone ring, thereby protecting this ring from opening to the less toxic carboxylate form while bound to the linker, and contained a short polyethylene glycol moiety to enhance solubility (Cardillo et al., 2011, Clin Cancer Res 17:3157-69). The active form of SN-38 was liberated when the carbonate bond between the linker and SN-38 was cleaved, which occurred at low pH, such as that found in lysosomes, as well as the tumor microenvironment, or possibly through enzymatic degradation.

The antibody chosen for this ADC targeted a tumor-associated antigen, Trop-2 (trophoblast cell-surface antigen) (Cardillo et al., 2011, Clin Cancer Res 17:3157-69), using the humanized RS7 monoclonal antibody that was shown previously to internalize (Stein et al., 1993, Int J Cancer 55:938-46. Trop-2 is an important tumor target for an ADC, because it is over-expressed on many epithelial tumors, particularly more aggressive types (Ambrogi et al., 2014, PLoS One 9:e96993; Cubas et al., 2009, Biochim Biophys Act 1796:309-14; Trerotola et al., 2013, Oncogene 32:222-33). Trop-2 is also present on a number of normal tissues, but preclinical studies in monkeys that express the antigen observed only dose-limiting neutropenia and diarrhea with this new ADC, with no evidence of appreciable toxicity to the Trop-2-expressing normal tissues (Cardillo et al., 2011, Clin Cancer Res 17:3157-69). Therefore, with preclinical data demonstrating activity in several human tumor xenograft models and showing a high therapeutic window (Cardillo et al., 2011, Clin Cancer Res 17:3157-69), a Phase I clinical trial was initiated to determine the maximum tolerated and optimal doses of this novel ADC in heavily-pretreated patients with diverse, relapsed/refractory, metastatic epithelial tumors. This trial was registered at ClinicalTrials.gov (NCT01631552).

Materials and Methods

Entry Criteria—

The primary objective was to determine the safety and tolerability of sacituzumab govitecan (IMMU-132) as a single agent. The trial was designed as a standard 3+3 Phase I design, starting at a dose of 8 mg/kg per injection, with dosages given weekly for 2 weeks in a 3-week treatment cycle.

Male and non-pregnant, non-lactating females ≥18 years of age were eligible if they had a diagnosis of one of thirteen different types of epithelial tumors. Although no pre-selection based on Trop-2 expression was required, these tumors are expected to have Trop-2 expression in >75% of the cases based on immunohistology studies on archival specimens. Patients were required to have measurable metastatic disease (no single lesions ≥5 cm) and had relapsed or were refractory to at least one approved standard chemotherapeutic regimen for that indication. Other key criteria included adequate (grade ≤1) hematology, liver and renal function, and no known history of anaphylactic reactions to irinotecan, or grade ≥3 gastrointestinal toxicity to prior irinotecan or other topoisomerase-I treatments. Since patients with such diverse diseases were allowed, prior irinotecan therapy was not a prerequisite. Patients with Gilbert's disease or those who had not tolerated previously administered irinotecan or with known CNS metastatic disease were excluded.

Study Design—

Baseline evaluations were performed within 4 weeks of the start of treatment, with regular monitoring of blood counts, serum chemistries, vital signs, and any adverse events. Anti-antibody and anti-SN-38 antibody responses were measured by ELISA, with samples taken at baseline and then prior to the start of every even-numbered treatment cycle. The first CT examination was obtained 6-8 weeks from the start of treatment and then continued at 8- to 12-week intervals until progression. Additional follow-up was required only to monitor any ongoing treatment-related toxicity. Toxicities were graded using the NCI CTCAE version 4.0, and efficacy assessed by RECIST 1.1.

An ELISA to detect Trop-2 in serum was developed that has a sensitivity of 2 ng/mL, but after testing 12 patients and finding no evidence of circulating Trop-2, no further screening was performed. Although not an eligibility criterion, specimens of previously archived tumors were requested for Trop-2 determination by immunohistology, using a goat polyclonal antibody anti-human Trop-2 (R&D Systems, Minneapolis, Minn.), since the epitope recognized by the ADC's antibody, hRS7, is not preserved in formalin-fixed, paraffin-embedded sections (Stein et al., 1993, Int J Cancer 55:938-46). Staining was performed as described below.

Therapeutic Regimen—

Lyophilized sacituzumab govitecan was reconstituted in saline and infused over 2-3 h (100 mg of antibody contained ~1.6 mg of SN-38, with a mean drug:antibody ratio [DAR] of 7.6:1). Prior to the start of each infusion, most patients received acetaminophen, anti-histamines (H1 and H2 blockers), and dexamethasone. Prophylactic use of antiemetics or anti-diarrheal medications was prohibited. Therapy consisted of 2 consecutive doses given on days 1 and 8 of a 3-week treatment cycle, with the intent to allow patients to continue treatment for up to 8 cycles (i.e., 16 treatments) unless there was unacceptable toxicity or progression. Patients showing disease stabilization or response after 8 cycles could continue treatments.

Dose-limiting toxicities (DLT) were considered as grade ≥3 febrile neutropenia of any duration, grade 3 thrombocytopenia with significant bleeding or grade 4 thrombocytopenia ≥5 days, any grade 3 nausea, vomiting or diarrhea that persisted for >48 h despite optimal medical management, or grade 4 (life threatening) nausea, vomiting or diarrhea of any duration, or any other grade ≥3 non-hematologic toxicity at least possibly due to study drug, as well as the occurrence of any grade 3 infusion-related reactions.

The maximum tolerated dose (MTD) was judged on the patient's tolerance to the first treatment cycle. On a scheduled treatment day, any patient with grade ≥2 treatment-related toxicity, with the exception of alopecia, had their treatment delayed in weekly increments for up to 2 weeks. Treatment was reinitiated once toxicity had resolved to grade ≤1. The protocol also initially required all subsequent treatment doses to be reduced (25% if recovered within 1 week, 50% if within 2 weeks), but this was relaxed later in the trial when the protocol was amended to permit supportive care after the first cycle. However, if toxicity did not recover within 3 weeks or worsened, treatment was terminated. Importantly, a dose delay with reduction did not constitute a DLT, and therefore this allowed treatments to continue, but at a lower dose. Therefore, a patient requiring a dose delay/reduction who was able to continue treatment was not considered assessable for DLT, and then replaced.

Since a DLT event resulted in the termination of all further treatments, a secondary objective was to assess a dose level that could be tolerated over multiple cycles of treatment with minimal dose delays or reductions. This dose level was designated the maximum acceptable dose, and required patients to tolerate a given dose level in the first cycle without having a delay or reduction during that cycle and leading up to the start of the second cycle.

Pharmacokinetics and Immunogenicity—

Blood samples were taken within ~30 min from the end of the infusion (e.g., peak) and then prior to each subsequent injection (e.g., trough). Samples were separated and sera frozen for determination of total IgG and sacituzumab govitecan concentrations by ELISA. Serum samples from seven patients also were assayed for SN-38 content, both total (representing SN-38 bound to the IgG and free) and free SN-38 (i.e., unbound SN-38).

Results

Patient Characteristics—

Twenty-five patients were enrolled (Table 6). The median age ranged from 52 to 60 years, with 76% having an ECOG 1 performance status, the remaining ECOG 0. Most patients had metastatic pancreatic cancer (PDC) (N=7), followed by triple-negative breast cancer (TNBC) (N=4), colorectal cancer (CRC) (N=3), small cell lung cancer (SCLC) (N=2), and gastric cancer (GC) (N=2), with single cases of esophageal adenocarcinoma (EAC), hormone-refractory prostate cancer (HRPC), non-small cell lung cancer (NSCLC), epithelial ovarian cancer (EOC), renal, tonsil, and urinary bladder cancers (UBC).

Immunohistology was performed on archival tissues from 17 patients, with 13 (76.4%) having 2+ to 3+ membrane and cytoplasmic staining on >10% of the tumor cells in the specimens; 3 specimens (17.6%) were negative. Several representative cases are disclosed below.

All patients entered the trial with metastatic disease in sites typical for their primary cancer. CT determined that the median sum of the largest tumor diameters for all patients was 9.7 cm (range 2.9 to 29.8 cm), with 14 patients having 3 or more target lesions (over all patients median=4, range 1-10 lesions) and a median of 2 non-target lesions (range=0-7 lesions) identified in their baseline studies. The median number of prior systemic therapies was 3, with 7 patients (2 PDC and GC, 1 each CRC, TNBC, tonsil) having one prior therapy, and 7 having five or more prior therapies; eleven patients had prior radiation therapy. Prior topoisomerase I therapy was given to nine patients, with 2/3 CRC, 4/7 PDC, and 1 patient with EAC receiving irinotecan, and 2/2 patients with SCLC having topotecan, with three of these (2 with SCLC and one with CRC) failing to respond to the anti-topoisomerase 1 therapy. Further, seven of 23 patients (2 undetermined) had responded to their last prior therapy, with a median duration of 3 months (range, 1-11 months).

Nearly all patients received multiple sacituzumab govitecan treatments (median, 10 doses) until there was definitive evidence of disease progression by CT using RECIST 1.1; one patient withdrew because systematic deterioration, and 1 patient did not have their target lesion measured in first follow-up when a new lesion was observed.

TABLE 6

Baseline demographics and disease characteristics (N = 25 patients).

|  | 8 mg/kg | 10 mg/kg | 12 mg/kg | 18 mg/kg |
|---|---|---|---|---|
| M/F | 2/5 | 3/3 | 3/6 | 2/1 |
| Age, y | 52 | 58.5 | 60 | 56 |
| Median (range) | (43-62) | (49-80) | (50-74) | (52-60) |
| ECOG performance status |  |  |  |  |
| 0 | 3 | 1 | 2 | 0 |
| 1 | 1 | 5 | 7 | 3 |
| Tumor Type | N | N | N | N |
| Colorectal | 2 | 1 | 0 | 0 |
| Pancreas | 3 | 1 | 3 | 0 |
| TNBC | 0 | 1 | 2 | 1 |
| SCLC | 0 | 0 | 1 | 1 |
| Other[a] | 2 | 3 | 3 | 1 |
|  | (EOC, GC) | (GC, RCC, Tonsil) | (UBC, NSCLC, HRPC) | (EAC) |
| Trop-2 expression | N | | | |
| 1+ | 1 (TNBC) | | | |
| 2+ | 3 (CRC) | | | |
| 3+ | 10 (2 each of EAC, PDC, TNBC; 1 each of EOC, Tonsil, NSCLC, SCLC) | | | |
| Negative | 3 (1 each of TNBC, Gastric, Renal) | | | |
| Not determined | 8 (5 PDC, 1 each of HRPC, SCLC, UBC) | | | |
| Prior Therapy | N | N | N | N |
| Radiotherapy | 2 | 4 | 3 | 2 |
| Systemic therapy[c] |  |  |  |  |
| 1 | 4 | 2 | 1 | 0 |
| 2 | 0 | 1 | 3 | 1 |
| 3 | 1 | 1 | 0 | 1 |
| 4 | 1 | 0 | 2 | 0 |
| ≥5 | 1 | 2 | 3 | 1 |
| Prior Topoisomerase I inhibitor | 3 | 1 | 4 | 1 |
| Tumor metastases (# patients) | N | N | N | N |
| Target and non-target sites |  |  |  |  |
| Chest/head/neck | 0 | 2 | 4 | 3 |
| Liver[b] | 4 (3) | 4 (2) | 5 (3) | 2 (1) |
| Lungs[b] | 4 (3) | 4 (2) | 4 (3) | 1 (1) |
| Lymph nodes | 3 | 2 | 5 | 2 |
| Abdomen/pelvis | 4 | 3 | 4 | 2 |
| Bone | 1 | 2 | 2 | 1 |
| ≥3 target lesions | 4 | 5 | 5 | 0 |
| Patients treated | 7 | 6 | 9 | 3 |
| Delay/adjustment 1st cycle | 1 | 0 | 5 | 2 |
| Dose-limiting toxicity 1st cycle | 0 | 0 | 0 | 2 |

TABLE 6-continued

Baseline demographics and disease characteristics (N = 25 patients).

|  | 8 mg/kg | 10 mg/kg | 12 mg/kg | 18 mg/kg |
|---|---|---|---|---|
| # treatments at this dose median (range) | 3 (1-31) | 10 (1-31) | 3 (1-8) | 1 (1-2) |
| Total # treatments median (range) | 6 (3-31) | 10 (1-31) | 12 (4-34) | 4 (3-16) |

[a]Other cancers include ovarian (EOC), gastric (GC), urinary bladder (UBC), non-small cell lung cancer (NSCLC), hormone refractory prostate cancer (HRPC), esophageal adenocarcinoma (EAC), renal cell cancer (RCC), and a squamous cell carcinoma of the tonsil.
[b]Number of patients with liver or lung involvement; in parenthesis number of these patients with both liver and lung involvement.
[c]Systemic therapy includes chemotherapy and other forms of therapy, including biologicals and investigational agents.

Dose Assessment—

There were no dose delays or reductions, nor DLT events in the 3 patients (1 CRC, 2 PDC) enrolled at the starting dose level of 8.0 mg/kg. At the next dose level of 12 mg/kg, nine patients were enrolled because of protocol-required delays in administering the second dose were encountered. Five patients experienced a delay in the first cycle (4 had a 1-week delay, with 2 given myeloid growth factor support, and 1 patient having a 2-week delay before being given a second dose). All but 1 of these patients received 12 mg/kg as their second dose. Four of the nine patients at the 12 mg/kg dose level had their third dose that started the second cycle decreased to 9 mg/kg, and the second cycle was delayed 1 additional week in 3 patients. Despite these protocol-required delays/reductions, none of the 9 patients had a dose-limiting event during the first cycle (e.g., 1 patient had disease-related grade 3 hemoglobin after first dose, 2 patients with grade 3 neutropenia after first dose were given myeloid growth factors, 1 had grade 3 neutropenia after first dose that recovered without support, 2 had grade 3 neutropenia after second dose, 2 patients had grade 2 neutropenia after the first or second dose, and 1 patient had no adverse events), and therefore accrual to the 18 mg/kg dose level was allowed. Here, all three patients had dose delays after their first treatment, with only 1 patient receiving the second treatment at 18 mg/kg. Two patients had dose-limiting grade 4 neutropenia, 1 after first dose, the other after the second 18 mg/kg dose, with this latter patient also experiencing grade 2 diarrhea after this dose. Therefore, with 0/9 patients having DLT in the first cycle at 12 mg/kg, this level was declared the MTD.

Additional dose-finding studies continued to refine the dose level that would allow multiple cycles to be given with minimal delay between treatments/cycles. Therefore, 4 more patients were enrolled at the 8 mg/kg dose level, and a new intermediate level of 10 mg/kg was opened. Of the initial three patients enrolled at 8 mg/kg, two CRC patients continued treatment at 8 mg/kg for a total of 31 and 11 treatments, while a PDC patient received three 8 mg/kg doses before dose reduction to 6 mg/kg because of a grade-2 neutropenia on the fourth dose, and then completed 3 more treatments at this level before withdrawing due to disease progression. The additional 4 patients received 3 to 9 doses of 8 mg/kg before withdrawing with disease progression. Two of these patients received only 1 dose before a protocol-required reduction to 6 mg/kg, because of a grade-2 rash and grade-2 neutropenia.

Five of the six patients enrolled at 10 mg/kg received 6 to 30 doses without reduction before withdrawing due to disease progression. One GC patient (#9) developed grade 3 febrile neutropenia as well as grade 4 hemoglobin after receiving 1 dose. While the febrile neutropenia was considered possibly-related to treatment, because it occurred shortly after the first dose, a perforation in the stomach lining was found to likely contribute to the grade 4 hemoglobin, and was considered unrelated. Ultimately, the patient had rapid deterioration and died 4 weeks from the first dose.

Thus, while the overall results supported 12 mg/kg as the MTD, since 8 to 10 mg/kg were better tolerated in the first cycle and permitted repeated cycles with minimal toxicity, Phase II clinical studies are in progress to evaluate these 2 dose levels.

Adverse Events—

There were 297 infusion of sacituzumab govitecan given over 2-3 h, with most investigators electing to pre-medicate prior to each infusion. There were no infusion-related adverse events. While more than half of the patients experienced fatigue, nausea, alopecia, diarrhea, and neutropenia that were considered at least likely related to sacituzumab govitecan treatment; these were mostly grade 1 and 2 (not shown). The most reported grade 3 or 4 toxicity was neutropenia (N=8), but six of these patients were treated initially at 12 and 18 mg/kg. Febrile neutropenia occurred in 2 patients, one was the GC patient #9 already mentioned who received only one 10 mg/kg dose, and a second PDC patient (#19), who had received 4 doses of 12 mg/kg. Diarrhea was mild in most patients, with only three (12%) experiencing grade 3. Two occurred at the 12 mg/kg dose level, 1 after receiving 4 doses, and the other after the first dose, but this patient received 6 more doses at 12 mg/kg with only grade 2 diarrhea reported. Subsequently, both patients were prescribed an over-the-counter anti-diarrheal and treatment continued. There were no other significant toxicities associated with sacituzumab govitecan, but two patients reported a grade 2 rash and 3 patients had a grade 1 pruritus.

Efficacy—

The best response was measured by the change in target lesions and time-to-progression data from patients who had at least one post-treatment CT measurement of their target lesions (not shown). Four patients with disease progression are not represented in the graph, because they did not have a follow-up CT assessment (N=1) or they had new lesions and therefore progressed irrespective of their target lesion status (N=3). Overall, 3 patients had more than a 30% reduction in their target lesions (partial response, PR). Two of these patients (#3 and #15) had confirmatory follow-up CTs, while the third patient (#22) progressed at the next CT performed 12 weeks later. Fifteen patients had stable disease (SD), and 7 progressed (PD) as the best response by RECIST 1.1. The median time to progression from the start of treatment for 24 patients (excluding 1 patient who received only 1 treatment and withdrew) was 3.6 months [range, 1-12.8 months]; 4.1 months (range, 2.6-12.8 months) for all patients with SD or PR (N=18). Of the nine patients who received prior therapy containing a topoisomerase-I inhibitor, two had significant reductions of their target lesions (28% and 38%), 5 had stable disease, including 2 for sustained periods (4.1 and 6.9 months, respectively), whereas 2 progressed at their first assessment.

Comparing TTP with survival of these patients indicates that 16 patients survived from onset of therapy for 15-20 months, including two with a PR (patients 15 (TNBC) and 3 (CRC), and the other four with SD (2 CRC, 1 HRPC, 1 TNBC) (not shown). Radiological responses included 2 patients with >30% reduction in their target lesions (PR) (not shown).

In addition to the 3 patients with PR as best response, there were several notable cases of extended stable disease. A 50-year-old patient with TNBC (patient 18; immunohistology Trop-2 expression=3+) experienced a 13% reduction after just 3 doses, culminating after 16 doses in a 19% reduction in the 4 target lesions (SLD decreased from 7.5 to 6.1 cm), before progressing 45 weeks after starting treatment and receiving 26 doses. A 63-year-old female with CRC (patient 10; immunohistology 2+) with 7 prior treatments, including 3 separate courses of an irinotecan-containing regimens, had an overall 23% reduction in 5 target lesions after receiving 5 doses of 10 mg/kg sacituzumab govitecan, culminating in a maximum 28% reduction after 18 doses. Her plasma CEA decreased to 1.6 ng/mL from a baseline level of 38.5 ng/mL. After receiving 25 doses (27 weeks), she had PD with a 20% increase from the SLD nadir. Interesting, plasma CEA at the time treatment ended was only 4.5 ng/mL. A 68-year-old patient with HRPC (patient 20; no immunohistology) presented with 5 target lesions (13.3 cm) and 5 non-target lesions (3 bone metastases). He received 34 treatments over a period of 12.7 months until progression, with PSA levels increasing gradually over this time. Another notable case was a 52-year-old male with esophageal cancer (patient 25; immunohistology 3+) who had received 6 prior therapies, including 6 months of FOL-FIRI as his $3^{rd}$ course of treatment. Treatment was initiated at 18 mg/kg of sacituzumab govitecan, which was reduced to 13.5 mg/kg because of neutropenia. He had SD over a period of 30 weeks, receiving 15 doses before progressing. A 60-year-old female with PDC (#11) with liver metastases was treated at 10 mg/kg. Her baseline CA19-9 serum titer decreased from 5880 to 2840 units/mL after 8 doses and there was disease stabilization (12% shrinkage as best response) for a period or 15 weeks (11 doses) before a new lesion was discovered. Nevertheless, because CA19-9 remained reduced (2814 units/mL), the patient received another 8 treatments (3 months) at 10 mg/kg before coming off study with progression of her target lesions.

At this time, the potential utility of testing Trop-2 expression in archived samples from this small sampling of 16 patients with diverse cancers is insufficient to allow for a definitive assessment, primarily because most showed elevated expression.

PK and Immunogenicity—

Concentrations of sacituzumab govitecan and IgG in the 30-min serum sample are provided in Table 7, which showed a general trend for the values to increase as the dose increased. In a representative case, a patient with TNBC (#15) received multiple doses, starting at 12 mg/kg, with subsequent reductions over the course of her treatment. Concentrations of the IgG and sacituzumab govitecan in the 30-min serum over multiple doses by ELISA were similar over time (not shown), adjusting lower when the dose was reduced. While residual IgG could be found in the serum drawn immediately before the next dose (trough samples), no sacituzumab govitecan could be detected (not shown).

Total SN-38 concentration in the 30-min serum sample of patient 15 was 3,930 ng/mL after the first dose in cycle 1 (C1D1), but when sacituzumab govitecan treatment was reduced to 9.0 mg/kg for the second dose of the first cycle (C1D2), the level decreased to 2,947 ng/mL (not shown). A further reduction to 2,381 ng/mL was observed in the $6^{th}$ cycle, when the dose was further reduced to 6.0 mg/kg. The amount of free SN-38 in these samples ranged from 88 to 102 ng/mL (2.4% to 3.6% of total SN-38), illustrating that >96% of the SN-38 in the serum in these peak samples was bound to IgG. Twenty-eight 30-min serum samples from 7 patients were analyzed by HPLC, with free SN-38 averaging 2.91±0.91% of the total SN-38 in these samples. Free SN-38G concentrations measured in 4 patients never exceeded SN-38 levels, and were usually several-fold lower.

For example, patient #25 had determinations assessed in the 30-min sample for 12 injections over 8 cycles of treatment. At a starting dose of 18 mg/kg, he had 5,089 ng/mL of SN-38 in the acid-hydrolyzed sample (total SN-38) and just 155.2 ng/mL in the non-hydrolyzed sample (free SN-38; 3.0%). Free SN-38G (glucuronidated form) in this sample was 26.2 ng/mL, or just 14.4% of the total unbound SN-38+ SN-38G in the sample. The patient continued treatment at 13.5 mg/kg, with SN-38 averaging 3309.8±601.8 ng/mL in the 11 remaining peak, acid-hydrolyzed samples, while free SN-38 averaged 105.4±47.7 ng/mL (i.e., 96.8% bound to the IgG), and free SN-38G averaging 13.9±4.1 ng/mL (11.6% of the total SN-38+SN-38G). Importantly, in nearly all of the patients, concentrations of SN-38G in the acid-hydrolyzed and non-hydrolyzed samples were similar, indicating that none of the SN-38 bound to the conjugate was glucuronidated.

TABLE 7

Serum concentration (µg/mL) of intact sacituzumab govitecan (ADC) and hRS7 IgG by ELISA. Assays were performed in samples taken 0.5 h after the first dose.

| | 8 mg/kg | | 10 mg/kg | | 12 mg/kg | | 18 mg/kg | |
|---|---|---|---|---|---|---|---|---|
| | | | | N | | | | |
| | 7 | | 5 | | 9 | | 3 | |
| | IgG | ADC | IgG | ADC | IgG | ADC | IgG | ADC |
| Mean | 193.1 | 141.5 | 203.35 | 185.77 | 239.2 | 183.3 | 409.16 | 258.27 |
| SD | 56.5 | 23.8 | 55.72 | 54.14 | 70.7 | 71.8 | 88.78 | 143.26 |
| Min | 96.0 | 95.0 | 152.00 | 144.00 | 168.9 | 98.0 | 321.48 | 162.80 |
| Max | 249.0 | 169.3 | 285.85 | 237.39 | 400.0 | 311.0 | 499.00 | 423.00 |

None of these patients had a positive baseline level (i.e., >50 ng/mL) or a positive antibody response to either the IgG or SN-38 over their course of treatment.

Discussion

Trop-2 is expressed abundantly in many epithelial tumors, making it an antigen of interest for targeted therapies (Cubas et al., 2009, Biochim Biophys Acta 1796:309-14), especially since it is considered a prognostic marker and oncogene in several cancer types (Cardillo et al., 2011, Clin Cancer Res 17:3157-69; Ambrogi et al., 2014, PLoS One 9:e96993; Cubas et al., 2009, Biochim Biophys Acta 1796:309-14; Trerotola et al., 2013, Oncogene 32:222-33). Although its expression in normal tissues and relationship to another well-studied tumor-associated antigen, EpCam, drew some initial words of caution regarding the safety of developing immunotherapeutics to Trop-2 (Trerotola et al., 2009, Biochim Biophys Acta 1805:119-20), our studies in Cynomolgus monkeys that express Trop-2 in tissues similar to humans indicated sacituzumab govitecan was very well tolerated at a human equivalent dose of ~40 mg/kg (Cardillo et al., 2011, Clin Cancer Res 17:3157-69). At higher doses, animals experienced neutropenia and diarrhea, known side-effects associated with SN-38 derived from irinotecan therapy, yet evidence for significant histopathological changes in Trop-2-expressing normal tissues was lacking (Cardillo et al., 2011, Clin Cancer Res 17:3157-69). Thus, with other preclinical studies finding sacituzumab govitecan was potent at the low nanomolar level and effective in a variety of human epithelial tumor xenografts at non-toxic doses, a phase I trial was undertaken in patients who had failed one or more standard therapies for their diverse metastatic epithelial tumors.

A major finding of this study was that despite using a more conventional drug that is not considered as ultratoxic (drugs active in picomolar range, whereas SN-38 has potency in the low nanomolar range), the sacituzumab govitecan anti-Trop-2-SN-38 conjugate proved clinically to be therapeutically active in a wide range of solid cancers at doses with moderate and manageable toxicity, thus exhibiting a high therapeutic index. A total of 297 doses of sacituzumab govitecan were given to 25 patients without incident; 4 patients received >25 injections. Importantly, no antibody response to the hRS7 IgG or SN-38 was detected, even in patients with multiple cycles of treatment for up to 12 months. Although Trop-2 is expressed in low quantities in a variety of normal tissues (Cardillo et al., 2011, Clin Cancer Res 17:3157-69), neutropenia was the only dose-limiting toxicity, with myeloid growth factor support used in 2 patients given ≥12 mg/kg of sacituzumab govitecan to expedite recovery and allow continuation of treatment in patients who had exhausted their options for other therapy. While the MTD was declared to be 12 mg/kg, 8.0 and 10.0 mg/kg dose levels were selected for further expansion, since patients were more likely to tolerate additional cycles at these levels with minimal supportive care, and responses were observed at these levels. Only 2 of 13 patients (15.4%) experienced grade-3 neutropenia at these dose levels. The grade 3 and 4 neutropenia incidence for irinotecan monotherapy given weekly or once every 3 weeks in a front- or second-line setting was 14 to 26% (Camptosar—irinotecan hydrochloride injection, solution (prescribing information, package insert) Pfizer, 2012). With sacituzumab govitecan, only 1 patient at the 10 mg/kg dose level had grade-3 diarrhea. This incidence is lower than the 31% of patients given weekly×4 doses of irinotecan who experienced grades 3 and 4 late diarrhea (Camptosar—irinotecan hydrochloride injection, solution (prescribing information, package insert) Pfizer, 2012). Other common toxicities attributed to sacituzumab govitecan included fatigue, nausea, and vomiting, most being grade 1 and 2, as well as alopecia. Two incidents of febrile neutropenia and one of grade 3 deep vein thrombosis also occurred at the 10 and 12 mg/kg dose levels. UGT1A1 monitoring was not initiated until after dose exploration was completed, and therefore an assessment of its contribution to toxicity cannot be reported at this time.

Patients enrolled in this trial were not pre-selected for Trop-2 expression, primarily because immunohistological assessments of tissue microarrays of diverse cancers (such as prostate, breast, pancreas, colorectal, and lung cancers) had indicated the antigen was present in >90% of the specimens (not shown). In addition, Trop-2 was not found in the sera of 12 patients with diverse metastatic cancers, further suggesting that a serum assay would not be useful for patient selection. Although we are attempting to collect archival specimens of the tumors from patients enrolled in the trial, there is insufficient evidence at this time to suggest patient selection based on immunohistological staining will correlate with anti-tumor activity, so no patient enrichment based on Trop-2 expression has been undertaken.

As a monotherapy, sacituzumab govitecan had good anti-tumor activity in patients with diverse metastatic, relapsed/refractory, epithelial tumors, showing appreciable reductions in target lesions by CT, using RECIST1.1 criteria, including sustained disease stabilization. Three (12%) of the 25 patients (1 each of SCLC [after progressing with topotecan], TNBC, and colon cancer) had >30% reductions of their target lesions before progressing 2.9, 4.3, and 7.1 months, respectively, from the onset of therapy. Fifteen patients (60%) had SD, with 9 of these progressing after >4 months from the start of treatment. Responses or disease stabilization occurred in 7 of 9 patients who had prior therapy with a topoisomerase I inhibitor-containing drug or regimen. Three of these failed to respond to their prior topoisomerase I inhibitor therapy (irinotecan or topotecan), yet sacituzumab govitecan was able to induce tumor shrinkage in 2 of them: 13% in a patient with colon cancer and 38% in the other with SCLC. Thus, sacituzumab govitecan may be therapeutically active in those who failed or relapsed to a prior topoisomerase I-containing regimen, which should be examined further in the Phase II expansion study.

Although the largest number of patients enrolled in this trial had advanced pancreatic ductal cancer (N=7; median time to progression 2.9 months]; range, 1.0 to 4.0 months), even in this difficult-to-treat disease, there have been encouraging reductions in target lesions and CA19-9 serum concentrations to suggest activity (Picozzi et al., 2014, presented at the AACR Special Conference "Pancreatic Cancer: Innovations in Research and Treatment, New Orleans, La. USA, p. B99). However, responses in patients with TNBC and SCLC are of particular interest, given the need for targeted therapies in these indications. Indeed, additional partial responses in patients with TNBC (Goldenberg et al., 2014, presented at the AACR San Antonio Breast cancer Symposium, San Antonio, Tex.) and SCLC (Goldenberg et al., 2014, Sci Transl Med) observed in the on-going expansion phase of this trial have suggested further emphasis on these cancers, but encouraging responses in NSCLC, EAC, UBC, and CRC are also being followed. Indeed, in a recent update of the on-going trial of sacituzumab govitecan, in 17 TNBC patients studied to date, an overall response rate (PR) of 29%, with 46% clinical benefit rate (PR+SD≥6 months) has been observed. Long-term survival (15-20 months) was observed for almost 25% (6/25) of the patients studied, and included 2 with PRs and 4 with SD, including patients with TNBC (N=2), CRC (N=3), and HRPC (N=1).

Analysis of the serum samples 30 min after the end of infusion showed >96% of the SN-38 was bound to the IgG. More detailed pharmacokinetics will be available when the phase II portion of the trial is completed. HPLC analysis also detected only trace amounts of free SN-38G in the serum, whereas with irinotecan therapy the AUC for the less active SN-38G is >4.5-fold higher than SN-38 (Xie et al., 2002, J Clin Oncol 20:3293-301). Comparison of SN-38 delivery in tumor-bearing animals given sacituzumab govitecan and irinotecan has indicated the SN-38 bound to the IgG is not glucuronidated, whereas in animals given irinotecan, >50% of the total SN-38 in the serum is glucuronidated (Goldenberg et al., 2014, J Clin Oncol 32:Abstract 3107). More importantly, analysis of SN-38 concentrations were ~135-fold higher in Capan-1 human pancreatic cancer xenografts given sacituzumab govitecan than irinotecan (Goldenberg et al., 2014, Sci Transl Med). Thus, sacituzumab govitecan has several distinct advantage over non-targeted forms of topoisomerase-I inhibitors: (i) a mechanism that selectively retains the conjugate in the tumor (anti-Trop-2 binding), and (ii) the targeted SN-38 also appears to be fully protected (i.e., not glucuronidated and in the lactone form), such that any SN-38 accreted by the tumor cells either by the direct internalization of the conjugate or through its release into the tumor microenvironment from the conjugate bound to the tumor will be in its most potent form. These results suggest that a moderately-toxic, but well understood, cytotoxic agent, SN-38, can be effective as part of a tumor-targeting ADC, such as sacituzumab govitecan. But by administering an ADC with a moderately-toxic drug conjugated at a high drug:antibody ratio (7.6:1), higher concentrations of SN-38 can be delivered to the cancers targeted, as suggested in the improved concentration of SN-38 achieved with sacituzumab govitecan compared to that released from irinotecan.

In conclusion, this phase I experience has shown that sacituzumab govitecan was tolerated with moderate and manageable toxicity, all related to the activity of SN-38, with no evidence of damage to normal tissues known to contain Trop-2. Importantly, sacituzumab govitecan was active in patients with diverse metastatic solid tumors, even after failing prior therapy with topoisomerase-I inhibitors. Thus, it appears from this initial experience that sacituzumab govitecan has a high therapeutic index, even in patients with tumors not known to be responsive to topoisomerase I inhibitors, such as SCLC and TNBC. This clinical trial is continuing, focusing on starting doses of 8 and 10 mg/kg in patients with TNBC, SCLC, and other Trop-2$^+$ cancers.

Example 16. Use of IMMU-132 in Triple Negative Breast Cancer (TNBC)

The Trop-2/TACSTD2 gene has been cloned (Fomaro et al., 1995, Int J Cancer 62:610-18) and found to encode a transmembrane $Ca^{++}$-signal transducer (Basu et al., 1995, Int J Cancer 62:472-72; Ripani et al., 1998, Int J Cancer 76:671-76) functionally linked to cell migration and anchorage-independent growth, with higher expression in a variety of human epithelial cancers, including breast, lung, gastric, colorectal, pancreatic, prostatic, cervical, head-and-neck, and ovarian carcinomas, compared to normal tissues (Cardillo et al., 2011, Clin Cancer Res 17:3157-69; Stein et al., 1994; Int J Cancer Suppl 8:98-102; Cubas et al., 2009, Biochim Biophys Acta 196:309-14; Trerotola et al., 2013, Oncogene 32:222-33). The increased expression of Trop-2 has been reported to be necessary and sufficient for stimulation of cancer growth (Trerotola et al., 2013, Oncogene 32:222-33), while a bi-cistronic cyclin D1-Trop-2 mRNA chimera is an oncogene (Guerra et al., 2008, Cancer Res 68:8113-21). Importantly, elevated expression has been associated with more aggressive disease and a poor prognosis in several cancer types (Cubas et al., 2009, Biochim Biophys Acta 196:309-14; Guerra et al., 2008, Cancer Res 68:8113-21; Bignotti et al., 2010, Eur J Cancer 46:944-53; Fang et al., 2009, Int J Colorectal Dis 24:875-84; Muhlmann et al., 2009, J Clin Pathol 62:152-58), including breast cancer (Ambrogi et al., 2014, PLoS One 9:e96993; Lin et al., 2013, Exp Mol Pathol 94:73-8). Increased Trop-2 mRNA is a strong predictor of poor survival and lymph node metastasis in patients with invasive ductal breast cancers, and Kaplan-Meier survival curves showed that breast cancer patients with high Trop-2 expression had a significantly shorter survival (Lin et al., 2013, Exp Mol Pathol 94:73-8).

Methods

DAR Determination by HIC—

Clinical lots of IMMU-132 were analyzed by hydrophobic interaction chromatography (HIC) using a butyl-NPR HPLC column (Tosoh Bioscience, King of Prussia, Pa.). IMMU-132 injections (100 µg) were resolved with a 15-min linear gradient of 2.25-1.5 M NaCl in 25 mM sodium phosphate, pH 7.4, run at 1 mL/min and room temperature.

DAR Determination by LC-MS—

Because the interchain disulfides are reduced and the resulting sulfhydryl groups are used for drug conjugation (or blocked), the heavy and light chains resolved during LC-MS analysis without addition of reducing agents, and were analyzed independently. Different lots of IMMU-132 were injected on an Agilent 1200 series HPLC using an Aeris Widepore C4 reverse-phase HPLC column (3.6 µM, 50×2.1 mm) and resolved by reverse phase HPLC with a14-min linear gradient of 30-80% acetonitrile in 0.1% formic acid. Electrospray ionization time of flight (ESI-TOF) mass spectrometry was accomplished with an in-line Agilent 6210 ESI-TOF mass spectrometer with Vcap, fragmentor and skimmer set to 5000V, 300V and 80V, respectively. The entire RP-HPLC peak representing all kappa or heavy chain species were used to generate deconvoluted mass spectra.

Cell Lines—

All human cancer cell lines used in this study were purchased from the American Type Culture Collection (Manassas, Va.), except where noted, and all were authenticated by short tandem repeat (STR) assay by the ATCC.

Trop-2 Surface Expression on Various Human Breast Carcinoma Cell Lines—

Expression of Trop-2 on the cell surface is based on flow cytometry. Briefly, cells were harvested with Accutase Cell Detachment Solution (Becton Dickinson (BD); Franklin Lakes, N.J.; Cat. No. 561527) and assayed for Trop-2 expression using QuantiBRITE PE beads (BD Cat. No. 340495) and a PE-conjugated anti-Trop-2 antibody (eBiosciences, Cat. No. 12-6024) following the manufacturer's instructions. Data were acquired on a FACSCalibur Flow Cytometer (BD) with CellQuest Pro software, with analysis using Flowjo software (Tree Star; Ashland Oreg.).

In Vitro Cytotoxicity Testing—

Sensitivity to SN-38 was determined using the 3-(4,5-dimethylthiazol-2-yl)-5-(3-carboxymethoxyphenyl)-2-(4-sulfophenyl)-2H-tetrazolium dye reduction assay (MTS dye reduction assay; Promega, Madison, Wis.). Briefly, cells were plated into 96-well clear, flat-bottomed plates as described above. SN-38 dissolved in DMSO was diluted with media to a final concentration of 0.004 to 250 nM. Plates were incubated in humidified chamber for 96 h 37° C./5% $CO_2$, after which the MTS dye was added and placed back into the incubator until untreated control cells had an absorbance greater than 1.0. Growth inhibition was measured as a percent of growth relative to untreated cells. Dose-response curves were generated from the mean of triplicate determinations, and $IC_{50}$-values were calculated using Prism GraphPad Software.

In Vitro Specificity Testing by Flow Cytometry with rH2AX-Stained Cells—

For drug activity testing, HCC1806 and HCC1395 TNBC cell lines cells were seeded in 6-well plates at $5 \times 10^5$ cells/well and held at 37° C. overnight. After cooling the cells for 10 min on ice, the cells were incubated with either IMMU-132 or hA20 anti-CD20-SN38 at ~20 µg/ml (equal SN38/well for both agents) for 30 minutes on ice, washed three times with fresh media, and then returned to 37° C. overnight. Cells were trypsinized briefly, pelleted by centrifugation, fixed in 4% formalin for 15 min, then washed and permeabilized in 0.15% Triton-X100 in PBS for another 15 min After washing twice with 1% bovine serum albumin-PBS, cells were incubated with mouse anti-rH2AX-AF488 (EMD Millipore Corporation, Temecula, Calif.) for 45 minutes at 4° C. The signal intensity of rH2AX was measured by flow cytometry using a BD FACSCalibur (BD Biosciences, San Jose, Calif.).

IHC of Trop-2 in Tumor Microarrays and Patient Specimens—

This involved standard IHC methods on tissue and microarray sections. Scoring was based on the intensity of the stain in ≥10% of the tumor cells within the specimen, including negative, 1+(weak), 2+(moderate), and 3+ (strong).

In Vivo Therapeutic Studies in Xenograft Models—

SN-38 equivalents in a dose of 250 µg ADC to a 20-gram mouse (12.5 mg/kg) is equal to 0.2 mg SN-38/kg. For irinotecan (irinotecan-HCl injection; AREVA Pharmaceuticals, Inc., Elizabethtown, Ky.), 10 mg irinotecan/kg converts to 5.8 mg SN-38/kg based on mass.

Immunoblotting—

Cells ($2 \times 10^6$) were plated in 6-well plates overnight. The following day they were treated with either SN-38 or IMMU-132 at an SN-38 concentration equivalent of 0.4 µg/mL (1 µM) for 24 and 48 h. Parental hRS7 was used as a control for the ADC.

Quantification of SN-38 in Mice with Human Tumor Xenografts—

Two groups, each with 15 animals bearing subcutaneous implants of the human pancreatic carcinoma cell line, were administered either irinotecan or IMMU-132. At 5 different intervals, 3 animals per group were euthanized. The Capan-1 tumors (0.131±0.054 g; N=30) were removed and homogenized in deionized water (DI) (1 part tissue+10 parts DI water); serum was diluted with an equal part DI water. Serum and tissue homogenates were extracted and analyzed by reversed-phase HPLC (RP-HPLC). While extracted samples were adequate for detecting products from the irinotecan-treated animals, samples from animals given IMMU-132 were split into 2 portions, with one undergoing an acid-hydrolysis step in order to release all of the SN-38 bound to the IgG, which would otherwise go undetected in the extracted samples.

Statistics—

Statistical analyses were performed using GraphPad Prism version 5.00 for Windows, GraphPad Software, La Jolla Calif. USA. The specific testing performed is identified with each study.

Results

SN-18 Structure and Properties—

IMMU-132 utilizes the topoisomerase I inhibitor, SN-38, the water soluble metabolite of the anticancer camptothecin, irinotecan (7-ethyl-10-[4-(1-piperidino)-1-piperidino]carbonyloxycamptothecin), that is therapeutically active in colorectal, lung, cervical, and ovarian cancers (Garcia-Carbonero et al., 2002, Clin Cancer Res 8:641061). An important advantage for selecting SN-38 is that the drug's in-vivo pharmacology is well known. Irinotecan must be cleaved by esterases to form SN-38, which is 2-3 orders of magnitude more potent than irinotecan, with activity in the low nanomolar range (Kawato et al., 1991, Cancer Res 51:4187-91). At physiological pH, camptothecins exist in an equilibrium comprising the more active lactone form and the less active (10% potency) open carboxylic acid form (Burke & Mi, 1994, J Med Chem 37:40-46).

The design of the SN-38 derivative used in IMMU-132, CL2A-SN-38, addressed multiple challenges in using this drug in the ADC format, and involved the following features: (i) A short polyethylene glycol (PEG) moiety was placed in the cross-linker to confer aqueous solubility to this highly insoluble drug; (ii) a maleimide group was incorporated for fast thiol-maleimide conjugation to mildly reduced antibody, with a specially-designed synthetic procedure enabling high-yield incorporation of maleimide in the context of assembling the carbonate linkage; (iii) a benzylcarbonate site provided a pH-mediated cleavage site to release the drug from the linker; and (iv) importantly, the crosslinker was attached to SN-38's 20-hydroxy position, which kept the lactone ring of the drug from opening to the less active carboxylic acid form under physiological conditions (Giovanella et al., 2000, Ann NY Acad Sci 922:27-35). The synthesis of SN-38 derivatives and the conjugation of CL2A-SN-38 to mildly reduced hRS7 IgG has been described above. The limited reduction procedure breaks only the interchain disulfide bridges between the heavy-heavy and heavy-light chains, but not the intra-domain disulfides, generating 8 site-specific thiols per antibody molecule. It is then conjugated to CL2A-SN-38, purified by diafiltration, and lyophilized for storage. During manufacturing, conditions are adjusted to minimize any loss of SN-38 from IMMU-132, with the final lyophilized product consistently having <1% free SN-38 when reconstituted. However, when placed in serum and held at 37° C., SN-38 is released from the conjugate with a half-life of ~1 day (not shown).

The release of SN-38 appears to be an important feature of IMMU-132, with this type of linker selected based on efficacy studies that tested SN-38 conjugated to a variety of linkers that had different rates of SN-38 release, from ~10 h release half-life to being highly stable (Moon et al., 2008(30, 31). Optimal therapeutic activity was found with a conjugate having an intermediate release rate in serum of ~2 days. We subsequently improved the manufacturing process for this type of linker, designated CL2A, by removing a phenylalanine residue (Cardillo et al., 2011, Clin Cancer Res 17:3157-64, and then again compared the efficacy with that of another stably-linked anti-Trop-2 conjugate (CL2) that was designed to release SN-38 only under lysosomal conditions (i.e., in the presence of cathepsin B and pH 5.0). In animal models, the anti-Trop-2 conjugate prepared with the CL2A linker yielded better therapeutic responses than when SN-38 was linked stably, indicating that even antibodies that internalized quickly benefitted when SN-38 was allowed to be released in serum with a half-life of ~1 day (Govidan et al. 2013, Mol Cancer Ther 12:968-78). Since clinical studies with radiolabeled antibodies have found the antibodies localize in tumors within a few hours, reaching peak concentrations within 1 day (Sharkey et al., 1995, Cancer Res 55:5935s-45s), selectively enhanced concentrations of SN-38 are delivered locally in the tumor through internalization of the intact conjugate, extracellular release of the free drug, or both mechanisms in concert.

Drug-Antibody Ratio (DAR) Determination.

Five clinical lots of IMMU-132 were evaluated by hydrophobic interaction HPLC (HIC-HPLC), which resolved three peaks representing species with DARs of 6, 7 and 8, with the greatest fraction comprising a DAR=8 (not shown). IMMU-132 was produced consistently by this manufacturing process, with an overall DAR ($DAR_{AVE}$) of 7.60+0.03 among the five clinical lots (not shown). HIC-HPLC results were confirmed by liquid chromatography-mass spectrometry (LC-MS) (not shown). The analysis showed that ≥99% of the 8 available sulfhydryl groups were coupled with the CL2A linker, either with or without SN-38. There were no unsubstituted (or N-ethylmaleimide capped) heavy or light chains detected. Thus, the difference in DAR among the species results from SN-38 liberation from the linker during manufacturing and not from a lower initial substitution ratio. Once prepared and lyophilized, IMMU-132 has been stable for several years.

Effect of DAR on Pharmacokinetics and Anti-Tumor Efficacy in Mice.

Mice bearing Trop-2+ human gastric carcinoma xenografts (NCI-N87) were given 2 treatments 7 days apart, each with equal protein (0.5 mg) doses of IMMU-132 having DARs of 6.89, 3.28, or 1.64 (not shown). Animals treated with the ADCs having a DAR of 6.89 had a significantly improved median survival time (MST) compared to mice given ADCs with either 3.38 or 1.64 DARs (MST=39 days vs. 25 and 21 days, respectively; P<0.0014). There was no difference between groups treated with the 3.28 or 1.64 DAR conjugates and the saline control group.

To further elucidate the importance of a higher DAR, mice bearing NCI-N87 gastric tumors were administered 0.5 mg IMMU-132 with a DAR of 6.89 twice weekly for two weeks (not shown). Another group received twice the protein (1 mg) dose of an IMMU-132 conjugate with a DAR of 3.28. Although both groups received the same total amount of SN-38 (36 μg) with each dosing scheme, those treated with the 6.89 DAR conjugate inhibited tumor growth significantly more than tumor-bearing animals treated with the 3.28 DAR conjugate (P=0.0227; AUC). Additionally, treatment with the lower DAR was not significantly different than the untreated controls. Collectively, these studies indicate that a lower DAR reduces efficacy.

An examination of the pharmacokinetic behavior of conjugates prepared at these different ratios was performed in non-tumor-bearing mice given 0.2 mg of each conjugate, unconjugated hRS7 IgG, or hRS7 IgG that was reduced and then capped with N-ethylmaleimide. Serum was taken at 5 intervals from 0.5 to 168 h and assayed by ELISA for hRS7 IgG. There was no significant difference in the clearance of these conjugates compared to the unconjugated IgG (not shown). Thus, the substitution level did not affect the pharmacokinetics of the conjugates, and equally important, the reduction of the interchain disulfide bonds did not appear to destabilize the antibody.

Trop-2 Expression in TNBC and SN-38 Sensitivity.

Trop-2 expression was determined by immunohistochemistry (IHC) in several tissue microarrays of human tumor specimens. In one microarray containing 31 TNBC specimens, as well as 15 hormone-receptor- or HER-2-positive breast cancers, positive staining occurred in over 95% of the tumors, with 3+ staining indicated in 65% of the cases.

Table 8 lists 6 human breast cancer cell lines, including four TNBC, showing their surface expression of Trop-2 and sensitivity to SN-38. Trop-2 surface expression in 5 of the 6 cell lines exceeded 90,000 copies per cell. SN-38 potency ranged from 2 to 6 nM in 5 of the 6 cell lines, with MCF-7 having the lowest sensitivity of 33 nM. In vitro potency for IMMU-132 is not provided, because nearly all of the SN-38 associated with IMMU-132 is released into the media during the 4-day incubation period, and therefore its potency would be similar to that of SN-38. Therefore, a different strategy was required to illustrate the importance of antibody targeting as a mechanism for delivering SN-38.

TABLE 8

Trop-2 expression and SN-38 sensitivity in breast cancer cell lines.

| Cell Line | Receptor status | Trop-2 surface expression[4] | $IC_{50}$ (nM) SN-38 |
| --- | --- | --- | --- |
| SK-BR-3 | HER2+ | 328,281 ± 47,996 | 2 |
| MDA-MB-468 | TNBC | 301,603 ± 29,470 | 2 |
| HCC38 | TNBC | 181,488 ± 69,351 | 2 |
| MCF-7 | ER+ | 110,646 ± 17,233 | 33 |
| HCC1806 | TNBC | 91,403 ± 20,817 | 1 |
| MDA-MB-231 | TNBC | 32,380 ± 5,460 | 6 |

[4]Mean ± SD number of surface Trop-2 molecules per cell from three separate assays.

Antigen-positive (HCC1806) or -negative (HCC1395) TNBC cell lines that were incubated at 4° C. for 30 min with either IMMU-132 or a non-binding anti-CD20 SN-38 conjugate. The cells were then washed to remove unbound conjugate, and then incubated overnight at 37° C. Cells were fixed and permeabilized, and then stained with the fluorescent anti-phospho-histone H2A.X antibody to detect dsDNA breaks by flow cytometry (Bonner et al., 2008, Nat Rev Cancer 8:957-67) (Table 9). The Trop-2+ breast cancer cell line, HCC1806, when incubated with IMMU-132, had an increase in median fluorescence intensity (MFI) from 168 (untreated baseline) to 546, indicating the increased presence of dsDNA breaks, whereas the MFI for cells incubated with the non-binding conjugate remained at baseline levels. In contrast, MFI for the Trop-2 antigen-negative cell line, HCC1395, remained at baseline levels following treatment with either IMMU-132 or the non-binding control conjugate. Thus, the specificity of IMMU-132 over an irrelevant ADC was conclusively revealed by evidence of dsDNA breaks only in Trop-2-expressing cells incubated with the anti-Trop-2-binding conjugate.

TABLE 9

Specificity of IMMU-132 anti-tumor activity in vitro using flow cytometry with phospho-H2AX (anti-histone)-stained cells.[A]

| Treatment | Median fluorescence intensity | |
| --- | --- | --- |
| | HCC1806 (Trop-2+) | HCC1395 (Trop-2−) |
| Cell alone | 4.25 | 5.54 |
| Cell + anti-rH2AX-AF488 | 168 | 122 |
| Cell + IMMU-132 + anti-rH2AX-AF488 | 546 | 123 |
| Cell + hA20-SN38 + anti-rH2AX-AF488 | 167 | 123 |

[A]HCC1806 (Trop-2+) or HCC1395 (Trop-2−) were incubated at 4° C. with IMMU-132 or a non-binding control conjugate (anti-CD20-SN-38) for 30 min, washed and incubated overnight at 37° C. in fresh drug-free media. Cells were harvested, fixed, and permeabilized, then stained with the fluorescently-conjugated anti-histone antibody (rH2AX-AF488) for detection of double-stranded DNA breaks. The median fluorescence intensity (MFI) is given for (a) background staining of the cells alone (no anti-histone antibody), (b) the background level of dsDNA breaks for the cells that had no prior exposure to the conjugates, and (c) after exposed to IMMU-132 or hA20-SN38 conjugates.

In Vivo Efficacy of Sacituzumab Govitecan in TNBC Xenografts.

The efficacy of IMMU-132 was assessed in nude mice bearing MDA-MB-468 TNBC tumors (not shown). IMMU-132 at a dose of 0.12 or 0.20 mg/kg SN-38-equivalents (0.15 and 0.25 mg IMMU-132/dose) induced significant tumor regression, compared to saline, irinotecan (10 mg/kg; ~5.8 mg/kg SN-38 equivalents by weight), or a control anti-CD20 ADC, hA20-CL2A-SN-38, given at the same 2 dose levels (P<0.0017, area under the curve, AUC). Since mice convert irinotecan to SN-38 more efficiently than humans (38) (in our studies, it averaged ~25%, see below), at this irinotecan dose ~145 to 174 μg of SN-38 would be produced, while the administered dose of IMMU-132 contained only 9.6 μg. Nevertheless, because IMMU-132 selectively targeted SN-38 to the tumors, it was more efficacious. These results corroborate findings in other solid tumor models (Cardillo et al., 2011, Clin Cancer Res 17:3157-69) showing that specific targeting of a small amount of SN-38 to the tumor with IMMU-132 is much more effective than a much larger dose of irinotecan, or for that matter a mixture of hRS7 IgG with an equal amount of free SN-38 (Cardillo et al., 2011, Clin Cancer Res 17:3157-69). The unconjugated RS7 antibody, even at repeated doses of 1 mg per animal, did not show any antitumor effects (Cardillo et al., 2011, Clin Cancer Res 17:3157-69). However, in-vitro studies with gynecological cancers expressing Trop-2 have indicated cell killing with the RS7 mAb by antibody-dependent cellular cytotoxicity (Bignotti et al., 2010, Eur J Cancer 46:944-53; Raji et al., 2011, J Exp Clin Cancer Res 30:106; Varughese et al., 2011, Gynecol Oncol 122:171-7; Varughese et al., 2011, Am J Obstet Gyneol 205:567). Also, a monovalent Fab of another anti-Trop-2 antibody has been reported to be therapeutically active in vitro and in animal studies.

On therapy day 56, four of the seven tumors in mice given 0.12 mg/kg of the hA20-CL2A-SN-38 control ADC already had progressed to the endpoint of 1.0 cm³ (not shown). At this time, these animals were treated with IMMU-132, electing to use the higher dose of 0.2 mg/kg in an attempt to affect the progression of these much larger tumors. Despite the substantial size of the tumors in several animals, all mice demonstrated a therapeutic response, with tumors significantly smaller in size five weeks later (total volume [TV]=0.14±0.14 cm³ vs. 0.74±0.41 cm³, respectively; P=0.0031, two-tailed t-test). Similarly, we chose two animals in the irinotecan-treated group with tumors that progressed to ~0.7 cm³ and re-treated one with irinotecan and the other with IMMU-132 (not shown). Within 2 weeks of ending treatment, the tumor in the irinotecan-treated animal decreased 23% and then began to progress, while the tumor treated with IMMU-132 had stabilized with a 60% decrease in tumor size. These results demonstrate that even in tumors that continued to grow after exposure to SN-38 via a non-specific ADC, a significantly enhanced therapeutic response could be achieved when treated with the Trop-2-specific IMMU-132. However, specific therapeutic effects with IMMU-132 were not achieved in MDA-MB-231 (not shown). This cell line had the lowest Trop-2 levels, but also was the least sensitive to SN-38.

Mechanism of Action of IMMU-132 in TNBC—

The apoptotic pathway utilized by IMMU-132 was examined in the TNBC cell line, MDA-MB-468, and in the HER2+ SK-BR-3 cell line, in order to confirm that the ADC functions on the basis of its incorporated SN-38 (not shown). SN-38 alone and IMMU-132 mediated >2-fold up-regulation of $p21^{WAF1/Cip1}$ within 24 h in MDA-MB-468, and by 48 h, the amount of $p21^{WAF1/Cip1}$ in these cells began to decrease (31% and 43% with SN-38 or IMMU-132, respectively). Interestingly, in the HER2+ SK-BR-3 tumor line, neither SN-38 nor IMMU-132 mediated the up-regulation of $p21^{WAF1/Cip1}$ above constitutive levels in the first 24 h, but as seen in MDA-MB-468 cells after 48-h exposure to SN-38 or IMMU-132, the amount of $p21^{WAF1/Cip1}$ decreased >57%. Both SN-38 and IMMU-132 resulted in cleavage of pro-caspase-3 into its active fragments within 24 h, but with the greater degree of active fragments observed after exposure for 48 h. Of note, in both cell lines, IMMU-132 mediated a greater degree of pro-caspase-3 cleavage, with the highest level observed after 48 h when compared to cells exposed to SN-38. Finally, SN-38 and IMMU-132 both mediated poly ADP ribose polymerase (PARP) cleavage, starting at 24 h, with near complete cleavage after 48 h. Taken together, these results confirm that IMMU-132 has a mechanism of action similar to that of free SN-38 when administered in vitro.

Delivery of SN-38 by IMMU-132 vs. Irinotecan in a Human Tumor Xenograft Model—

Constitutive products derived from irinotecan or IMMU-132 were determined in the serum and tumors of mice implanted s.c. with a human pancreatic cancer xenograft (Capan-1) administered irinotecan (773 μg; SN-38 equivalents=448 μg) and IMMU-132 (1.0 mg; SN-38 equivalents=16 μg).

Irinotecan cleared very rapidly from serum, with conversion to SN-38 and SN-38G seen within 5 min. None of the products was detected at 24 h. The AUCs over a 6-h period were 21.0, 2.5, and 2.8 μg/mL·h for irinotecan, SN-38, and SN-38G, respectively (SN-38 conversion in mice=[2.5+ 2.8]/21=25.2%]). Animals given IMMU-132 had much lower concentrations of free SN-38 in the serum, but it was detected through 48 h (not shown). Free SN-38G was detected only at 1 and 6 h, and was 3- to 7-times lower than free SN-38.

In the Capan-1 tumors excised from irinotecan-treated animals, irinotecan levels were high over 6 h, but undetectable a 24 h ($AUC_{5min-6\ h}$=48.4 µg/g·h). SN-38 was much lower and detected only through 2 h (i.e., $AUC_{5min-2\ h}$=0.4 µg/g·h), with SN-38G values almost 3-fold higher (AUC=1.1 µg/g·h) (not shown). Tumors taken from animals given IMMU-132 did not have any detectable free SN-38 or SN-38G, but instead, all SN-38 in the tumor was bound to IMMU-132. Importantly, since no SN-38G was detected in the tumors, this suggests SN-38 bound to IMMU-132 was not glucuronidated. The AUC for SN-38 bound to IMMU-132 in these tumors was 54.3 µg/g·h, which is 135-fold higher than the amount of SN-38 in the tumors of animals treated with irinotecan over the 2-h period that SN-38 could be detected, even though mice given irinotecan received 28-fold more SN-38 equivalents than administered with IMMU-132 (i.e., 448 vs 16 µg SN-38 equivalents, respectively)

Discussion

We describe a new ADC targeting Trop-2, and early clinical results suggest it is well tolerated and effective in patients with TNBC, as well as other Trop-2$^+$ cancers (Bardia et al., 2014, San Antonio Breast Cancer Symposium, P5-19-27). Due to its distinct properties, IMMU-132 represents a second-generation ADC. Typically, ADCs require 4 broad attributes to be optimally-effective: (i) selective targeting/activity; (ii) binding, affinity, internalization, and immunogenicity of the antibody used in the ADC; (iii) the drug, its potency, metabolism and pharmacological disposition, and (iv) how the drug is bound to the antibody. Target selectivity is the most common requirement for all ADCs, since this will play a major role in defining the therapeutic index (ratio of toxicity to tumor vs. normal cells). Trop-2 appears to have both a high prevalence on a number of epithelial cancers, but it is also expressed by several normal tissues (Cubas et al., 2009, Biochim Biophys Acta 1796: 309-14; Trerotola et al., 2013, Oncogene 32:222-33; Stepan et al., 2011, 59:701-10), which could have impacted specificity. However, expression in normal tissues appears to be lower than in cancers (Bignotti et al., 2010, Eur J Cancer 46:944-53), and Trop-2 appears to be shielded by normal tissue architecture that limits accessibility to an antibody, whereas in cancer, these tissue barriers are compromised by the invading tumor. Evidence of this was apparent from initial toxicological studies in monkeys, where despite escalating IMMU-132 doses to levels leading to irinotecan-like neutropenia and diarrhea, histopathological damage to Trop-2-expressing normal tissues did not occur (Cardillo et al., 2011, Clin Cancer Res 17:3157-69). These results appear to have been confirmed clinically, where no specific organ toxicity has been noted in patients to-date, except for the known toxicities of the parental compound, irinotecan (Bardia et al., 2014, San Antonio Breast Cancer Symposium, P5-19-27), which are more manageable with IMMU-132.

A generally accepted and important criterion for ADC therapy is that the antibody should internalize, delivering its chemotherapeutic inside the cell, where it is usually metabolized in lysosomes. Despite IMMU-132's internalization, we believe that the linker in this ADC, which affords local release of SN-38 that likely can induce a bystander effect on the cancer cells, is another feature that sets this platform apart from those using an ultratoxic drug. Indeed, having an ultratoxic agent linked stably to the IgG is the only configuration that would preserve a useful therapeutic window for those types of compounds. However, using a more moderately-toxic drug does not give the latitude to use a linker that would release the drug too early once in the circulation. Our group explored linkers that released SN-38 from the conjugate with different half-lives in serum, ranging from ~10 h to a highly stable linker, but it was the linker with the intermediate stability that provided the best therapeutic response in mouse-human tumor xenograft models (Moon et al., 2008, J Med Chem 51:6916-26; Govindan et al., 2009, Clin Chem Res 15:6052-61). Since this initial work, we showed that a highly stable linkage of SN-38 was significantly less effective than the CL2A linker that has a more intermediate stability in serum (Govindan et al., 2013, Mol Cancer Ther 12:968-78).

Another current tenet of ADC design is to use an ultracytotoxic drug to compensate for low levels of antibody accretion in tumors, typically 0.003 to 0.08% of the injected dose per gram (Sharkey et al., 1995, Cancer Res 55:5935s-45s). The current generation of ultratoxic-drug conjugates have found a drug:antibody substitutions of ≤4:1 to be optimal, since higher ratios adversely affected their pharmacokinetics and diminished the therapeutic index by collateral toxicities (Hamblett et al., 2004, Clin Cancer Res 10:7063-70). In this second-generation ADC platform, we elected to use an IgG-coupling method that site-specifically links the drug to the interchain disulfides through mild reduction of the IgG, which exposes 8 binding sites. With the CL2A-SN-38 linker, we achieved a DAR of 7.6:1, with LC-MS data showing each of the 8 coupling sites bears the CL2A linker, but apparently some SN-38 is lost during the manufacturing procedure. Nevertheless, 95% of the CL2A linker has 7-8 SN-38 molecules. We found subsequently that (a) coupling to these sites does not destabilize the antibody, and (b) conjugates prepared with these sites substituted at higher levels did not compromise antibody binding, nor did it affect pharmacokinetic properties. Indeed, we demonstrated that conjugates prepared at the maximum substitution level had the best therapeutic response in mouse-human tumor xenograft models.

One of the more notable features of IMMU-132 from a tolerability perspective is that the SN-38 bound to IgG is not glucuronidated, which is a critical step in the detoxification of irinotecan. With irinotecan therapy, most of the SN-38 generated is readily converted in the liver to the inactive SN-38G form. Estimates of the AUC for SN-38G show it is often 4.5- to 32-times higher than SN-38 (Gupta et al., 1994, Cancer Res 54:3723-25; Xie et al., 2002, J Clin Oncol 20:3293-301). SN-38G's secretion into the bile and subsequent deconjugation by beta-glucuronidase produced by the intestinal flora is strongly implicated in the enterohepatic recirculation of SN-38 and the delayed severe diarrhea observed with irinotecan (Stein et al., 2010, Ther Adv Med Oncol 2:51-63). After IMMU-132 administration, concentrations of SN-38G were very low in our animal and clinical studies (e.g., in the serum of patients given IMU-132, only 20-40% of the free SN-38 levels are in the form of SN-38G), providing strong evidence that SN-38 bound to IgG is largely protected from glucuronidation, even though the 10-hydroxy position of the SN-38 is available. We speculate that low levels of SN-38G generated by IMMU-132 contributes to the lower incidence and intensity of diarrhea in patients receiving this ADC compared to irinotecan therapy.

Preventing glucuronidation of the SN-38 bound to the antibody may also contribute to improved therapeutic effects for SN-38 delivered to the tumor. Extracts of tumors from animals given irinotecan found high levels of irinotecan, with 10-fold lower concentrations of SN-38 and SN-38G. In contrast, the only SN-38 found in the tumors of animals given IMMU-132 was SN-38 bound to the IgG. We hypothesize that the conjugate retained in the tumor will eventually be internalized, thereby releasing its SN-38 payload, or SN-38 could be release outside the tumor cell; however, it would be released in its fully active form, with a lower likelihood of being converted to SN-38G, which occurs primarily in the liver. It is also important to emphasize that by coupling the linker to the 20-hydroxy position of SN-38, the SN-38 is maintained in the active lactone form (Zhao et al., 2000, J Org Chem 65:4601-6). Collectively, these results suggest that IMMU-132 is able to deliver and concentrate SN-38 to Trop-2+ tumors in a selective manner compared to SN-38 derived from non-targeted irinotecan, with the SN-38 delivered by IMMU-132 likely being released in the tumor in the fully active, non-glucuronidated, lactone form.

Irinotecan is not conventionally used to treat breast cancer patients. However, the experiments shown here with TNBC cell lines indicate that concentrating higher amounts of SN-38 into the tumor enhances its activity. In both the MDA-MB-468 TNBC and HER2+ SK-BR-3 tumor lines, IMMU-132 mediated the activation of the intrinsic apoptotic pathway, with cleavage of pro-caspases into their active fragments and PARP cleavage. The demonstration of double-stranded DNA breaks of cancer cells treated with IMMU-132 (Bardia et al., 2014, San Antonio Breast Cancer Symposium, P5-19-27) compared to an irrelevant SN-38 ADC) confirms the selective delivery of SN-38 into the target cells. Most importantly, these laboratory findings are confirmed by therapy of patients with heavily-pretreated, metastatic TNBC, where durable objective responses have been observed (Bardia et al., 2014, San Antonio Breast Cancer Symposium, P5-19-27). It also appears that IMMU-132 is active in patients with other cancers and who have failed a prior therapy regimen containing a topoisomerase I inhibitor (Starodub et al., 2015, Clin Cancer Res 21:3870-78).

In conclusion, the use of SN-38 conjugated at a very high ratio of drug to antibody, using a moderately-stable linker, is efficacious in animal models and also clinically, constituting a second-generation ADC platform. Our findings indicate that Trop-2 is a clinically-relevant and novel target in Trop-2+ solid tumors, particularly TNBC.

Example 17. Studies on the Mechanism of Action of IMMU-132

Sacituzumab govitecan (IMMU-132, also known as hRS7-CL2A-SN-38) is an antibody-drug conjugate (ADC) targeting Trop-2, a surface glycoprotein expressed on many epithelial tumors, for delivery of SN-38, the active metabolite of irinotecan. Unlike most ADCs that use ultratoxic drugs and stable linkers, IMMU-132 uses a moderately toxic drug with a moderately stable carbonate bond between SN-38 and the linker. Flow cytometry and immunohistochemistry disclosed Trop-2 is expressed in a wide range of tumor types, including gastric, pancreatic, triple-negative breast (TNBC), colonic, prostate, and lung. While cell-binding experiments reveal no significant differences between IMMU-132 and parental hRS7 antibody, surface plasmon resonance analysis using a Trop-2 CM5 chip shows a significant binding advantage for IMMU-132 over hRS7. The conjugate retained binding to the neonatal receptor, but lost greater than 60% of the antibody-dependent cell-mediated cytotoxicity activity compared to hRS7.

Exposure of tumor cells to either free SN-38 or IMMU-132 demonstrated the same signaling pathways, with pJNK1/2 and p21WAF1/Cip1 up-regulation followed by cleavage of caspases 9, 7, and 3, ultimately leading to poly-ADP-ribose polymerase cleavage and double-stranded DNA breaks.

Pharmacokinetics of the intact ADC in mice reveals a mean residence time (MRT) of 15.4 h, while the carrier hRS7 antibody cleared at a similar rate as unconjugated antibody (MRT=~300 h). IMMU-132 treatment of mice bearing human gastric cancer xenografts (17.5 mg/kg; twice weekly×4 weeks) resulted in significant anti-tumor effects compared to mice treated with a non-specific control. Clinically relevant dosing schemes of IMMU-132 administered either every other week, weekly, or twice weekly in mice bearing human pancreatic or gastric cancer xenografts demonstrate similar, significant anti-tumor effects in both models. Current Phase I/II clinical trials (ClinicalTrials.gov, NCT01631552) confirm anticancer activity of IMMU-132 in cancers expressing Trop-2, including gastric and pancreatic cancer patients.

Introduction

There will be an estimated 22,220 new cases of gastric cancer diagnosed in the United States this year, with a further 10,990 deaths attributed to this disease (Siegel et al., 2014, CA Cancer J Clin 64:9-29). While 5-year survival rates are trending upward (currently at 29%), they are still quite low when compared to most others, including cancers of the colon, breast, and prostate (65%, 90%, and 100%, respectively). In fact, among human cancers, only esophageal, liver, lung, and pancreatic have worse 5-year survival rates. Pancreatic cancer remains the fourth leading cause of all cancer deaths in the U.S., with a 5-year survival rate of only 6% (Siegel et al., 2014, CA Cancer J Clin 64:9-29). It is clear from such grim statistics for gastric and pancreatic cancer that new therapeutic approaches are needed.

Trop-2 is a 45-kDa glycoprotein that belongs to the TACSTD gene family, specifically TACSTD22. Overexpression of this trans-membrane protein on many different epithelial cancers has been linked to an overall poor prognosis. Trop-2 is essential for anchorage-independent cell growth and tumorigenesis (Wang et al., 2008, Mol Cancer Ther 7:280-85; Trerotola et al., 2013, Oncogene 32:222-33). It functions as a calcium signal transducer that requires an intact cytoplasmic tail that is phosphorylated by protein kinase C12-14. Pro-growth signaling associated with Trop-2 includes NF-κB, cyclin D1 and ERK (Guerra et al., 2013, Oncogene 32:1594-1600; Cubas et al., 2010, Mol Cancer 9:253).

In pancreatic cancer, Trop-2 overexpression was observed in 55% of patients studied, with a positive correlation with metastasis, tumor grade, and poor progression-free survival of patients who underwent surgery with curative intent (Fong et al., 2008, Br J Cancer 99:1290-95). Likewise, in gastric cancer 56% of patients exhibited Trop-2 overexpression on their tumors, which again correlated with shorter disease-free survival and a poorer prognosis in those patients with lymph node involvement of Trop-2-positive tumor cells (Muhlmann et al., 2009, J Clin Pathol 63:152-58). Given these characteristics and the fact that Trop-2 is linked to so many intractable cancers, Trop-2 is an attractive target for therapeutic intervention with an antibody-drug conjugate (ADC).

A general paradigm for using an antibody to target a drug to a tumor includes several key features, among them: (a) an antigen target that is preferentially expressed on the tumor versus normal tissue, (b) an antibody that has good affinity and is internalized by the tumor cell, and (c) an ultra-toxic drug that is coupled stably to the antibody (Panowski et al., 2014, mAbs 6:34-45). Along these lines, we developed an antibody, designated RS7-3G11 (RS7), that bound to Trop-2 in a number of solid tumors (Stein et al., 1993, Int J Cancer 55:938-46; Basu et al., 1995, Int J Cancer 62:472-79) with nanomolar affinity (Cardillo et al., 2011k, Clin Cancer Res 17:3157-69), and once bound to Trop-2, is internalized by the cell (Shih et al., 1995, Cancer Res 55:5857s-63s).

By immunohistochemistry, Trop-2 is expressed in some normal tissues, though usually at much lower intensities when compared to neoplastic tissue, and often is present in regions of the tissues with restricted vascular access (Trerotola et al., 2013, Oncogene 32:222-33). Based on these characteristics, RS7 was humanized and conjugated with the active metabolite of irinotecan, 7-ethyl-10-hydroxycamptothecin (SN-38). In vitro cytotoxicity in numerous cell lines has found $IC_{50}$-values in the single digit nanomolar range for SN-38, compared to picomolar range for many of the ultra-toxic drugs currently used in ADCs (Cardillo et al., 2011, Clin Cancer Res 17:3157-69). While the prevailing opinion is to use ultra-toxic agents, such as auristatins or maytansines, to make ADCs with only 2-4 drugs per antibody linked stably to the antibody, such agents have a narrow therapeutic window, resulting in renewed efforts to re-engineer ADCs to broaden their therapeutic index (Junutula et al., 2010, Clin Cancer Res 16:4769-78).

As one approach to diverge from this practice, we conjugated 7-8 SN-38 molecules per antibody using a linker that releases SN-38 with half-life of ~1 day in human serum. It is hypothesized that using a less stable linker allows for SN-38 release at the tumor site after the ADC targets the cells, making the drug accessible to surrounding tumor cells and not just cells directly targeted by the ADC. The resulting ADC, hRS7-CL2A-SN-38 (sacituzumab govitecan, or IMMU-132), has shown anti-tumor activity against a wide range of tumor types (Cardillo et al., 2011, Clin Cancer Res 17:3157-69). More recently, IMMU-132 has demonstrated significant anti-tumor activity against a pre-clinical model of triple negative breast cancer (TNBC) (Goldenberg et al., 2014, Poster presented at San Antonia Breast Cancer Symposium, December 9-13, Abstr. P5-19-08). Most importantly, in a current Phase I/II clinical trial, IMMU-132 has shown activity in TNBC patients (Bardia et al., 2014, Poster presented at San Antonia Breast Cancer Symposium, December 9-13, Abstr. P5-19-2), thus validating this paradigm shift in ADC chemistry using a less toxic drug and a linker that releases SN-38 over time rather than being totally dependent on internalization of the ADC to achieve activity.

SN-38 is a known topoisomerase-I inhibitor that induces significant damage to a cell's DNA. It mediates the upregulation of early pro-apoptotic proteins, p53 and p21WAF1/Cip1, resulting in caspase activation and poly-ADP-ribose polymerase (PARP) cleavage. Expression of p21WAF1/Cip1 is associated with G1 arrest of the cell cycle and is thus a hallmark of the intrinsic apoptotic pathway. We demonstrated previously that IMMU-132 likewise could mediate the up-regulation of early pro-apoptosis signaling events (p53 and p21WAF1/Cip1) resulting in PARP cleavage in NSCLC (Calu-3) and pancreatic (BxPC-3) cell lines consistent with the intrinsic pro-apoptosis signaling pathway (Cardillo et al., 2011, Clin Cancer Res 17:3157-69).

Herein, we further characterize IMMU-132, with particular attention towards the treatment of solid cancers, especially human gastric and pancreatic tumors. Trop-2 surface expression across a range of solid tumor types is examined and correlated with in vivo expression in tumor xenografts. Mechanistic studies further elucidate the intrinsic pro-apoptotic signaling events mediated by IMMU-132, including evidence of increased double stranded DNA (dsDNA) breaks and later caspase activation. Finally, clinically-relevant and non-toxic dosing schemes are compared in gastric and pancreatic carcinoma disease models, testing twice-weekly, weekly, and every other week schedules to ascertain which treatment cycle may be best applied to a clinical setting without loss of efficacy.

Experimental Procedures

Cell Lines and Chemotherapeutics—

All human cancer cell lines used were purchased from the American Type Culture Collection (ATCC) (Manassas, Va.). Each was maintained according to the recommendations of ATCC and routinely tested for mycoplasma, and all were authenticated by short tandem repeat (STR) assay by the ATCC. IMMU-132 (hRS7-SN-38) and control ADCs (anti-CD20 hA20-SN-38 and anti-CD22 hLL2-SN-38) were made as previously described and stored at −20° C. (Cardillo et al., 2011, Clin Cancer Res 17:3157-69). SN-38 was purchased (Biddle Sawyer Pharma, LLC, New York, N.Y.) and stored in 1 mM aliquots in DMSO at −20° C.

Trop-2 ELISA—

Recombinant human Trop-2 with a His-tag (Sino Biological, Inc., Bejing, China; Cat#10428-H09H) and recombinant mouse Trop-2 with a His-Tag (Sino Biological, Inc., Cat#50922-M08H) were plated onto Ni-NTA Hissorb strips (Qiagen GmbH Cat#35023) at 1 µg for 1 h at room temperature. The plate was washed four times with PBS-Tween (0.05%) wash buffer. Serial dilutions of hRS7 were made in 1% BSA-PBS dilution buffer to a test range of 0.1 ng/mL to 10 µg/mL. The plates were then incubated for 2 h at room temperature before being washed four times followed by the addition of a peroxidase conjugated secondary antibody (goat anti-human, Fc fragment specific; Jackson Immunoresearch Cat#109-036-098). After a 45-min incubation, the plate was washed and a substrate solution (o-phenylenediamine dihydrochloride (OPD); Sigma, Cat#P828) added to all the wells. Plates were incubated in the dark for 15 min before the reaction was stopped with 4N sulfuric acid. The plates were read at 450 nm on Biotek ELX808 plate reader. Data were analyzed and graphed using Prism GraphPad Software (v4.03) (Advanced Graphics Software, Inc.; Encinitas, Calif.).

In Vitro Cell Binding—

LumiGLO Chemiluminescent Substrate System (KPL, Gaithersberg, Md.) was used to detect antibody binding to cells. Briefly, cells were plated into a 96 black-well, flat-clear-bottom plate overnight. Antibodies were serially diluted 1:2 and added in triplicate, yielding a concentration range from 0.03 to 66.7 nM. After incubating for 1 h at 4° C., the media was removed and the cells washed with fresh cold media followed by the addition of a 1:20,000 dilution of goat-antihuman horseradish peroxidase-conjugated secondary antibody (Jackson Immunoresearch, West Grove, Pa.) for 1 h at 4° C. The plates were again washed before the addition of the LumiGLO reagent. Plates were read for luminescence using an Envision plate reader (Perkin Elmer, Boston Mass.). Data were analyzed by non-linear regression to determine the equilibrium dissociation constant (KD). Statistical comparisons of KD-values were made with Prism GraphPad Software (v4.03) (Advanced Graphics Software, Inc.; Encinitas, Calif.) using an F-Test on the best-fit curves for the data. Significance was set at P<0.05.

Antibody-Dependent Cell-Mediated Cytotoxicity (ADCC)—

A four-hour LDH-release assay was performed to evaluate ADCC activity elicited by IMMU-132, hRS7 IgG, hLL2-SN-38 and hLL2 IgG (hLL2 are non-binding anti-CD22 conjugates for the solid tumor cell lines). Briefly, target cells (MDA-MB-468, NIH:OVCAR-3, or BxPC-3) were plated at 1×10$^4$ cells/well in a 96-well, black, flat-bottom plate and incubated overnight. The next day, peripheral blood mononuclear effector cells (PBMCs) were freshly isolated from a donor and added to assigned wells on the reaction plate at an E:T ratio of 50:1. Acquisition of human PBMCs was done under the approval of the New England Institutional Review Board (Newton, Mass.). Test reagents were added to their assigned wells at a final concentration of 33.3 nM. One set of wells received ADCC assay medium alone for background control and another set of wells received cells alone plus TritonX100 for maximum cells lysis control. The plate was incubated for 4 h at 37° C. After 4 h, target cell lysis was assessed by a homogenous fluorometric LDH release assay (Cyto Tox-One Homogenous Membrane Integrity Assay; Promega, Cat. G7891).

The plates were read (544 nm-590 nm) using an Envision plate reader (PerkinElmer LAS, Inc.; Shelton, Conn.). Data were analyzed by Microsoft Excel. Percent specific lysis was calculated as follows:

$$\% \text{ Specific Lysis} = \frac{\text{Experimental} - (\text{Effector} + \text{Target Control})}{\text{Max. Lysis} - (\text{Target Control})} \times 100$$

where:
Experimental: effector+target cells+antibody
Effector+Target Control: effector+target cells
Max. Lysis: target cells+Triton-X100
Target Control: target cells only Surface Plasmon Resonance Binding (BIACORE)—

Briefly, rhTrop-2/TACSTD2 (Sino Biological, Inc.) or recombinant human neonatal receptor (FcRn), produced as described (Wang et al., 2011, Drug Metab Dispos 39:1469-77), was immobilized with an amine coupling kit (GE Healthcare; Cat. No. BR-1000-50) on a CM5 sensor chip (GE Healthcare; Cat. #BR-1000-12) following manufacturer's instructions for a low-density chip. Three separate sets of dilutions of hRS7 IgG and IMMU-132 were made in running buffer (400 nM, 200 nM, 100 nM, 50 nM and 25 nM). Each set would make up a separate run on the BIACORE (BIACORE-X; Biacore Inc., Piscataway, N.J.) and data were analyzed using BIAevaluation Software (Biacore Inc., v4.1). Analysis was performed with a 1:1 (Langmuir) Binding Model and Fit, using all five concentration points for each sample run to determine the best fit (lowest $\chi^2$ value). The KDvalue was calculated using the formula KD=kd1/ka1, where kd1 is the dissociation rate-constant and ka1 is the association-rate constant.

Immunohistological Assessment of the Distribution of Trop-2 in Formalin-Fixed, Paraffin-Embedded Tissues—

Tumor xenografts were taken from mice, fixed in 10% buffered formalin and paraffin-embedded. After de-paraffination, 5 μm sections were incubated with Tris/EDTA buffer (DaKo Target Retrieval Solution, pH 9.0; Dako, Denmark), at 95° C. for 30 min in a NxGen Decloaking Chamber (Biocare Medical, Concord, Calif.). Trop-2 was detected with a goat polyclonal antihuman Trop-2 antibody at 10 μg/mL (R&D Systems, Minneapolis, Minn.) and stained with Vector VECTASTAINR ABC Kit (Vector Laboratories, Inc., Burlingame, Calif.). Normal goat antibody was used as the negative control (R&D Systems, Minneapolis, Minn.). Tissues were counterstained with hematoxylin for 6 seconds.

Trop-2 Surface Expression on Human Carcinoma Cell Lines—

Expression of Trop-2 on the cell surface is based on flow cytometry. Briefly, cells were harvested with Accutase Cell Detachment Solution (Becton Dickinson (BD), Franklin Lakes, N.J.; Cat. No. 561527) and assayed for Trop-2 expression using QuantiBRITE PE beads (BD Cat. No. 340495) and a PE-conjugated anti-Trop-2 antibody (eBiosciences, Cat. No. 12-6024) following the manufactures' instructions. Data were acquired on a FACSCalibur Flow Cytometer (BD) with CellQuest Pro software. Staining was analyzed with Flowjo software (Tree Star, Ashland Oreg.).

Pharmacokinetics—

Naive female NCr nude (nu/nu) mice, 8-10 weeks old, were purchased from Taconic Farms (Germantown, N.Y.). Mice (N-5) were injected i.v. with 200 μg of IMMU-132, parental hRS7, or modified hRS7-NEM (hRS7 treated with TCEP and conjugated with N-ethylmaleimide). Animals were bled via retroorbital plexis at 30-min, 4-, 24-, 72- and 168-h post-injection. ELISA was utilized to determine serum concentrations of total hRS7 IgG by competing for the binding to an anti-hRS7 IgG idiotype antibody with a horseradish peroxidase conjugate of hRS7. Serum concentrations of intact IMMU-132 were determined using an anti-SN-38 antibody to capture and a horseradish peroxidase-conjugated anti-hRS7 IgG antibody to detect. Pharmacokinetic (PK) parameters were computed by noncompartmental analysis using Phoenix WinNonlin software (version 6.3; Pharsight Corp., Mountainview, Calif.).

Assessment of Double-Stranded DNA Breaks In Vitro—

For drug activity testing, BxPC-3 cells were seeded in 6-well plates at 5×105 cells/well and held at 37° C. overnight. After 10 min cooling on ice, cells were incubated with IMMU-132, hA20-SN-38, or hRS7-IgG at the final concentration of 20 μg/ml for 30 min on ice, washed three times with fresh media, and then returned to 37° C. to continue culture overnight. The following morning, cells were trypsinized briefly, spun down, stained with Fixable Viability Stain 450 (BD Biosciences, San Jose, Calif.), washed with 1% BSA-PBS, and then fixed in 4% formalin for 15 min, washed again and permeabilized in 0.15% Triton-X100 in PBS for another 15 min. After washing twice with 1% BSA-PBS, cells were incubated with mouse anti-γH2AX-AF488 (EMD Millipore Corporation, Temecula, Calif.) for 45 min at 4° C. The signal intensity of γH2AX was measured by flow cytometry using a BD FACSCanto (BD Biosciences, San Jose, Calif.).

In Vivo Therapeutic Studies—

NCr female athymic nude (nu/nu) mice, 4-8 weeks old, were purchased from Taconic Farms (Germantown, N.Y.). NCI-N87 gastric tumor xenografts were established by harvesting cells from tissue culture and making a final cell suspension 1:1 in matrigel (BD Bioscience; San Jose, Calif.), with each mouse receiving a total of 1×10$^7$ cells s.c. in the right flank. For BxPC-3. xenografts of 1 g were harvested, and a tumor suspension made in HBSS to a concentration of 40% tumor w/v. This suspension was mixed 1:1 with matrigel for a final tumor suspension of 20% w/v. Mice were then injected with 300 μL s.c. Tumor volume (TV) was determined by measurements in two dimensions using calipers, with volumes defined as: L×w$^2$/2, where L is the longest dimension of the tumor and w the shortest. For IHC, tumors were allowed to grow to approximately 0.5 cm$^3$ before the mice were euthanized and the tumors removed, formalin-fixed and paraffin-embedded. For therapy studies, mice were randomized into treatment groups and therapy begun when tumor volumes were approximately 0.25 cm$^3$.

Treatment regimens, dosages, and number of animals in each experiment are described in the Results and in the Figure legends. The lyophilized IMMU-132 and control ADC (hA20-SN-38) were reconstituted and diluted as required in sterile saline.

Mice were euthanized and deemed to have succumbed to disease once tumors grew to greater than 1.0 cm³ in size. Best responses to therapy were defined as: partial response, shrinking >30% from starting size; stable disease, tumor volumes shrinking up to 29% or increase no greater than 20% of initial size; progression, tumors increase ≥20% either from their starting size or from their nadir. Time to progression (TTP) was determined as time post-therapy initiation when the tumor grew more than 20% in size from its nadir.

Statistical analysis of tumor growth was based on area under the curve (AUC). Profiles of individual tumor growth were obtained through linear-curve modeling. An f-test was employed to determine equality of variance between groups prior to statistical analysis of growth curves. A two-tailed t-test was used to assess statistical significance between the various treatment groups and controls, except for the saline control, where a one-tailed t-test was used (significance at P≤0.05). Survival studies were analyzed using Kaplan-Meier plots (log-rank analysis), using the Prism GraphPad Software (v4.03) software package (Advanced Graphics Software, Inc., Encinitas, Calif.).

Immunoblotting—

Cells (2×10⁶) were plated in 6-well plates overnight. The following day they were treated with either free SN-38 (dissolved in DMSO) or IMMU-132 at an SN-38 concentration equivalent to 0.4 µg/mL (1 µM). Parental hRS7 was used as a control for the ADC. Cells were lysed in buffer containing 10 mM Tris, pH 7.4, 150 mM NaCl, protease inhibitors and phosphatase inhibitors (2 mM Na2PO4, 10 mM NaF). A total of 20 µg protein was resolved in a 4-20% SDS polyacrylamide gel, transferred onto a nitrocellulose membrane and blocked by 5% non-fat milk in 1×TBS-T (Tris-buffered saline, 0.1% Tween-20) for 1 h at room temperature. Membranes were probed overnight at 4° C. with primary antibodies followed by 1-h incubation with antirabbit secondary antibody (1:2500) at room temperature. Signal detection was done using a chemiluminescence kit (Supersignal West Dura, Thermo Scientific; Rockford, Ill.) with the membranes visualized on a Kodak Image Station 40000R. Primary antibodies p21Waf1/Cip1 (Cat. No. 2947), Caspase-3 (Cat. No. 9665), Caspase-7 (Cat. No. 9492), Caspase-9 (Cat. No. 9502), PARP (Cat. No. 9542), β-actin (Cat. No. 4967), pJNK1/2 (Cat. No. 4668), JNK (Cat. No. 9258), and goat anti-rabbit-HRP secondary antibody (Cat. No. 7074) were obtained from Cell Signal Technology (Danvers, Mass.).

Results

Trop-2 Expression Levels in Multiple Solid Tumor Cell Lines—

Surface expression of Trop-2 is evident in a variety of human solid tumor lines, including gastric, pancreatic, breast, colon, and lung (Table 10). There is no one tumor type that had higher expression above any other, with variability observed within a given tumor cell type. For example, within gastric adenocarcinomas, Trop-2 levels ranged from very low 494±19 (Hs 746T) to high 246,857±64,651 (NCI-N87) surface molecules per cell.

Gastrointestinal tumor xenografts stained for Trop-2 expression showed both cytoplasmic and membrane staining (not shown). Staining intensity correlated well with the results for surface Trop-2 expression determined by FACS analysis. For the pancreatic adenocarcinomas, all three had homogenous staining, with BxPC-3 representing 2+ to 3+ staining. NCI-N87 gastric adenocarcinoma had a more heterogeneous staining pattern, with 3+ staining of the apical lining of the glands and less pronounced staining of surrounding tumor cells. COLO 205 demonstrated only very focal 1+ to 2+ staining, whereas HT-29 showed very rare 1+ staining of a few cells.

TABLE 10

Trop-2 surface expression levels in various solid tumor lines via FACS analysis. a

| Cell Line | Number of Surface Trop-2 Molecules per Cell Mean ± SD |
|---|---|
| Gastric | |
| NCI-N87 | 246,857 ± 64,651 |
| AGS | 53,756 ± 23,527 |
| Hs 746T | 494 ± 19 |
| Pancreatic | |
| BxPC-3 | 493,773 ± 97,779 |
| CFPAC-1 | 162,871 ± 28,161 |
| Capan-1 | 157,376 ± 36,976 |
| HPAF-II | 115,533 ± 28,627 |
| Breast (TN) | |
| MDA-MB-468 | 301,603 ± 29,470 |
| HCC38 | 181,488 ± 69,351 |
| HCC1806 | 91,403 ± 20,817 |
| MDA-MB-231 | 32,380 ± 5,460 |
| Breast | |
| SK-BR-3 (HER2+) | 328,281 ± 47,996 |
| MCF-7 (ER2+) | 110,646 ± 17,233 |
| Colon | |
| COLO 205 | 58,179 ± 6,909 |
| HT-29 | 68 ± 17 |
| NSCLC | |
| Calu-3 | 128,201 ± 50,708 |
| Sq. Cell Lung | |
| SK-MES-1 | 29,488 ± 5,824 |
| Acute T-Cell Leukemia | |
| Jurkat | 0 | a Three separate assays were performed, with the mean and standard deviation provided.

IMMU-132 Binding Characteristics—

To further demonstrate that hRS7 does not cross-react with murine Trop-2, an ELISA was performed on plates coated with either recombinant murine Trop-2 or human Trop-2 (not shown). Humanized RS7 specifically bound only to the human Trop-2 (KD=0.3 nM); there was no cross-reactivity with the murine Trop-2. Control polyclonal rabbit anti-murine Trop-2 and antihuman Trop-2 antibodies did cross-react and bound to both forms of Trop-2 (data not shown).

IMMU-132 binding to multiple cell lines was examined, with comparison to parental hRS7 as well as to modified hRS7, hRS7-NEM (hRS7 treated with TCEP and conjugated with N-ethylmaleimide) (not shown). In all cases, calculated KD-values were in the sub-nanomolar range, with no significant differences between hRS7, IMMU-132, and hRS7-NEM within a given cell line.

Comparisons in binding of IMMU-132 and hRS7 were further investigated using surface plasmon resonance (BIA-CORE) analysis (not sown). A low-density Trop-2 biosensor chip (density=1110 RU) was utilized with recombinant human Trop-2. Not only did three independent binding runs demonstrate that IMMU-132 is not affected adversely by the SN-38-conjugation process, but it demonstrated a higher binding affinity to Trop-2 than hRS7 (0.26±0.14 nM vs. 0.51±0.04 nM, respectively; P=0.0398).

Mechanism of Action: ADCC and Intrinsic Apoptosis Signaling Pathways—

ADCC activity of IMMU-132 was compared to hRS7 in three different cell lines, TNBC (MDAMB-468), ovarian (NIH:OVCAR-3), and pancreatic (BxPC-3) (not shown). In all three, hRS7 significantly mediated cell lysis compared to all other treatments, including IMMU-132 (P<0.0054). ADCC decreased by more than 60% when IMMU-132 was used to target the cells as compared to hRS7. For example, in MDA-MB-468, specific lysis mediated by hRS7 was 29.8±2.6% versus 8.6±2.6% for IMMU-132 (not shown; P<0.0001). Similar loss in ADCC activity was likewise observed in NIH:OVCAR-3 and BxPC-3 (not shown; P<0.0001 and P<0.0054; respectively). This diminished ADCC activity appears to be the result of changes to the antibody during the conjugation process, since this same loss in specific cell lysis was evident with hRS7-NEM, which lacks the CL2A-SN-38 linker, having the cysteines blocked instead with N-ethylmaleimide (not shown). There is no CDC activity associated with hRS7 or IMMU-132 (data not shown).

IMMU-132 has been shown previously to mediate the up-regulation of early pro-apoptosis signaling events (p53 and p21WAF1/Cip1), ultimately leading to the cleavage of PARP20. In order to better define the apoptotic pathway utilized by IMMU-132, the NCI-N87 human gastric carcinoma and BxPC-3 pancreatic adenocarcinoma cell lines were exposed to 1 µM of free SN-38 or the equivalent amount of IMMU-132 (not shown). Both free SN-38 and IMMU-132 mediate the up-regulation of p21WAF1/Cip1, though it is not until 48 h that the up-regulation between the NCI-N87 cells exposed to free SN-38 versus IMMU-132 are the same (not shown), whereas in BxPC-3 maximum up-regulation is evident within 24 h (not shown). Both free SN-38 and IMMU-132 demonstrate cleavage of pro-caspase-9 and -7 within 48 h of exposure. Procaspase-3 is cleaved in both cell lines with the highest degree of cleavage observed after 48 h. Finally, both free SN-38 and IMMU-132 mediated PARP cleavage. This first becomes evident at 24 h, with increased cleavage at 48 h. Taken together, these data confirm that the SN-38 contained in IMMU-132 has the same activity as free SN-38.

In addition to these later apoptosis signaling events, an earlier event associated with this pathway, namely the phosphorylation of JNK (pJNK), is also evident in BxPC-3 cells exposed for a short time to either free SN-38 or IMMU-132, but not naked hRS7 (not shown). Increased amounts of pJNK are evident by 4 h, with no appreciable change at 6 h. There is a higher intensity of phosphorylation in the cells exposed to free-SN-38 as compared to IMMU-132, but both are substantially higher than controls. As an end-point for the mechanism of action of IMMU-132, measurements of dsDNA breaks were made in BxPC-3 cells. Exposure of BxPC-3 to IMMU-132 for only 30 min resulted in a greater than two-fold induction of γH2AX when compared to a non-targeting control ADC (Table 11). Approximately 70% of the cells were positive for γH2AX staining versus <20% for naked hRS7, hA20-SN-38 irrelevant ADC, and untreated controls (P<0.0002).

TABLE 11

IMMU-132-mediated dsDNA breaks in BxPC-3: γH2AX induction.[a]

| Treatment | Mean Fluorescence Intensity | Percent Positive |
| --- | --- | --- |
| Untreated | 2516 ± 191 | 18.8 ± 6.3 |
| hRS7 | 2297 ± 18 | 13.0 ± 0.6 |
| hA20-SN-38 | 2246 ± 58 | 12.7 ± 2.4 |
| IMMU-132 | 5349 ± 234 | 69.0 ± 4.1 |

[a]IMMU-132 vs. all 3 control treatments, P < 0.0002 (onetailed t-Test; N = 3).

Pharmacokinetics of IMMU-132—

Binding to the human neonatal receptor (FcRn) was determined by BIACORE analysis (not shown). Using a low-density FcRn biosensor chip (density=1302 RU), three independent binding runs at five different concentrations (400 to 25 nM) were conducted for each agent. Overall, both hRS7 and IMMU-132 demonstrate KD-values in the nanomolar range (92.4±5.7 nM and 191.9±47.6 nM, respectively), with no significant difference between the two. Mice were injected with IMMU-132, with the clearance of IMMU-132 versus the hRS7 IgG compared to the parental hRS7 using two ELISAs (not shown). Mice injected with hRS7 demonstrated a biphasic clearance pattern (not shown) that was similar to what was observed for the hRS7 targeting portion of IMMU-132 (not shown), with alpha and beta half-lives of approximately 3 and 200 h, respectively. In contrast, a rapid clearance of intact IMMU-132 was observed with a half-life of 11 h and mean residence time (MRT) of 15.4 h (not shown).

To further confirm that disruption of interchain disulfide bonds does not alter the PK of the targeting antibody, the PK of parental hRS7 was compared to modified hRS7 (hRS7-NEM). There were no significant differences noted between either agent in terms of half-life, Cmax, AUC, clearance, or MRT (not shown).

IMMU-132 Efficacy in Human Gastric Carcinoma Xenografts—

Efficacy of IMMU-132 has been demonstrated previously in non-small-cell lung, colon, TNBC, and pancreatic carcinoma xenograft models (Cardillo et al., 2011, Clin Cancer Res 17:3157-69; Goldenberg et al., Poster presented at San Antonio Breast Cancer Symposium, December 9-13, Abstr P5-19-08). To further extend these findings to other gastro-intestinal cancers, IMMU-132 was tested in mice bearing a human gastric carcinoma xenograft, NCI-N87 (not shown). Treatment with IMMU-132 achieved significant tumor regressions compared to saline and non-targeting hA20 (anti-CD20)-SN-38 ADC controls (not shown; P<0.001). There were 6 of 7 mice in the IMMU-132 group that were partial responders that lasted for more than 18 days after the last therapy dose was administered to the animals. This resulted in a mean time to progression (TTP) of 41.7±4.2 days compared to no responders in the control ADC group, with a TTP of 4.1±2.0 days (P<0.0001). Overall, the median survival time (MST) for IMMU-132-treated mice was 66 days versus 24 days for control ADC and 14 days for saline control animals (not shown; P<0.0001).

Clinically-Relevant Dosing Schemes—

The highest repeated doses tolerated of IMMU-132 currently being tested clinically are 8 and 10 mg/kg given on days 1 and 8 of 21-day cycles. A human dose of 8 mg/kg translates to a murine dose of 98.4 mg/kg, or approximately 2 mg to a 20 g mouse. Three different dose schedules of fractionated 2 mg of IMMU-132 were examined in a human pancreatic adenocarcinoma xenograft model (BxPC-3). This total dose was fractionated using one of three different dosing schedules: one group received two IMMU-132 doses of 1 mg (therapy days 1 and 15), one received four doses of 0.5 mg (therapy days 1, 8, 22, and 29), and the final group eight doses of 0.25 mg (therapy days 1, 4, 8, 11, 22, 25, 29, and 32). All three dosing schemes provided a significant anti-tumor effect when compared to untreated control animals, both in terms of tumor growth inhibition and overall survival (not shown; P<0.0009 and P<0.0001, respectively). There are no significant differences in TTP between the three different treatment groups, which ranged from 22.4±10.1 days for the 1-mg dosing group to 31.7±14.5 days for the 0.25-mg dosing group (TTP for untreated control group=5.0±2.3 days).

A similar dose schedule experiment was performed in mice bearing NCI-N87 human gastric tumor xenografts (not shown). All three dose schedules had a significant anti-tumor effect when compared to untreated control mice but were no different from each other (AUC; P<0.0001). Likewise, in terms of overall survival, while all three dose schedules provided a significant survival benefit when compared to untreated control (P<0.0001), there were no differences between any of these three different schedules.

To further discriminate possible dosing schemes, mice bearing NCI-N87 tumors were subjected to chronic IMMU-132 dosing in which mice received 0.5 mg injections of IMMU-132 once a week for two weeks followed by one week off before starting another cycle (not shown), as in the current clinical trial schedule. In all, four treatment cycles were administered to the animals.

This dosing schedule slowed tumor growth with a TTP of 15.7±11.1 days versus 4.7±2.2 days for control ADC-treated mice (P=0.0122). Overall, chronic dosing increased the median 19 survival 3-fold from 21 days for control ADC-treated mice to 63 days for those animals administered IMMU-132 (P=0.0001). Importantly, in all these different dosing scheme evaluations, no treatment-related toxicities were observed in the mice as demonstrated by no significant loss in body weight (data not shown).

Discussion

In a current Phase I/II clinical trial (ClinicalTrials.gov, NCT01631552), IMMU-132 (sacituzumab govitecan) is demonstrating objective responses in patients presenting with a wide range of solid tumors (Starodub et al., 2015, Clin Cancer Res 21:3870-78). As this Phase I/II clinical trial continues, efficacy of IMMU-132 needs to be further explored in an expanding list of Trop-2-positive cancers. Additionally, the uniqueness of IMMU-132, in contrast to other clinically relevant ADCs that make use of ultratoxic drugs, needs to be further elucidated as we move forward in its clinical development.

The work presented here further characterizes IMMU-132 and demonstrates its efficacy against gastric and pancreatic adenocarcinoma at clinically-relevant dosing schemes. The prevailing view of a successful ADC is that it should use an antibody recognizing an antigen with high tumor expression levels relative to normal tissue and one that preferably internalizes when bound to the tumor cells (Panowski et al., 2014, mAbs 6:34-45). All of the currently approved ADCs have used an ultra-toxic drug (pM IC50) coupled to the antibody by a highly stable linker at low substitution ratios (2-4 drugs per antibody). IMMU-132 diverges from this paradigm in three main aspects: (i) SN-38, a moderately cytotoxic drug (nM $IC_{50}$), is used as the chemotherapeutic agent, (ii) SN-38 is conjugated site-specifically to 8 inter-chain thiols of the antibody, yielding a substitution of 7.6 drugs per antibody, and (iii) a carbonate linker is used that is cleavable at low pH, but will also release the drug with a half-life in serum of ~24 h (Cardillo et al., 2011, Clin Cancer Res 17:3157-69). IMMU-132 is composed of an antibody that internalizes after binding to an epitope, as we have shown, that is specific for human Trop-2, which is highly expressed on many different types of epithelial tumors, as well as at lower concentrations in their corresponding normal tissues (Shih et al., 1995, Cancer Res 55:5857s-63s). Despite the presence in normal tissues, prior studies in monkeys, which also express Trop-2 in similar tissues, indicated relatively mild and reversible histopathological changes even at very high doses where dose-limiting neutropenia and diarrhea occurred, suggesting the antigen in the normal tissues was sequestered in some manner, or that the use of a less toxic drug spared these normal tissues from severe damage (Cardillo et al., 2011, Clin Cancer Res 17:3157-69).

Herein, we expanded an assessment of Trop-2 expression on multiple human solid tumor lines, examining in vitro expression in a more quantitative manner than reported previously, but also, importantly, in xenografts that illustrate Trop-2 expression ranging from homogenous (e.g., NCIN87) to very focal (e.g., COLO 205). Overall, surface expression levels of Trop-2 determined in vitro correlated with staining intensity upon IHC analysis of xenografts. It is particularly interesting that even in a tumor like COLO 205, where there are only focal pockets of Trop-2-expressing cells revealed by immunohistology, IMMU-132 was still capable of eliciting specific tumor regressions, suggesting that a bystander effect may occur as a result of the release of SN-38 from the conjugate bound to the antigen-presenting cells (Cardillo et al., 2011, Clin Cancer Res 17:3157-69). Indeed, SN-38 readily penetrates cell membranes, and therefore its local release within the tumor microenvironment provides another mechanism for its entry into cells without requiring internalization of the intact conjugate. Importantly, the SN-38 bound to the conjugate remains in a fully active state; namely, it is not glucuronidated and would be in the lactone ring form at the time of release (Sharkey et al., 2015, Clin Cancer Res, 21:5131-8). This property is unique, distinguishing IMMU-132's ability to localize a fully active form of SN-38 in a more selective manner than any of the other slow-release SN-38 or irinotecan agents studied to date.

The Phase I clinical trial with IMMU-132 identified 8 to 10 mg/kg given weekly for two weeks on a 21-day cycle for further investigation in Phase II (Starodub et al., 2015, Clin Cancer Res 21:3870-78). Patients with a wide range of metastatic solid tumors, including pancreatic and gastric cancers, have shown extended periods of disease stabilization after relapsing to multiple prior therapies (Starodub et al., 2015, Clin Cancer Res 21:3870-78; Starodub et al., 2014, J Clin Oncol 32:5s (Suppl Abstr 3032)). Additional studies in xenograft models were undertaken to determine if different dosing schedules may be more efficacious. To this end, the equivalent to the human dose of 8 mg/kg (mouse dose of 98.4 mg/kg) was fractionated over three different dosing schedules, including every other week, weekly, or twice-weekly on a 21-day cycle. In the pancreatic and gastric tumor models, no significant difference in therapeutic responses were observed for all three schedules, with tumors progressing only after therapy was discontinued. Therefore, these data support the continued use of the once-weekly dosing regimen currently being pursued clinically.

With clinical trials recommending an IMMU-132 each treatment dose of 8 to 10 mg/kg (Starodub et al., 2015, Clin Cancer Res 21:3870-78), it was important to examine whether the antibody alone might contribute to the IMMU- 132's activity. Previous studies in nude mice-human xenograft models had included unconjugated hRS7 IgG alone (e.g., repeated doses of 25 to 50 mg/kg), with no evidence of therapeutic activity (Cardillo et al., 2011, Clin Cancer Res 17:3157-69); however, studies in mice cannot always predict immunological functionality. ADCC activity of hRS7 in vitro has been reported in Trop-2-positive ovarian and uterine carcinomas (Raji et al., 2011, J Exp Clin Cancer Res 30:106; Bignotti et al., 2011, Int J Gynecol Cancer 21:1613-21; Varughese et al., 2011, Am J Obstet Gynecol 205:567; Varughese et al., 2011, Cancer 117:3163-72). We confirmed unconjugated hRS7 ADCC activity in three different cells lines, but found IMMU-132 lost 60-70% of its effector function. Since the reduced/NEM-blocked IgG has a similar loss of ADCC activity, it appears that the attachment of the CL2A-SN-38 component was not, in itself, responsible.

Antibodies also can elicit cell death by acting on various apoptotic signaling pathways. However, we did not observe any effects of the unconjugated antibody in a number of apoptotic signaling pathways, but instead noted IMMU-132 elicited similar intrinsic apoptotic events as SN-38. Early events include the phosphorylation of JNK1/2 as well as the up-regulation of p21WAF1/Cip1 leading to the activation of caspase-9, -7, and -3, with the end result of PARP cleavage and significant levels of dsDNA breaks, as measured by increased amounts of phosphorylated histone H2AX (γH2AX)41. These data suggest that IMMU-132's primary mechanism of action is related to SN-38.

Surface plasmon resonance (BIACORE) analysis did not detect a significant difference in IMMU-132's binding to the human neonatal receptor (FcRn), despite the average binding levels being ~2-fold lower for IMMU-132. FcRn binding has been linked to an extended IgG half-life in serum (Junghans & Anderson, 1996, Proc Natl Acad Sci USA 93:5512-16), but because an antibody's affinity for FcRn in vitro may not correlate with in vivo clearance rates (Datta-Mannan et al., 2007, J Biol Chem 282:1709-17), the overall importance of this finding is unknown. Previous experiments in tumor-bearing mice using $^{111}$In-DTPA-IMMU-132 revealed that the conjugate cleared at a somewhat faster rate from the serum than $^{111}$In-DTPA-hRS7, although both had similar tumor uptake (Cardillo et al., 2011, Clin Cancer Res 17:3157-69). In the current studies, an ELISA assay that also measured the clearance of the IgG component found IMMU-132 and the reduced and NEM-blocked IgG cleared at similar rates as unconjugated hRS7, suggesting that the coupling to the interchain disulfides does not destabilize the antibody. As expected, when using an ELISA that monitored the clearance of the intact conjugate (capturing using an anti-SN-38 antibody and probe with an anti-idiotype antibody), its clearance rate was faster than when monitoring only the IgG component. This difference simply reflects SN-38's release from the conjugate with a half-life of ~1 day. We also have examined the clearance rates of sacituzumab govitecan conjugates prepared at different substitution levels by ELISA, and again found no appreciate difference in their clearance rates (Goldenberg et al., 2015, Oncotarget 8:22496-512). Overall, these data suggest that mild reduction of the antibody, with the subsequent site-specific modification of some or all interchain disulfides, has minimal if any impact on the serum clearance of the IgG, but IMMU-132's overall clearance rate will be defined largely by the rate of release of SN-38 from the linker.

Additionally, extensive cell-binding experiments demonstrated no significant difference in the binding of IMMU-132, the unconjugated antibody, or the NEM-modified antibody, suggesting that the site-specific linkage to the interchain disulfides protects the antigen-binding properties of the antibody. Interestingly, when analyzed by BIACORE, which more accurately measures the on-rate and off-rate in addition to overall affinity, IMMU-132 had a significant 2-fold improvement in calculated KD-values for Trop-2 binding when compared to naked hRS7.

We speculate that this improvement may be result of the added hydrophobicity when SN-38 is conjugated to the antibody. Hydrophobic residues, as well as hydrophobicity of enclosed regions of protein binding sites, have been shown to impart a stronger affinity for the epitope (Park et al., 2000, Nat Biotechnol 18:194-98; Berezov et al., 2001, J Med Chem 44:2565-74; Young et al., 2007, Proc Natl Acad Sci USA 104:808013). These regions do not have to be at the protein-protein interface, but can lie in surrounding, less energetically contact residues (Li et al., 2005, Structure 13:297-307). While none of the SN-38 conjugation sites are present in the complement-determining regions (CDR) of hRS7, the prospects that the SN-38 on the antibody may displace some of the water molecules around the epitope, resulting in the improved binding affinity observed for IMMU-132 relative to naked hRS7, cannot be discounted.

Most efforts in ADC development have been directed towards using a stable linker and an ultratoxic drug, with preclinical studies indicating the specific optimal requirements for those conjugates (Panowski et al., 2014, inAbs 6:34-45; Phillips et al., 2008, Cancer Res 68:9280-90). For example, a comparison of T-DM1 to another less stable derivative, T-SSPDM1, revealed that intact T-SSP-DM1 cleared at an approximately 2-fold faster rate than T-DM-1 in non-tumor-bearing mice (Phillips et al., 2008, Cancer Res 68:9280-90; Erickson et al., 2012, Mol Cancer Ther 11:1133-42), with 1.5-fold higher levels of T-DM1 compared to T-SSPDM1 in the tumors. Unexpectedly, and most interesting, was the finding that the amount of free, active maytansinoid catabolites in the targeted tumors was very similar between the two ADCs (Erickson et al., 2012, Mol Cancer Ther 11:1133-42).

In other words, T-SSP-DM1 was able to overcome its deficiencies in linker stability due to the fact that the lower stability resulted in more efficient release of the drug at the tumor than the more stable T-DM1. Not surprisingly, this equivalency of active drug-catabolite between the two ADCs in the tumors resulted in similar anti-tumor effects in tumor-bearing animals. Ultimately, T-DM1 was chosen based on toxicity issues that arise when using an ultra-toxic drug and less stable linkers (Phillips et al., 2008, Cancer Res 68:9280-90). Since SN-38 is at least a log-fold less toxic than these maytansines, its release from the ADC is expected to have less toxicity. However, even with its release in serum, the amount of SN-38 localized in human gastric or pancreatic tumor xenografts was up to 136-fold higher than in tumor-bearing mice injected with irinotecan doses that had >20-fold higher SN-38 equivalents (Sharkey et al., 2015, Clin Cancer Res, 21:5131-8). While we have tested more stable linkers in the development of IMMU-132, they were significantly less effective in xenograft tumor models than IMMU-132 (Govindan et al., 2013, Mol Cancer Ther 12:968-78).

Similarly, linkers that released SN-38 more quickly (e.g., serum half-life of ~10 h) also were less effective in xenograft models (Moon et al., 2008, J Med Chem 51:6916-26; Govindan et al., 2009, Clin Chem Res 15:6052-61), suggesting that there is an optimal window at which the release of SN-38 leads to improved efficacy. Thus, current data demonstrate that IMMU-132 is a more efficient way to target and release the drug at the tumor than irinotecan.

Early clinical studies have shown encouraging objective responses in various solid tumors, and importantly have indicated a better safety profile, with a lower incidence of diarrhea, than irinotecan therapy (Starodub et al., 2015, Clin Cancer Res 21:3870-78).

In summary, IMMU-132 (sacituzumab govitecan) is a paradigm-shift in ADC development. It uses a moderately-stable linker to conjugate 7-8 molecules of the more tolerable active metabolite of irinotecan, SN-38, to an anti-Trop-2 antibody. Despite these seemingly counterintuitive characteristics vis-a-vis ultra-toxic ADCs, non-clinical studies have demonstrated that IMMU-132 very effectively targets Trop-2-expressing tumors with significant efficacy and no appreciable toxicity. In early phase I/II clinical trials against a wide range of solid tumors, including pancreatic, gastric, TNBC, small-cell and non-small-cell lung carcinomas, IMMU-132 is likewise exhibiting anti-tumor effects with manageable toxicities in these patients, with no immune responses to either the IgG or SN-38 detected, even after many months of dosing (Starodub et al., 2015, Clin Cancer Res 21:3870-78). Given the elevated expression of Trop-2 on such a wide variety of solid tumors, IMMU-132 continues to be studied clinically, especially in advanced cancers that have been refractory to most current therapy strategies.

Example 18. Further Results from Phase I/II Clinical Studies

Triple-Negative Breast Cancer (TNBC)

The phase I/II clinical trial (NCT01631552) discussed in the Examples above has continued, accruing 56 TNBC patients who were treated with 10 mg/kg. The patient population had previously been extensively treated before initiating IMMU-132 therapy, with at least 2 prior lines of therapy including taxane treatment. Previous treatments included cyclophosphamide, doxorubicin, carboplatin, gemcitabine, capecitabine, eribulin, cisplatinum, anastrozole, vinorelbine, bevacizumab and tamoxifen. Despite this extensive treatment history TNBC patients responded well to IMMU-132, with 2 confirmed complete responses (CR), 13 partial responses (PR) and 25 stable disease (SD), for an objective response rate of 29% (15/52) (not shown). Adding the incidence of CR plus PR plus SD, treatment in TNBC resulted in a 71% favorable response rate for IMMU-132 treated patients (not shown). The median time to progression in this heavily pretreated population of TNBC patients was 9.4 months, with a range of 2.9 to 14.2 months to date. However, 72% of patients in the study were still ongoing treatment.

Metastatic NSCLC

The clinical trial is also ongoing for patients with metastatic non-small cell lung cancer (NSCLC), with 29 assessable patients accrued to date, who were treated with 8 or 10 mg/kg IMMU-132. The best responses by RESIST 1.1 criteria were determined (not shown). Out of 29 patients, there were 8 PR and 13 SD. The time to progression for NSCLC patients showed that 21/33 (64%) of NSCLC patients exhibited PR or SD (not shown). The median time to progression was 9/4 months, with a range from 1.8 to 15.5+ months and 47% of patients still undergoing treatment. Progression-free survival in NSCLC patients treated with 8 or 10 mg/kg IMMU-132 was determined (not shown). Median PFS was 3.4 months at 8 mg/kg and 3.8 months at 10 mg/kg. However, studies are still ongoing and the median progression-free survival numbers are likely to improve.

Metastatic SCLC

Comparable results in metastatic SCLC patients were observed (not shown). Time to progression (not shown) showed a median of 4.9 months, with a range of 1.8 to 15.7+ months and 7 patients still undergoing treatment with IMMU-132. The progression free survival (not shown) showed a median PFS of 2.0 months at 8 mg/kg and 3.6 months at 10 mg/kg. The median OS was 8.1 months at 8 mg/kg and could not be determined yet for 10 mg/kg.

Urothelial Cancer

Similar results were obtained with urothelial cancer patients treated with 8 or 10 mg/kg IMMU-132. The best response data for 11 assessable patients showed 6 PR and 2 SD (not shown). Time to progression (not shown) showed a median of 8.1 months, with a range of 3.6 yo 9.7+ months.

In summary, the continuing phase I/II clinical trial shows superior efficacy of IMMU-132, when administered at the recited dosages of ADC, in at least TNBC, NSCLC, SCLC and urothelial cancers. The superior therapeutic effect in these heavily pretreated and resistant metastatic cancers occurred without inducing severe toxicities that might preclude clinical use. IMMU-132 showed an acceptable safety profile in heavily pretreated patients with diverse solid cancers, and a median of 2-5 prior therapies. Only neutropenia showed an incidence of greater than 20% of the patient population for Grade 3 or higher adverse reactions. The study further demonstrates that repeated doses of IMMU-132 may be administered to human patients, at therapeutic dosages, without evoking interfering host anti-IMMU-132 antibodies. These results demonstrate the safety and utility of IMMU-132 for treating diverse Trop-2 positive cancers in human patients.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference.

We claim:

1. A method of treating a Trop-2 positive cancer comprising administering to a human patient with a Trop-2 positive cancer an ADC comprising SN-38 conjugated to a linker moiety attached to an anti-TROP-2 antibody or antigen-binding fragment thereof, wherein the patient has relapsed from or is refractory to treatment with a checkpoint inhibitor, wherein the checkpoint inhibitor is selected from the group consisting of MPDL3280A, pembrolizumab, nivolumab, ipilimumab, pidilizumab, MDX-1105, durvalumab, BMS-936559, and tremelimumab.

2. The method of claim 1, wherein the checkpoint inhibitor is MPDL3280A.

3. The method of claim 1, wherein the anti-Trop-2 antibody is an hRS7 antibody comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6).

4. The method of claim 1, wherein the linker is CL2A and the structure of the ADC is MAb-CL2A-SN-38

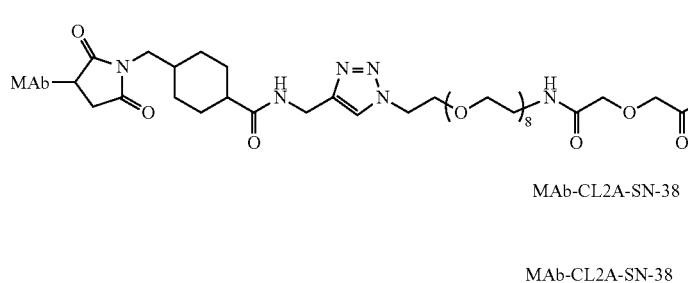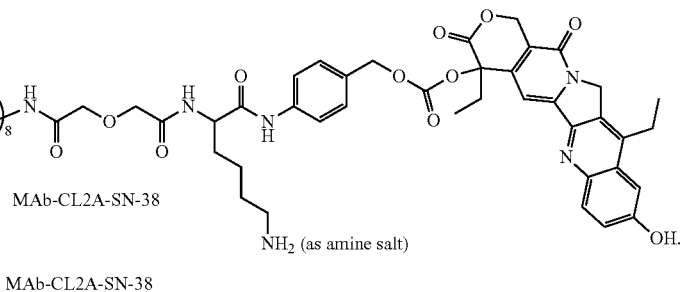

MAb-CL2A-SN-38

MAb-CL2A-SN-38

5. The method of claim 4, wherein the anti-Trop-2 antibody is an hRS7 antibody comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDD-FKG, SEQ ID NO:5) and CDR3 (GGFGSSYWYFDV, SEQ ID NO:6).

6. The method of claim 1, wherein the cancer is selected from the group consisting of colorectal, lung, stomach, urinary bladder, renal, pancreatic, breast, ovarian, uterine, esophageal and prostatic cancer.

7. The method of claim 1, wherein the cancer is triple negative breast cancer.

8. The method of claim 1, wherein the cancer is selected from the group consisting of triple-negative breast cancer, HER+, ER+, progesterone+breast cancer, metastatic non-small-cell lung cancer, metastatic small-cell lung cancer, metastatic endometrial cancer, metastatic urothelial cancer and metastatic pancreatic cancer.

9. The method of claim 1, wherein the ADC is administered at a dosage of between 3 mg/kg and 18 mg/kg.

10. The method of claim 9, wherein the dosage is selected from the group consisting of 3 mg/kg, 4 mg/kg, 6 mg/kg, 7 mg/kg, 8 mg/kg, 9 mg/kg, 10 mg/kg, 11 mg/kg, 12 mg/kg, 16 mg/kg and 18 mg/kg.

11. The method of claim 1, wherein the ADC is administered at a dosage of between 8 mg/kg and 12 mg/kg.

12. The method of claim 1, wherein the ADC is administered at a dosage of between 8 mg/kg and 10 mg/kg.

13. The method of claim 1, wherein the ADC is administered at a dosage of 10 mg/kg.

14. The method of claim 1, wherein the treatment results in a reduction in tumor size of at least 15%, at least 20%, at least 30%, or at least 40%.

15. The method of claim 1, wherein the ADC comprises 4 or more molecules of SN-38 conjugated to the antibody or antigen-binding fragment thereof.

16. The method of claim 1, wherein the ADC comprises 6 to 8 molecules of SN-38 conjugated to the antibody or antigen-binding fragment thereof.

17. The method of claim 1, wherein the cancer is metastatic.

18. The method of claim 17, further comprising reducing in size or eliminating the metastases.

19. The method of claim 4, wherein the 10-hydroxy position of SN-38 in MAb-CL2A-SN-38 is a 10-O-ester or 10-O-carbonate derivative using a 'COR' moiety, wherein "CO" is carbonyl and the "R" group is selected from (i) an N,N-disubstituted aminoalkyl group "$N(CH_3)_2\text{-}(CH_2)_n\text{-}$" wherein n is 1-10 and wherein the terminal amino group is optionally in the form of a quaternary salt; (ii) an alkyl residue "$CH_3\text{-}(CH_2)_n\text{-}$" wherein n is 0-10; (iii) an alkoxy moiety "$CH_3\text{-}(CH_2)n\text{-}O\text{-}$" wherein n is 0-10; (iv) an "$N(CH_3)_2\text{-}(CH_2)_n\text{-}O\text{-}$" wherein n is 2-10; or (v) an "$R_1O\text{—}(CH_2\text{-}CH_2\text{-}O)_n\text{-}CH_2\text{-}CH_2\text{-}O\text{-}$" wherein $R_1$ is ethyl or methyl and n is an integer with values of 0-10.

20. The method of claim 1, further comprising administering to the patient at least one other anti-cancer therapy selected from the group consisting of surgery, external radiation, radioimmunotherapy, immunotherapy, chemotherapy, antisense therapy, interference RNA therapy, treatment with a therapeutic agent and gene therapy.

21. The method of claim 20, wherein the therapeutic agent is a drug, toxin, immunomodulator, second antibody, antigen-binding fragment of a second antibody, pro-apoptotic agent, toxin, RNase, hormone, radionuclide, anti-angiogenic agent, siRNA, RNAi, chemotherapeutic agent, cytokine, chemokine, prodrug or enzyme.

22. The method of claim 21, wherein the drug is selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamicin, camptothecin, carboplatin, 10-hydroxycamptothecin, carmustine, celebrex, chlorambucil, cisplatinum, Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839.

23. The method of claim 21, wherein the wherein the immunomodulator is selected from the group consisting of cytokines, lymphokines, monokines, stem cell growth factors, lymphotoxins, hematopoietic factors, colony stimulating factors (CSF), interferons (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, transforming growth factor (TGF), TGF-α, TGF-β, insulin-like growth factor (IGF), erythropoietin, thrombopoietin, tumor necrosis factor (TNF), TNF-α, TNF-β, mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, 51 factor, IL-1, IL-1 cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21, IL-23, IL-25, LIF, kit-ligand, FLT-3, angiostatin, thrombospondin and endostatin.

24. The method of claim 21, wherein the radionuclide is selected from the group consisting of $^{11}$C, $^{13}$N, $^{15}$O, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{67}$Ga, $^{75}$Br, $^{75}$Se, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo, $^{99m}$Tc, $^{103m}$Rh, $^{103}$Ru, $^{105}$Rb, $^{105}$Ru, $^{107}$Hg, $^{109}$Pd, $^{109}$Pt, $^{111}$Ag, $^{111}$In, $^{113m}$In, $^{119}$Sb, $^{121m}$Te, $^{122m}$Te, $^{125}$I, $^{125m}$Te, $^{126}$I, $^{131}$I, $^{133}$I, $^{142}$Pr, $^{143}$Pr, $^{149}$Pm, $^{152}$Dy, $^{153}$Sm, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{225}$Ac, $^{227}$Th and $^{255}$Fm.

25. The method of claim 21, wherein the toxin is selected from the group consisting of ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

* * * * *